(12) United States Patent
Arizti et al.

(10) Patent No.: US 10,271,997 B2
(45) Date of Patent: Apr. 30, 2019

(54) ABSORBENT ARTICLES HAVING SUBSTRATES HAVING ZONAL TREATMENTS

(71) Applicant: The Procter & Gamble Company, Cincinnati, OH (US)

(72) Inventors: Blanca Arizti, Schmitten (DE); Donald Carroll Roe, West Chester, OH (US); Nelson Edward Greening, II, Cincinnati, OH (US); Marie Brigid O'Reilly, Cincinnati, OH (US); Rachael Eden Walther, Union, KY (US)

(73) Assignee: The Procter & Gamble Company, Cincinnati, OH (US)

( * ) Notice: Subject to any disclaimer, the term of this patent is extended or adjusted under 35 U.S.C. 154(b) by 839 days.

(21) Appl. No.: 14/247,588

(22) Filed: Apr. 8, 2014

(65) Prior Publication Data
US 2015/0282999 A1 Oct. 8, 2015

(51) Int. Cl.
*A61F 13/15* (2006.01)
*A61F 13/495* (2006.01)
(Continued)

(52) U.S. Cl.
CPC .......... *A61F 13/495* (2013.01); *A61F 13/511* (2013.01); *A61F 13/513* (2013.01);
(Continued)

(58) Field of Classification Search
CPC ................... A61F 13/495; A61F 13/511; A61F 13/51113; A61F 13/513; A61F 13/51394;
(Continued)

(56) References Cited

U.S. PATENT DOCUMENTS

| 2,005,298 A | 6/1935 | O'Brien |
| 2,896,618 A | 7/1959 | Schaefer |

(Continued)

FOREIGN PATENT DOCUMENTS

| CN | 03304429 | 3/2003 |
| CN | 03354923 | 3/2003 |

(Continued)

OTHER PUBLICATIONS

All Office Actions, U.S. Appl. No. 14/247,598.
(Continued)

*Primary Examiner* — Bradley H Philips
(74) *Attorney, Agent, or Firm* — Daniel S. Albrecht

(57) ABSTRACT

The present disclosure is directed, in part, to absorbent article comprising a liquid permeable topsheet, a liquid impermeable backsheet, a lateral axis defining a front region on a first side of the lateral axis and a back region on a second side of the lateral axis, and an absorbent core positioned at least partially intermediate the liquid permeable topsheet and the liquid impermeable backsheet. The liquid permeable topsheet may comprise a first zone situated primarily in the front region and having a substantially transferrable chemical treatment and a second zone situated primarily in the back region and having the substantially transferrable chemical treatment. A basis weight of the substantially transferrable chemical treatment may be greater in the second zone than in the first zone.

20 Claims, 73 Drawing Sheets

(51) Int. Cl.
  *A61F 13/511* (2006.01)
  *A61F 13/513* (2006.01)
  *A61F 13/51* (2006.01)
  *A61F 13/84* (2006.01)
  *A61F 13/534* (2006.01)

(52) U.S. Cl.
  CPC .. *A61F 13/51113* (2013.01); *A61F 13/51394* (2013.01); *A61F 13/52* (2013.01); *A61F 13/53436* (2013.01); *A61F 13/8405* (2013.01); *A61F 2013/51117* (2013.01); *A61F 2013/51355* (2013.01)

(58) Field of Classification Search
  CPC ............... A61F 13/52; A61F 13/53436; A61F 13/8405; A61F 2013/51117; A61F 2013/51355
  See application file for complete search history.

(56) References Cited

U.S. PATENT DOCUMENTS

| | | | |
|---|---|---|---|
| 3,559,648 A | 2/1971 | Mason, Jr. | |
| 3,559,649 A | 2/1971 | Grad | |
| 3,595,235 A | 7/1971 | Jespersen | |
| 3,693,622 A | 9/1972 | Jones | |
| 3,714,946 A | 2/1973 | Rudes | |
| 3,799,167 A | 3/1974 | Miller et al. | |
| 4,015,604 A | 4/1977 | Csillag | |
| 4,200,103 A | 4/1980 | Black | |
| 4,321,924 A | 3/1982 | Ahr | |
| 4,395,215 A | 7/1983 | Bishop | |
| 4,397,645 A | 8/1983 | Buell | |
| 4,433,972 A * | 2/1984 | Malfitano | A61F 13/47227 604/385.01 |
| 4,662,877 A | 5/1987 | Williams | |
| 4,692,161 A | 9/1987 | Puletti | |
| 4,695,278 A | 9/1987 | Lawson | |
| 4,795,454 A | 1/1989 | Dragoo | |
| 4,892,536 A | 1/1990 | DesMarais et al. | |
| 4,895,568 A | 1/1990 | Enloe | |
| 4,895,749 A | 1/1990 | Rose | |
| 4,973,325 A | 11/1990 | Sherrod | |
| 4,988,344 A | 1/1991 | Reising | |
| 4,990,147 A | 2/1991 | Freeland | |
| 5,019,069 A | 5/1991 | Klemp | |
| 5,062,838 A | 11/1991 | Nalowaniec | |
| 5,100,398 A | 3/1992 | Leroy | |
| 5,167,654 A | 12/1992 | Yang | |
| 5,171,236 A | 12/1992 | Dreier et al. | |
| 5,269,775 A | 12/1993 | Freeland et al. | |
| D343,232 S | 1/1994 | Lombardi | |
| 5,304,161 A | 4/1994 | Noel et al. | |
| 5,342,337 A | 8/1994 | Runeman | |
| 5,342,338 A | 8/1994 | Roe | |
| 5,352,217 A | 10/1994 | Curro | |
| 5,354,400 A | 10/1994 | Lavash et al. | |
| 5,369,858 A | 12/1994 | Gilmore et al. | |
| 5,383,870 A | 1/1995 | Takai | |
| 5,389,094 A | 2/1995 | Lavash et al. | |
| 5,397,316 A | 3/1995 | LaVon et al. | |
| 5,431,643 A | 7/1995 | Ouellette | |
| 5,439,458 A | 8/1995 | Noel et al. | |
| 5,449,352 A | 9/1995 | Nishino | |
| 5,458,590 A * | 10/1995 | Schleinz | A61F 13/51498 101/483 |
| 5,462,541 A | 10/1995 | Bruemmer et al. | |
| 5,620,430 A | 4/1997 | Bamber | |
| 5,628,097 A | 5/1997 | Benson et al. | |
| 5,643,588 A * | 7/1997 | Roe | A61F 13/8405 424/402 |
| 5,658,639 A | 8/1997 | Curro et al. | |
| H1687 H | 10/1997 | Roe et al. | |
| 5,704,930 A | 1/1998 | Lavash et al. | |
| 5,714,107 A | 2/1998 | Levy et al. | |
| 5,716,351 A | 2/1998 | Roe et al. | |
| 5,762,642 A | 6/1998 | Coles | |
| 5,776,122 A | 7/1998 | Faulks et al. | |
| 5,785,697 A | 7/1998 | Trombetta et al. | |
| 5,807,367 A | 9/1998 | Dilnik | |
| 5,853,402 A | 12/1998 | Faulks et al. | |
| 5,873,868 A | 2/1999 | Nakahata | |
| 5,916,661 A | 6/1999 | Benson et al. | |
| 5,925,026 A | 7/1999 | Arteman et al. | |
| 5,941,864 A | 8/1999 | Roe | |
| 5,957,907 A | 9/1999 | Sauer | |
| 5,968,028 A | 10/1999 | Roe et al. | |
| 5,989,478 A | 11/1999 | Ouellette et al. | |
| 5,990,337 A | 11/1999 | Kleiner | |
| 5,998,695 A | 12/1999 | Roe et al. | |
| 6,010,490 A | 1/2000 | Freeland et al. | |
| 6,025,049 A | 2/2000 | Ouellette et al. | |
| D423,098 S | 4/2000 | Stancyk, Jr. | |
| 6,090,090 A | 7/2000 | Roe et al. | |
| 6,093,871 A | 7/2000 | Takai | |
| 6,107,537 A | 8/2000 | Elder et al. | |
| 6,117,523 A | 9/2000 | Sugahara | |
| 6,120,485 A | 9/2000 | Gustafsson et al. | |
| 6,120,783 A | 9/2000 | Roe et al. | |
| 6,123,692 A | 9/2000 | Guidotti et al. | |
| 6,152,907 A | 11/2000 | Widlund et al. | |
| 6,152,908 A | 11/2000 | Widlund et al. | |
| 6,156,020 A | 12/2000 | Roe et al. | |
| 6,156,022 A | 12/2000 | Hedlund | |
| 6,180,052 B1 | 1/2001 | Ouellette et al. | |
| 6,217,890 B1 | 4/2001 | Paul | |
| 6,221,460 B1 | 4/2001 | Weber et al. | |
| 6,231,555 B1 | 5/2001 | Lynard et al. | |
| 6,231,948 B1 | 5/2001 | Ouellette et al. | |
| 6,248,098 B1 | 6/2001 | Sayama | |
| 6,262,331 B1 | 7/2001 | Nakahata et al. | |
| 6,274,218 B1 | 8/2001 | Shimizu | |
| 6,280,428 B1 | 8/2001 | Lash et al. | |
| 6,290,979 B1 | 9/2001 | Roe et al. | |
| 6,328,722 B1 | 12/2001 | Lavash et al. | |
| 6,391,011 B1 | 5/2002 | Davis et al. | |
| 6,406,465 B1 | 6/2002 | Otsubo | |
| 6,423,884 B1 | 7/2002 | Oehmen | |
| 6,443,936 B1 | 9/2002 | Hamilton et al. | |
| 6,450,998 B1 | 9/2002 | Otsubo et al. | |
| 6,458,111 B1 | 10/2002 | Onishi et al. | |
| 6,458,114 B1 | 10/2002 | Mishima et al. | |
| 6,465,711 B1 | 10/2002 | Brisebois | |
| 6,476,288 B1 | 11/2002 | VanRijswijck et al. | |
| 6,482,193 B1 * | 11/2002 | Samuelsson | A61F 13/4702 604/380 |
| 6,494,871 B1 | 12/2002 | Lariviere et al. | |
| 6,498,284 B1 | 12/2002 | Roe | |
| 6,610,902 B1 * | 8/2003 | Gustafsson | A61F 13/47227 604/367 |
| 6,632,504 B1 | 10/2003 | Gillespie et al. | |
| 6,639,119 B2 | 10/2003 | Roe et al. | |
| 6,676,646 B2 | 1/2004 | Bast et al. | |
| 6,723,892 B1 | 4/2004 | Daley et al. | |
| 6,770,579 B1 | 8/2004 | Dawson et al. | |
| 6,811,239 B1 | 11/2004 | Salacz | |
| 6,860,874 B2 | 3/2005 | Gubernick | |
| 6,861,571 B1 | 3/2005 | Roe et al. | |
| 6,965,058 B1 * | 11/2005 | Raidel | A61F 13/47218 604/367 |
| 7,005,558 B1 | 2/2006 | Johansson et al. | |
| 7,056,311 B2 | 6/2006 | Kinoshita et al. | |
| 7,067,711 B2 | 6/2006 | Kuroda et al. | |
| 7,102,054 B1 | 9/2006 | Cree et al. | |
| 7,150,733 B2 | 12/2006 | Yamakawa et al. | |
| 7,163,528 B2 | 1/2007 | Christon et al. | |
| 7,172,801 B2 | 2/2007 | Hoying et al. | |
| 7,204,830 B2 | 4/2007 | Yoshitaka et al. | |
| 7,241,280 B2 | 7/2007 | Christon et al. | |
| 7,252,656 B2 | 8/2007 | Bonelli et al. | |
| 7,270,651 B2 | 9/2007 | Adams et al. | |
| 7,270,861 B2 | 9/2007 | Broering et al. | |
| 7,306,582 B2 | 12/2007 | Adams et al. | |
| 7,311,696 B2 | 12/2007 | Christon et al. | |

(56) References Cited

U.S. PATENT DOCUMENTS

| | | |
|---|---|---|
| 7,335,810 B2 | 2/2008 | Yoshimasa et al. |
| 7,344,523 B2 | 3/2008 | Van Gompel et al. |
| 7,388,123 B2 | 6/2008 | Cowell et al. |
| 7,402,157 B2 | 7/2008 | Christon et al. |
| 7,410,683 B2 | 8/2008 | Curro et al. |
| 7,507,459 B2 | 3/2009 | Turner et al. |
| 7,537,585 B2 | 5/2009 | Christon et al. |
| 7,553,532 B2 | 6/2009 | Turner et al. |
| 7,589,249 B2 | 9/2009 | Gubernick et al. |
| 7,648,752 B2 | 1/2010 | Hoying et al. |
| 7,666,174 B2 | 2/2010 | Onishi et al. |
| 7,670,665 B2 | 3/2010 | Hoying et al. |
| 7,682,686 B2 | 3/2010 | Curro et al. |
| 7,718,243 B2 | 5/2010 | Curro et al. |
| 7,718,844 B2 | 5/2010 | Olson |
| 7,727,213 B2 | 6/2010 | Nomoto et al. |
| 7,732,657 B2 | 6/2010 | Hammons et al. |
| 7,754,050 B2 | 7/2010 | Redd et al. |
| 7,785,690 B2 | 8/2010 | Turner et al. |
| 7,812,213 B2 | 10/2010 | Doverbo et al. |
| 7,824,385 B2 | 11/2010 | Ecker |
| 7,829,173 B2 | 11/2010 | Turner et al. |
| 7,838,099 B2 | 11/2010 | Curro et al. |
| 7,867,210 B2 | 1/2011 | Mori et al. |
| 7,910,195 B2 | 3/2011 | Hammons et al. |
| 7,938,635 B2 | 5/2011 | Heilman et al. |
| 7,967,801 B2 | 6/2011 | Hammons et al. |
| 7,972,316 B2 | 7/2011 | Toyoshima et al. |
| 7,972,317 B2 | 7/2011 | Christon et al. |
| 7,993,317 B2 | 8/2011 | Hammons et al. |
| 8,022,267 B2 | 9/2011 | Hellström et al. |
| 8,030,535 B2 | 10/2011 | Hammons et al. |
| 8,039,685 B2 | 10/2011 | Mason, Jr. et al. |
| 8,058,501 B2 | 11/2011 | Hammons et al. |
| 8,075,977 B2 | 12/2011 | Curro et al. |
| 8,142,876 B2 | 3/2012 | Ueminami et al. |
| 8,153,225 B2 | 4/2012 | Turner et al. |
| 8,153,226 B2 | 4/2012 | Curro et al. |
| 8,157,778 B2 | 4/2012 | Moriya et al. |
| 8,158,043 B2 | 4/2012 | Gibson et al. |
| 8,193,407 B2 | 6/2012 | Mansfield et al. |
| D664,642 S | 7/2012 | Hood et al. |
| 8,231,592 B2 | 7/2012 | Suzuki et al. |
| 8,241,543 B2 | 8/2012 | O'Donnell et al. |
| 8,262,633 B2 | 9/2012 | Larson et al. |
| 8,292,864 B2 | 10/2012 | Hood et al. |
| 8,318,284 B2 | 11/2012 | Curro et al. |
| 8,357,445 B2 | 1/2013 | Hammons et al. |
| 8,378,165 B2 | 2/2013 | Visscher et al. |
| 8,440,587 B2 | 5/2013 | Arora et al. |
| 8,536,401 B2 | 9/2013 | Ecker et al. |
| 8,759,606 B2 | 6/2014 | Bond et al. |
| 2001/0020157 A1 | 9/2001 | Mizutani et al. |
| 2002/0013567 A1 | 1/2002 | Mishima et al. |
| 2002/0138054 A1 | 9/2002 | Erdman |
| 2003/0021951 A1 | 1/2003 | Desai et al. |
| 2003/0055392 A1 | 3/2003 | Tagami et al. |
| 2003/0078553 A1 | 4/2003 | Wada et al. |
| 2003/0093045 A1 | 5/2003 | Erdman |
| 2003/0114811 A1 | 6/2003 | Christon et al. |
| 2003/0114812 A1 | 6/2003 | Braverman et al. |
| 2003/0114819 A1 | 6/2003 | Sayama et al. |
| 2003/0125687 A1 | 7/2003 | Gubernick et al. |
| 2003/0130638 A1 | 7/2003 | Baker |
| 2003/0158532 A1 | 8/2003 | Magee |
| 2003/0167043 A1 | 9/2003 | Roe et al. |
| 2003/0225384 A1 | 12/2003 | Zenker et al. |
| 2004/0102752 A1 | 5/2004 | Chen |
| 2004/0127872 A1 | 7/2004 | Petryk |
| 2004/0127883 A1 | 7/2004 | Cowell |
| 2004/0162536 A1 | 8/2004 | Becker |
| 2004/0229008 A1 | 11/2004 | Hoying |
| 2004/0265544 A1 | 12/2004 | Di Salvo et al. |
| 2005/0004548 A1 | 1/2005 | Otsubo et al. |
| 2005/0064136 A1 | 3/2005 | Turner et al. |
| 2005/0074584 A1 | 4/2005 | Zehner et al. |
| 2005/0113791 A1 | 5/2005 | Neubauer et al. |
| 2005/0116976 A1 | 6/2005 | Salacz et al. |
| 2005/0119631 A1 | 6/2005 | Giloh et al. |
| 2005/0124953 A1* | 6/2005 | Woltman ............... A61F 13/532 |
| | | 604/385.01 |
| 2005/0137544 A1 | 6/2005 | Schroeder et al. |
| 2005/0148258 A1 | 7/2005 | Chakravarty et al. |
| 2005/0203477 A1 | 9/2005 | Mishima et al. |
| 2005/0228358 A1 | 10/2005 | Mishima et al. |
| 2006/0069371 A1* | 3/2006 | Ohashi ................. A61F 13/4704 |
| | | 604/385.01 |
| 2006/0135920 A1 | 6/2006 | Virgilio et al. |
| 2006/0135934 A1 | 6/2006 | Gilbert |
| 2006/0142724 A1 | 6/2006 | Watanabe et al. |
| 2006/0161122 A1 | 7/2006 | Erdman et al. |
| 2006/0178650 A1 | 8/2006 | Hakansson et al. |
| 2006/0184151 A1 | 8/2006 | Onishi et al. |
| 2006/0241557 A1 | 10/2006 | Moriya |
| 2007/0005038 A1 | 1/2007 | Mansfield et al. |
| 2007/0073253 A1 | 3/2007 | Miyama et al. |
| 2007/0088302 A1 | 4/2007 | Sugiyama et al. |
| 2007/0088305 A1 | 4/2007 | Sakano et al. |
| 2007/0088308 A1 | 4/2007 | Ehrnsperger et al. |
| 2007/0088309 A1 | 4/2007 | Ehrnsperger et al. |
| 2007/0100307 A1 | 5/2007 | Nomoto et al. |
| 2007/0219515 A1 | 9/2007 | Marsh |
| 2007/0255247 A1 | 11/2007 | Moberg-Alehammar et al. |
| 2007/0282288 A1 | 12/2007 | Noda et al. |
| 2008/0119810 A1 | 5/2008 | Kuroda et al. |
| 2008/0208153 A1 | 8/2008 | Oetjen et al. |
| 2008/0249494 A1 | 10/2008 | Digiacomantonio |
| 2008/0281287 A1 | 11/2008 | Marcel et al. |
| 2008/0287903 A1 | 11/2008 | Vega |
| 2008/0294138 A1 | 11/2008 | Andersson et al. |
| 2009/0018519 A1 | 1/2009 | Yoshida |
| 2009/0026651 A1 | 1/2009 | Lee et al. |
| 2009/0030390 A1 | 1/2009 | Hammons et al. |
| 2009/0030391 A1 | 1/2009 | Hammons et al. |
| 2009/0240225 A1 | 9/2009 | Noda et al. |
| 2009/0247978 A1 | 10/2009 | Boissier et al. |
| 2009/0270825 A1 | 10/2009 | Wciork et al. |
| 2009/0281515 A1 | 11/2009 | Noda et al. |
| 2009/0306614 A1 | 12/2009 | Boissier |
| 2009/0306615 A1 | 12/2009 | Olsson |
| 2010/0004615 A1 | 1/2010 | Boissier |
| 2010/0010464 A1 | 1/2010 | Nishitani et al. |
| 2010/0035014 A1 | 2/2010 | Hammons et al. |
| 2010/0036338 A1 | 2/2010 | Hammons et al. |
| 2010/0036339 A1 | 2/2010 | Hammons et al. |
| 2010/0036346 A1 | 2/2010 | Hammons et al. |
| 2010/0036347 A1 | 2/2010 | Hammons et al. |
| 2010/0036349 A1 | 2/2010 | Hammons et al. |
| 2010/0036352 A1 | 2/2010 | Hood et al. |
| 2010/0100067 A1 | 4/2010 | Pugliese, III |
| 2010/0121294 A1 | 5/2010 | Okawa et al. |
| 2010/0130952 A1 | 5/2010 | Mura |
| 2010/0168707 A1 | 7/2010 | Nishikawa et al. |
| 2010/0174261 A1 | 7/2010 | Nomoto et al. |
| 2010/0222759 A1* | 9/2010 | Hammons ........... A61F 13/8405 |
| | | 604/367 |
| 2010/0255258 A1 | 10/2010 | Curro et al. |
| 2010/0274210 A1 | 10/2010 | Noda et al. |
| 2010/0310810 A1 | 12/2010 | Bond et al. |
| 2010/0310837 A1 | 12/2010 | Bond et al. |
| 2010/0310845 A1 | 12/2010 | Bond et al. |
| 2010/0312208 A1 | 12/2010 | Bond et al. |
| 2010/0312212 A1 | 12/2010 | Bond et al. |
| 2011/0037938 A1 | 2/2011 | Raynes et al. |
| 2011/0046596 A1 | 2/2011 | Kudo et al. |
| 2011/0060303 A1 | 3/2011 | Bissah et al. |
| 2011/0071486 A1 | 3/2011 | Harada et al. |
| 2011/0073513 A1 | 3/2011 | Weisman et al. |
| 2011/0087185 A1 | 4/2011 | Wöhlke et al. |
| 2011/0094669 A1 | 4/2011 | Oetjen |
| 2011/0094674 A1 | 4/2011 | Oetjen |
| 2011/0125120 A1 | 5/2011 | Nishitani et al. |
| 2011/0137276 A1 | 6/2011 | Yoshikawa |
| 2011/0137624 A1 | 6/2011 | Weisman |

(56) References Cited

U.S. PATENT DOCUMENTS

| | | |
|---|---|---|
| 2011/0172623 A1 | 7/2011 | Roe et al. |
| 2011/0196330 A1 | 8/2011 | Hammons et al. |
| 2011/0206904 A1 | 8/2011 | Heilman et al. |
| 2011/0282314 A1 | 11/2011 | Hammons |
| 2011/0313385 A1 | 12/2011 | Hammons et al. |
| 2012/0035566 A1 | 2/2012 | Sagisaka et al. |
| 2012/0049404 A1 | 3/2012 | Gibson et al. |
| 2012/0078209 A1 | 3/2012 | Sakai et al. |
| 2012/0095424 A1 | 4/2012 | Komatsu et al. |
| 2012/0095425 A1 | 4/2012 | Nishitani et al. |
| 2012/0095426 A1 | 4/2012 | Visscher et al. |
| 2012/0164368 A1 | 6/2012 | Curro et al. |
| 2012/0226255 A1 | 9/2012 | Mariko et al. |
| 2012/0273990 A1 | 11/2012 | O'Donnell et al. |
| 2012/0273997 A1 | 11/2012 | Stone et al. |
| 2012/0316529 A1 | 12/2012 | Kruezer et al. |
| 2013/0060218 A1 | 3/2013 | Kudo et al. |
| 2013/0079742 A1 | 3/2013 | Seiichi et al. |
| 2013/0158497 A1 | 6/2013 | Yamaguchi et al. |
| 2013/0317470 A1 | 11/2013 | Nobuyuki et al. |
| 2014/0031779 A1 | 1/2014 | Hammons et al. |
| 2014/0052088 A1 | 2/2014 | Weisman et al. |
| 2014/0228796 A1 | 8/2014 | Burvall et al. |
| 2014/0296809 A1 | 10/2014 | Hammons et al. |
| 2015/0038933 A1 | 2/2015 | Lee et al. |
| 2015/0038934 A1 | 2/2015 | Lee et al. |
| 2015/0282998 A1 | 10/2015 | Arizti |
| 2015/0282999 A1 | 10/2015 | Arizti |
| 2017/0290715 A1 | 10/2017 | Arizti et al. |

FOREIGN PATENT DOCUMENTS

| | | |
|---|---|---|
| CN | 2827323 | 10/2006 |
| CN | 201263750 | 7/2009 |
| CN | 202235945 | 5/2012 |
| CN | 203988677 | 12/2014 |
| EP | 0432882 | 6/1991 |
| EP | 0585904 | 3/1994 |
| EP | 626160 | 11/1994 |
| EP | 1124522 | 8/2001 |
| EP | 1030636 | 3/2003 |
| EP | 1371379 | 12/2003 |
| EP | 1206926 | 7/2009 |
| EP | 2656826 | 10/2013 |
| GB | 2262906 | 7/1993 |
| GB | 2383957 | 7/2003 |
| IN | 635/KOL/2001 | 3/2006 |
| IN | 2790/DEL/1998 | 8/2008 |
| IN | 980/MUM/2009 | 6/2009 |
| JP | H10-080968 | 3/1998 |
| JP | 2001037810 | 2/2001 |
| JP | 2001120597 | 5/2001 |
| JP | 2002325794 | 11/2002 |
| JP | 2003275237 | 9/2003 |
| JP | 2004089269 | 3/2004 |
| JP | 2004298454 | 10/2004 |
| JP | 2005312547 | 11/2005 |
| JP | 2006102001 | 4/2006 |
| JP | D1281004 | 7/2006 |
| JP | 2006346021 | 12/2006 |
| JP | 2007089906 | 4/2007 |
| JP | 2007105298 | 4/2007 |
| JP | 2007105299 | 4/2007 |
| JP | 2007105303 | 4/2007 |
| JP | 2007167453 | 7/2007 |
| JP | 2007190315 | 8/2007 |
| JP | 2007202691 | 8/2007 |
| JP | 2007202701 | 8/2007 |
| JP | 2007209518 | 8/2007 |
| JP | 2008079747 | 4/2008 |
| JP | 2008086428 | 4/2008 |
| JP | 2008272269 | 11/2008 |
| JP | 2009045333 | 3/2009 |
| JP | 2009050621 | 3/2009 |
| JP | 2009101091 | 5/2009 |
| JP | 2009112590 | 5/2009 |
| JP | 2009125199 | 6/2009 |
| JP | 2009125200 | 6/2009 |
| JP | 2009125203 | 6/2009 |
| JP | 2009136601 | 6/2009 |
| JP | 2009148425 | 7/2009 |
| JP | 2009178384 | 8/2009 |
| JP | 2009178422 | 8/2009 |
| JP | 2009195303 | 9/2009 |
| JP | 2009219744 | 10/2009 |
| JP | 2009240416 | 10/2009 |
| JP | 2010022560 | 2/2010 |
| JP | 2010131206 | 6/2010 |
| JP | 2010201093 | 9/2010 |
| JP | 2010221067 | 10/2010 |
| JP | 2011030700 | 2/2011 |
| JP | 2011239858 | 2/2011 |
| JP | 2011104014 | 6/2011 |
| JP | 2011125537 | 6/2011 |
| JP | 2011156254 | 8/2011 |
| JP | 2012070867 | 4/2012 |
| KR | 20010024622 | 3/2001 |
| KR | 20010113258 | 12/2001 |
| KR | 20020035634 | 5/2002 |
| KR | 20040022412 | 3/2004 |
| KR | 20050092868 | 9/2005 |
| KR | 100639632 | 10/2006 |
| SE | 520458 | 7/2003 |
| WO | WO-1996/029037 | 9/1996 |
| WO | WO-1999/025294 | 5/1999 |
| WO | WO9925287 | 5/1999 |
| WO | WO-2000/028929 | 5/2000 |
| WO | WO-2000/069483 | 11/2000 |
| WO | WO-2003/015681 | 2/2003 |
| WO | WO-2006/047282 | 5/2006 |
| WO | WO-2006/134906 | 12/2006 |
| WO | WO-2008/093659 | 8/2008 |
| WO | WO-2010/109992 | 9/2010 |
| WO | WO-2010/131548 | 11/2010 |
| WO | WO-2011/053044 | 5/2011 |
| WO | WO-2012/052172 | 4/2012 |

OTHER PUBLICATIONS

International Search Report and Written Opinion, PCT/US2015/020498, dated May 28, 2015.
Office Actions for U.S. Appl. No. 14/656,820.
Office Actions for U.S. Appl. No. 15/590,037.

* cited by examiner

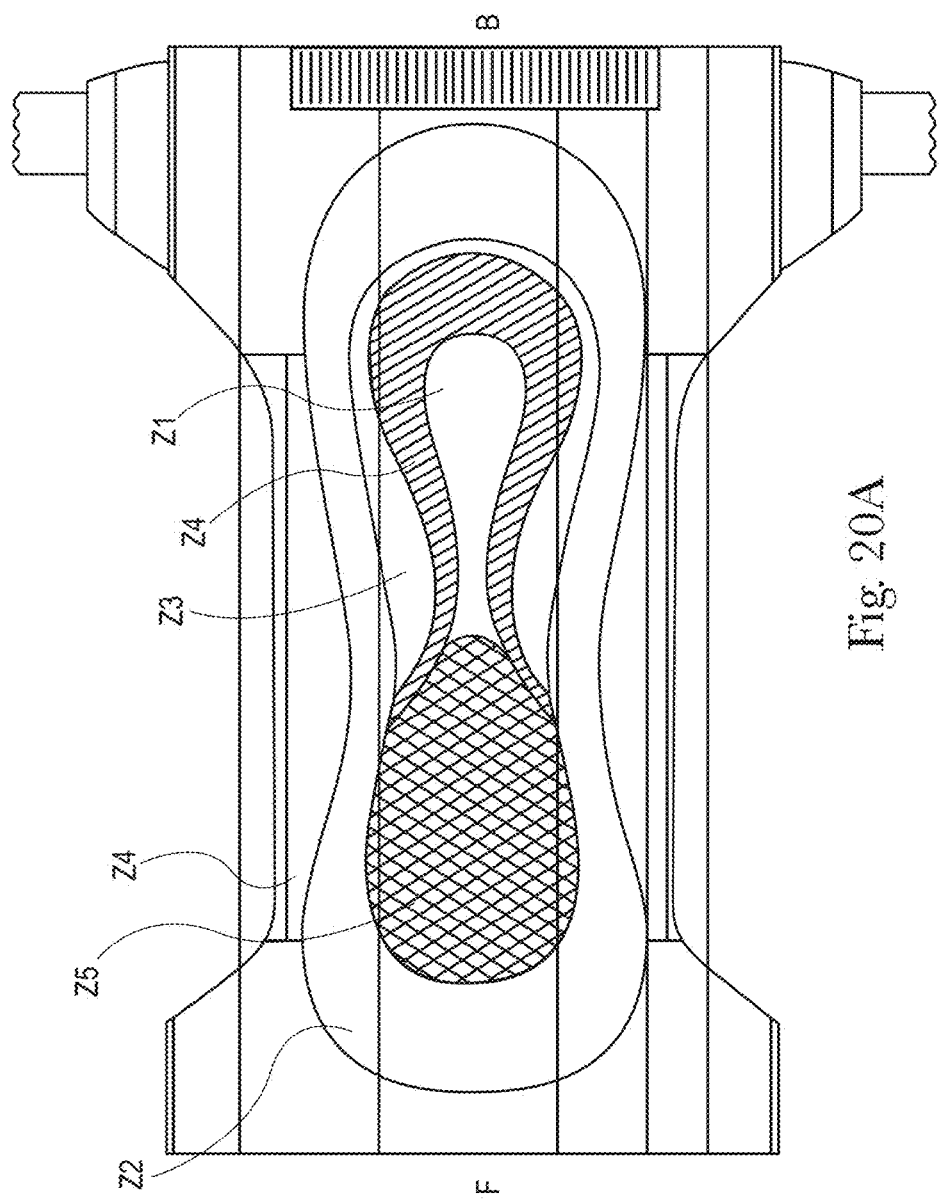

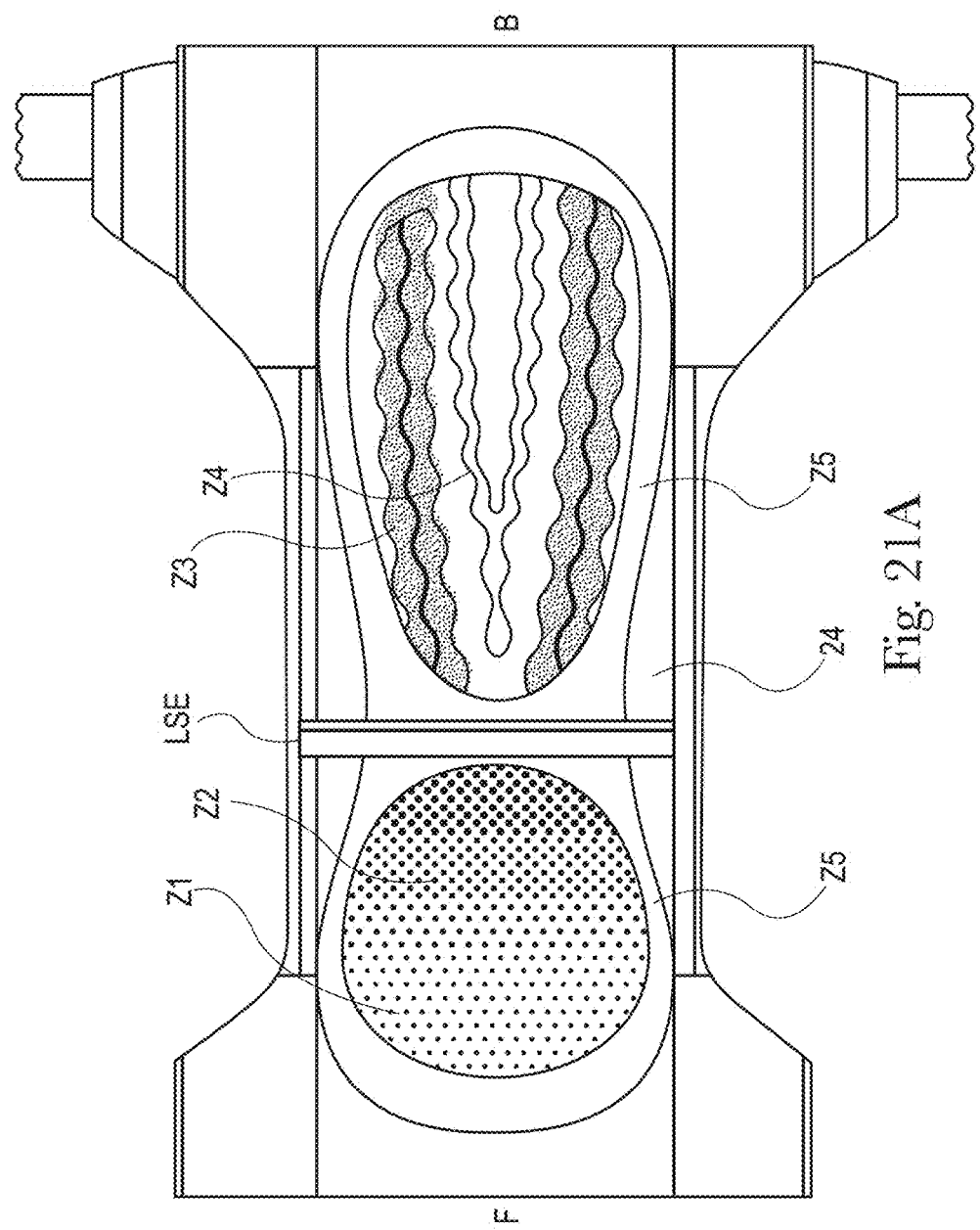

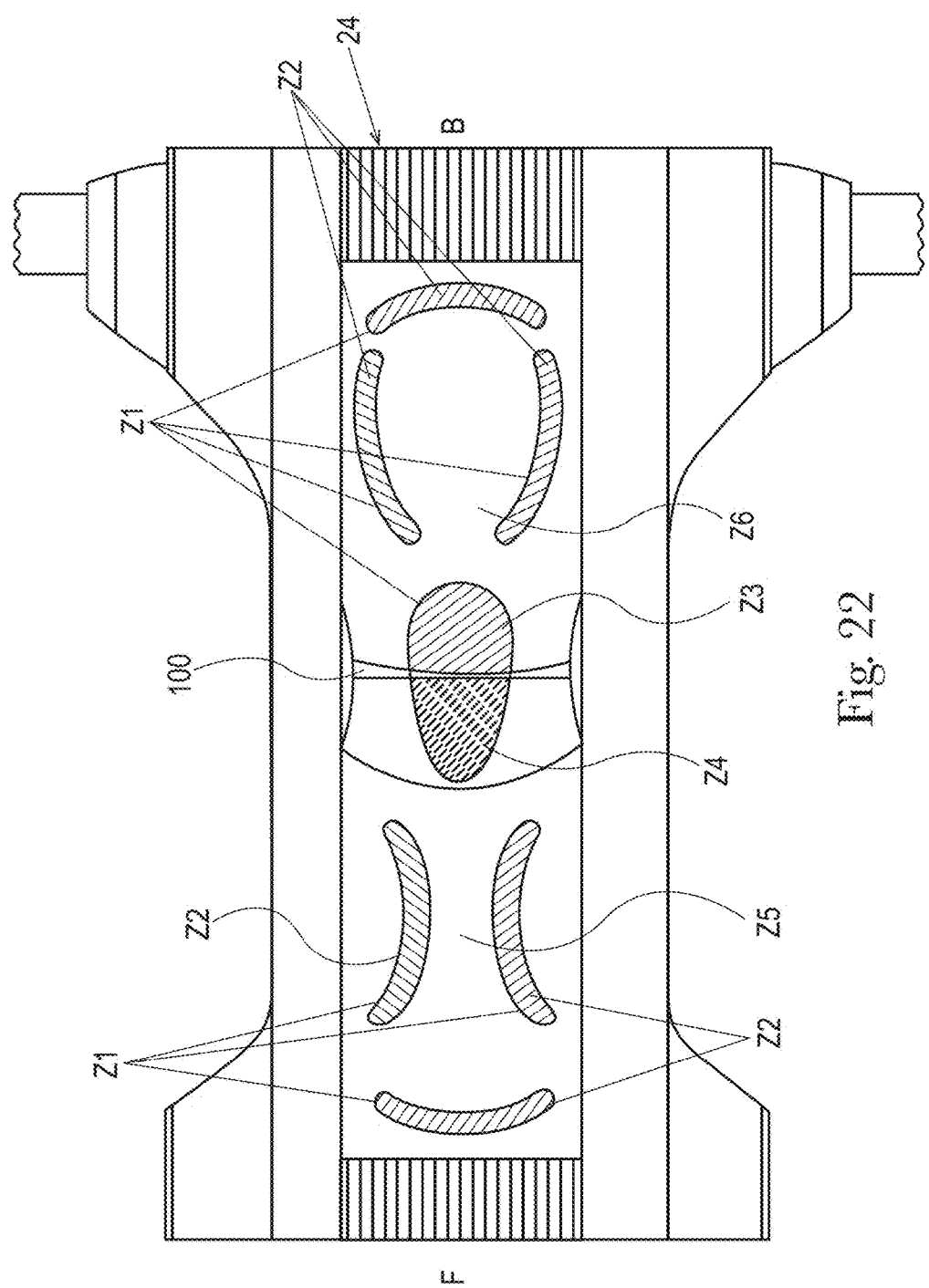

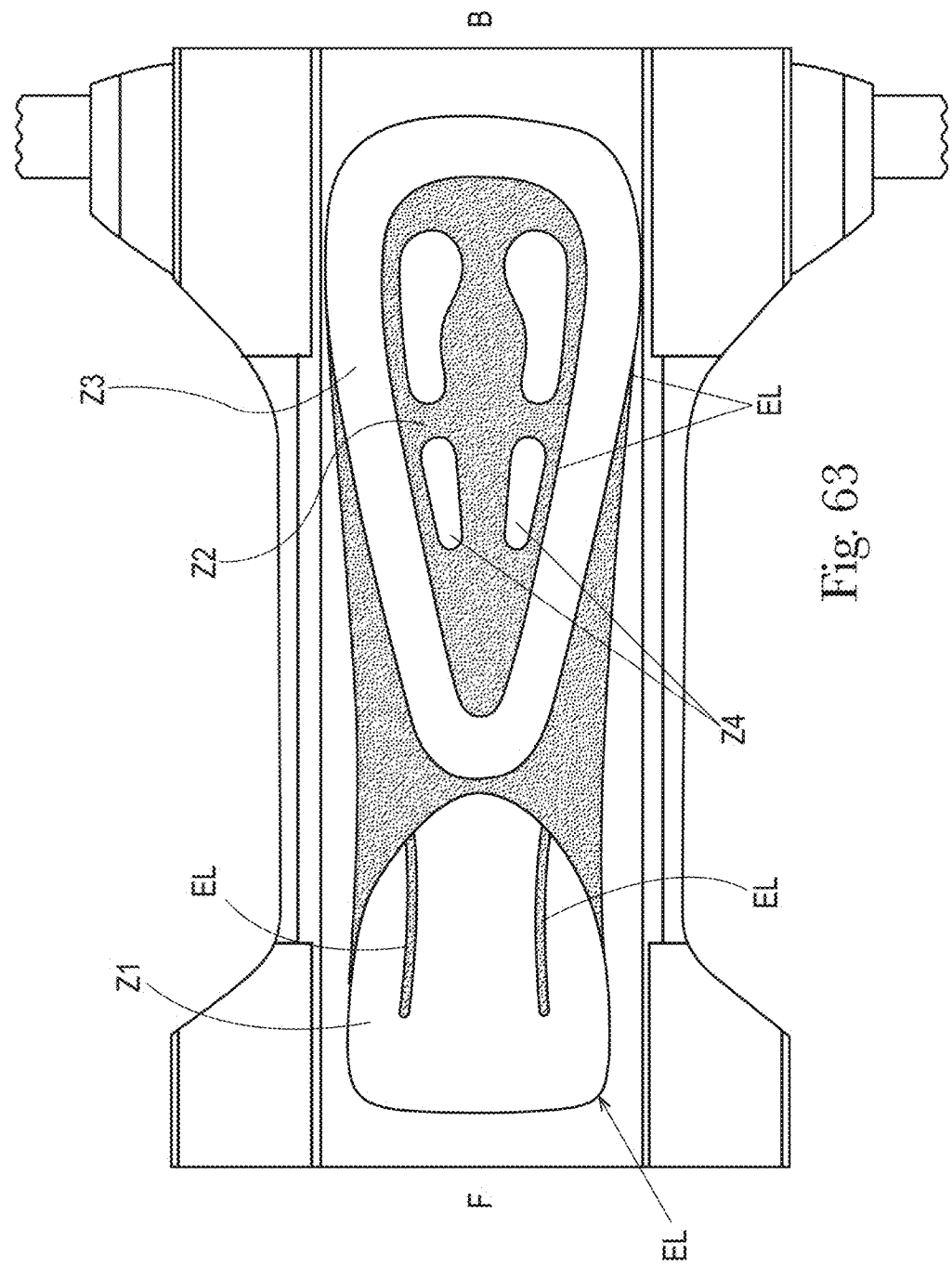

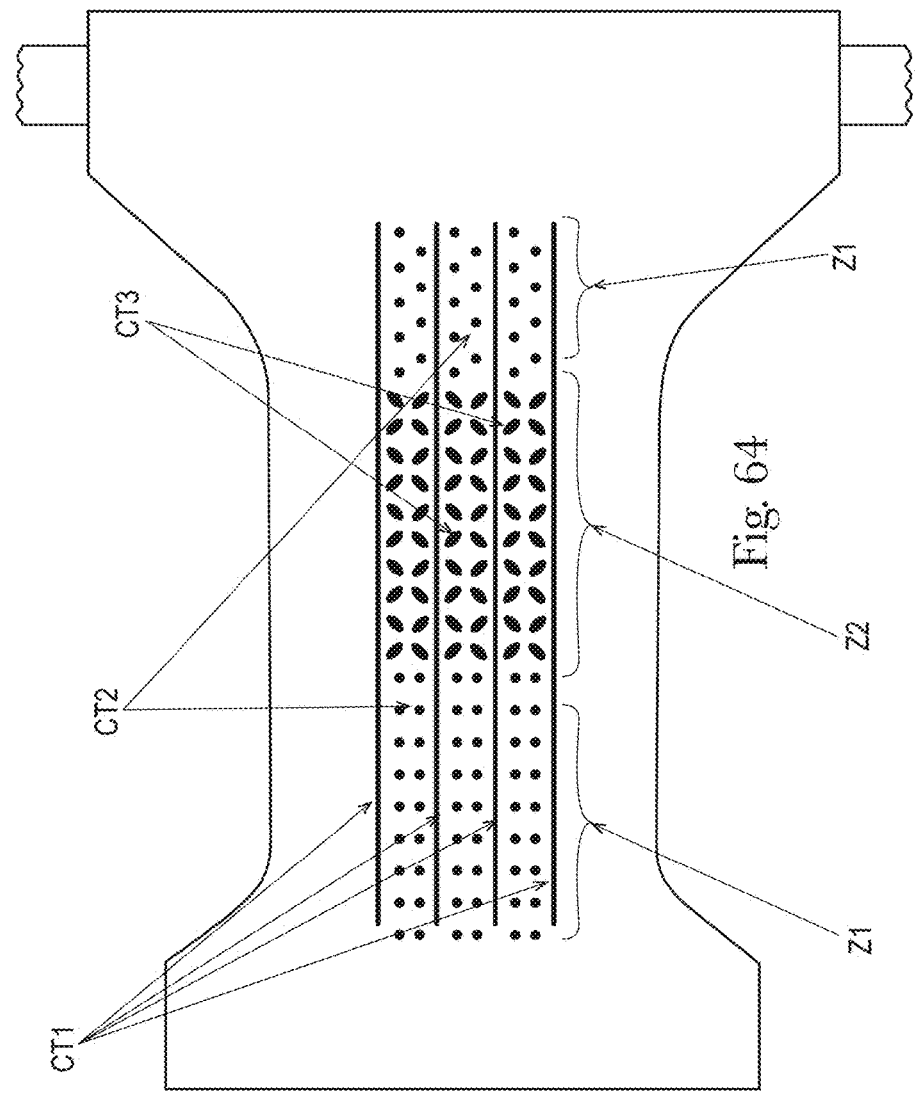

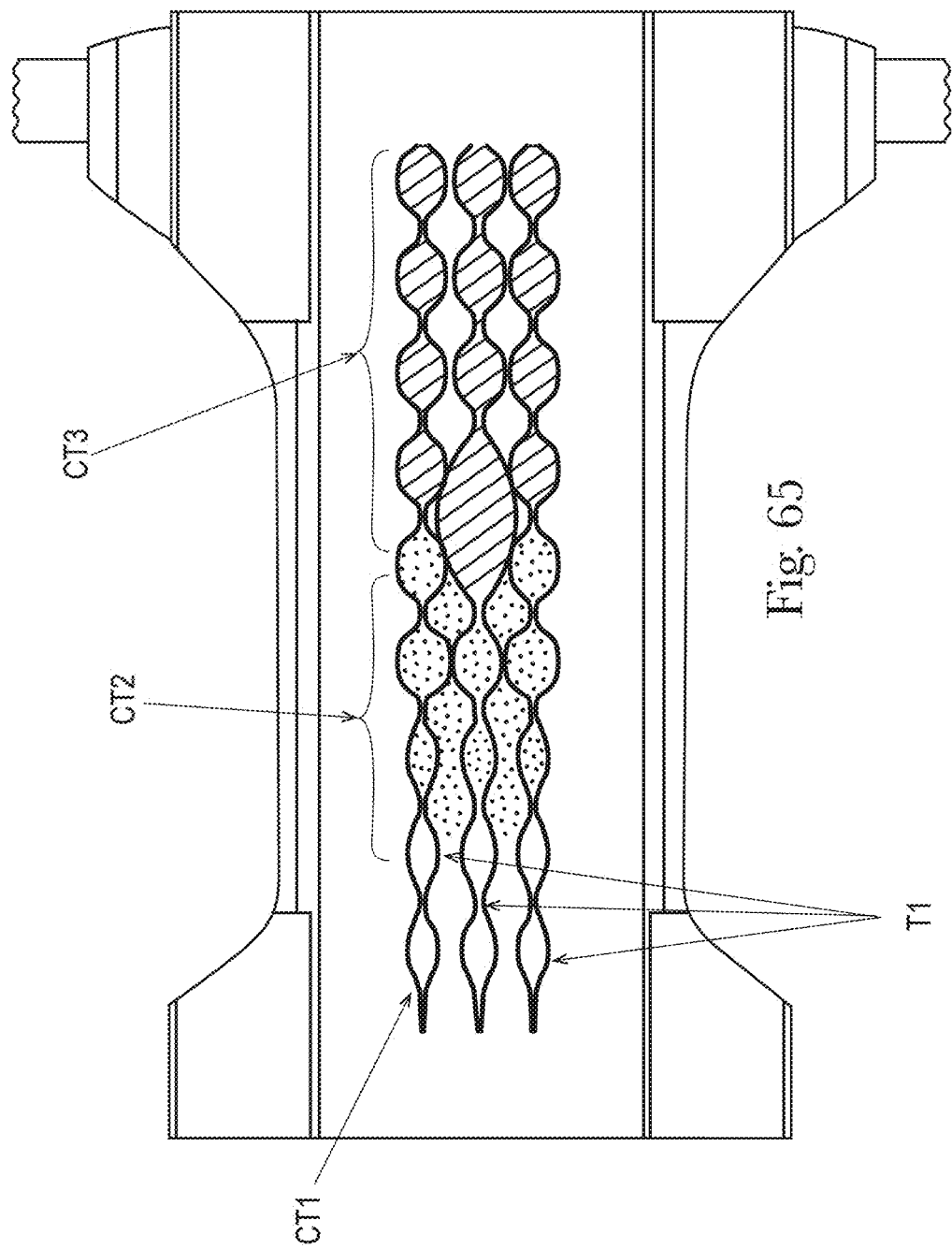

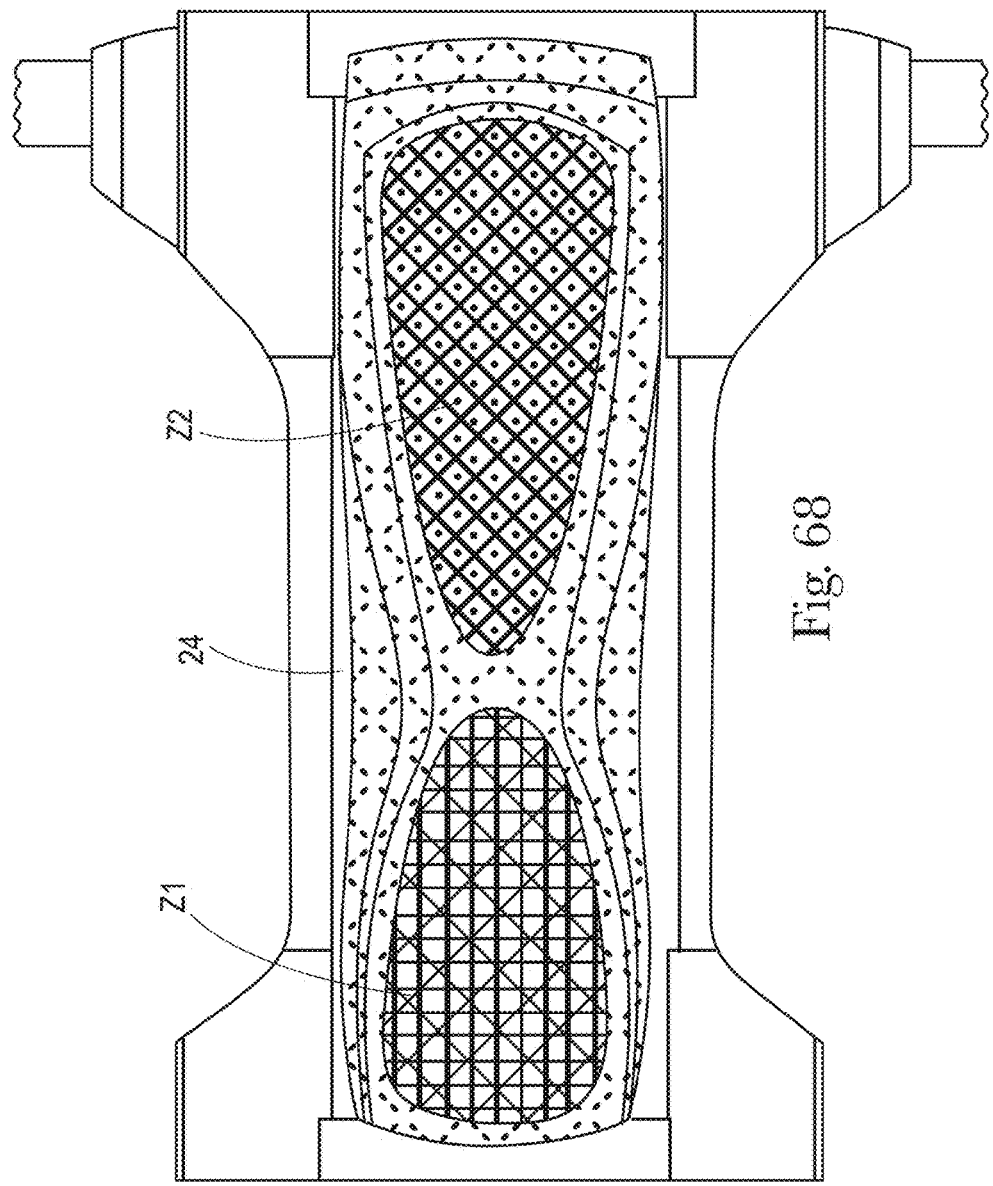

ABSORBENT ARTICLES HAVING SUBSTRATES HAVING ZONAL TREATMENTS

FIELD

The present disclosure is generally directed to absorbent articles for personal hygiene. The absorbent articles may each comprises one or more substrates comprising zones having the same or different treatments.

BACKGROUND

Absorbent articles for personal hygiene are designed to absorb and contain bodily exudates (e.g., urine, bowel movements "BM"). These absorbent articles may comprise several layers providing different functions, for example, a topsheet, a backsheet, and an absorbent core disposed between the topsheet and the backsheet, among other layers.

The function of the absorbent core is to absorb and retain the bodily exudates for a prolonged amount of time, for example, overnight for a diaper, minimize re-wet to keep the wearer dry, and avoid soiling of clothes or bed sheets. Some currently marketed absorbent articles comprise absorbent cores comprising an absorbent material which is a blend of comminuted wood pulp (i.e., airfelt) with superabsorbent polymers ("SAP") in particulate form, also known as absorbent gelling materials ("AGM"). Other absorbent articles have an absorbent core consisting essentially of SAP as the absorbent material and one or more hotmelt adhesives (so called "airfelt-free" cores).

Absorbent articles may also comprise a liquid management system ("LMS") that may have an acquisition layer and/or a distribution layer. Some absorbent articles may comprise leg cuffs and waist bands which provide improved containment of liquids and other bodily exudates. Usually, each leg cuff comprises one or more elastic strands or elements comprised in the chassis of the diaper, for example, between the topsheet and backsheet in the area of the leg openings to provide an effective seal while the absorbent article is in use. These elasticized elements which may be substantially planar with the chassis of the absorbent article will be referred to herein as gasketing cuffs. It is also usual for the leg cuffs to comprise raised elasticized flaps, herein referred to as barrier leg cuffs, which improve the containment of fluid in the leg-torso joint regions.

Absorbent articles, such as diapers (taped or pants) or adult incontinence products, appear to have a shortcoming in their topsheets and/or their LMS in that the front and back regions, or other regions, are not specifically designed for their intended use in either function or appearance. Most commercial diapers or adult incontinence products include topsheets and/or acquisition layers that have zero features (regular nonwoven material) or one feature, such as apertures or embossments, for example, throughout the entire topsheet or LMS. The embossments or apertures are typically the same size and shape (same appearance as well) in the front and the back regions and, therefore, do not provide specific configurations for urine management compared to BM management or do not provide specific configurations that give the appearance of urine management compared to the appearance of BM management. This can be problematic in that urine management should be treated much differently than BM management to achieve an improved diaper owing to the fact that BM and urine have significant differences in rheology and solids content. It is not a one-size-fits-all situation. In view of the foregoing, topsheets and/or LMSs of absorbent articles should be improved to provide more zonal treatments or features that handle, or give the appearance of handling, urine management and BM management differently.

In addition to the above, typical absorbent articles need improved systems of handling bodily exudates once the bodily exudates are received by the topsheet. In general, some absorbent articles acquire bodily exudates too quickly or too slowly and other absorbent articles may leak because of the bodily exudates not be absorbed, or fully or properly absorbed, into the core. As such, it may be beneficial for topsheets and/or LMSs to have features that direct or alter (e.g., slow, hasten, restrict, channel) the flow of bodily exudates into, over, and/or through the topsheets and/or LMSs. This may be desirable to achieve better bodily exudate (e.g., urine) distribution into an absorbent core, for example. As a further example, this may further be desirable to achieve reduced leakage by maintaining the bodily exudates over a portion of the absorbent core for a suitable period of time so that they can be fully and properly absorbed by the core. In view of the foregoing, topsheets or LMSs should be improved to provide for better bodily exudate management.

SUMMARY

In one form, the present disclosure is directed, in part, to an absorbent article comprising a liquid permeable topsheet, a liquid impermeable backsheet, and an absorbent core positioned at least partially intermediate the liquid permeable topsheet and the liquid impermeable backsheet. The absorbent article may comprise a substantially laterally-extending separation element defining a visual front portion and a visual back portion on a wearer-facing surface of the absorbent article. The liquid permeable topsheet may comprise a first zone in the visual front portion that comprises a first geometric treatment and a second zone in the visual back portion that comprises a second geometric treatment.

In one form, the present disclosure is directed, in part, to an absorbent article comprising a liquid permeable topsheet, a liquid impermeable backsheet, and an absorbent core positioned at least partially intermediate the liquid permeable topsheet and the liquid impermeable backsheet. The absorbent article comprises a lateral axis defining a front region and a back region. The liquid permeable topsheet comprises a first zone at least partially in the front region. The first zone may comprise a first morphological treatment configured for urine handling. The liquid permeable topsheet comprises a second zone at least partially in the back region. The second zone may comprise a second morphological treatment configured for BM handling. A pattern of the first morphological treatment in the first zone may be nonsymmetrical to, or symmetrical to, a pattern of the second morphological treatment in the second zone about the lateral axis.

In one form, the present disclosure is directed, in part, to an absorbent article comprising a liquid permeable topsheet, a liquid impermeable backsheet, a lateral axis, and an absorbent core positioned at least partially intermediate the liquid permeable topsheet and the liquid impermeable backsheet. The liquid permeable topsheet comprises a first zone at least partially positioned on a first side of the lateral axis and a second zone at least partially positioned on a second side of the lateral axis. The first zone may have apertures defined therein having an effective aperture area in the range of about 0.2 mm$^2$ to about 15 mm$^2$ according to the Aperture Test. The first zone may have a % effective open area of about 15% to about 40% according to the Aperture Test. The second zone may have apertures defined therein having an effective aperture area in the range of about 0.05 mm$^2$ to about 2 mm$^2$ according to the Aperture Test. The second zone may have a % effective open area of about 2% to about 15% according to the Aperture Test. The apertures in the first zone may be at least about 25% larger than the apertures in the second zone.

In one form, the present disclosure is directed, in part, to absorbent article comprising a liquid permeable topsheet, a liquid impermeable backsheet, a lateral axis defining a front region on a first side of the lateral axis and a back region on a second side of the lateral axis, and an absorbent core positioned at least partially intermediate the liquid permeable topsheet and the liquid impermeable backsheet. The liquid permeable topsheet may comprise a first zone situated primarily in the front region and having a substantially transferrable chemical treatment and a second zone situated primarily in the back region and having the substantially transferrable chemical treatment. A basis weight of the substantially transferrable chemical treatment may be greater in the second zone than in the first zone.

In one form, the present disclosure is directed, in part, to an absorbent article comprising a liquid permeable topsheet, a liquid impermeable backsheet, a laterally-extending separation element defining a front region on a first side of the separation element and a back region on a second side of the separation element, and an absorbent core positioned at least partially intermediate the liquid permeable topsheet and the liquid impermeable backsheet. The liquid permeable topsheet may comprise a first zone situated primarily in the front region and having a first substantially transferrable chemical treatment that may be hydrophobic and a second zone situated primarily in the back region and having a second substantially transferrable chemical treatment that may have a different hydrophilicity as the first chemical treatment.

In one form, the present disclosure is directed, in part, to an absorbent article comprising a liquid permeable topsheet, a liquid impermeable backsheet, a liquid management system, and an absorbent core positioned at least partially intermediate the liquid management system and the liquid impermeable backsheet. The liquid management system is positioned at least partially intermediate the liquid permeable topsheet and the absorbent core. The liquid permeable topsheet and the liquid management system may comprise a first zone on a first side of a lateral axis of the absorbent article and a second zone on a second side of the lateral axis. Portions of the liquid management system may extend into or through portions of the liquid impermeable topsheet or portions of the liquid impermeable topsheet may extend into or through portions of the liquid management system in the first zone. Portions of the liquid management system may extend into or through portions of the liquid impermeable topsheet or portions of the liquid impermeable topsheet may extend into or through portions of the liquid management system in the second zone. The first zone or the second zone may comprise a substantially transferrable chemical treatment.

In one form, the present disclosure is directed, in part, to an absorbent article comprising a liquid permeable topsheet, a liquid impermeable backsheet, and an absorbent core positioned at least partially intermediate the liquid permeable topsheet and the liquid impermeable backsheet. The liquid permeable topsheet may comprise a flow control material. The flow control material may form an at least mostly enclosed perimeter over at least a portion of the absorbent core. The flow control material may extend less than 0.2 mm outwardly from the liquid permeable topsheet, measured according to the Flow Control Material Outward Extension Method herein, and may penetrate a portion of the liquid permeable topsheet.

In one form, the present disclosure is directed, in part, to an absorbent article comprising a liquid permeable topsheet, a liquid impermeable backsheet, a lateral axis defining a front region of the absorbent article on a first side of the lateral axis and a back region of the absorbent article on a second side of the lateral axis, and an absorbent core positioned at least partially intermediate the liquid permeable topsheet and the liquid impermeable backsheet. The liquid permeable topsheet may comprise a first zone situated primarily in the front region and comprising a first flow control material and a second zone situated primarily in the back region and comprising a second flow control material. The first flow control material may be different than the second flow control material.

In one form, the present disclosure is directed, in part, to an absorbent article comprising a liquid permeable topsheet, a liquid impermeable backsheet, a liquid management system, and an absorbent core positioned at least partially intermediate the liquid management system and the liquid impermeable backsheet. The liquid management system is positioned at least partially intermediate the liquid permeable topsheet and the absorbent core. The liquid permeable topsheet or the liquid management system may comprise a flow control material positioned in or surrounding a urine or feces insult zone.

BRIEF DESCRIPTION OF THE DRAWINGS

The above-mentioned and other features and advantages of the present disclosure, and the manner of attaining them, will become more apparent and the disclosure itself will be better understood by reference to the following description of non-limiting examples of the disclosure taken in conjunction with the accompanying drawings, wherein:

FIG. 22 is an example of a topsheet (and LMS if interpenetrating the topsheet) having six zones, each zone having one or more treatments or no treatments, in accordance with the present disclosure;

FIGS. 63-68 are illustrations of example absorbent articles having various zones with various treatments in accordance with the present disclosure.

DETAILED DESCRIPTION

Figure 1:
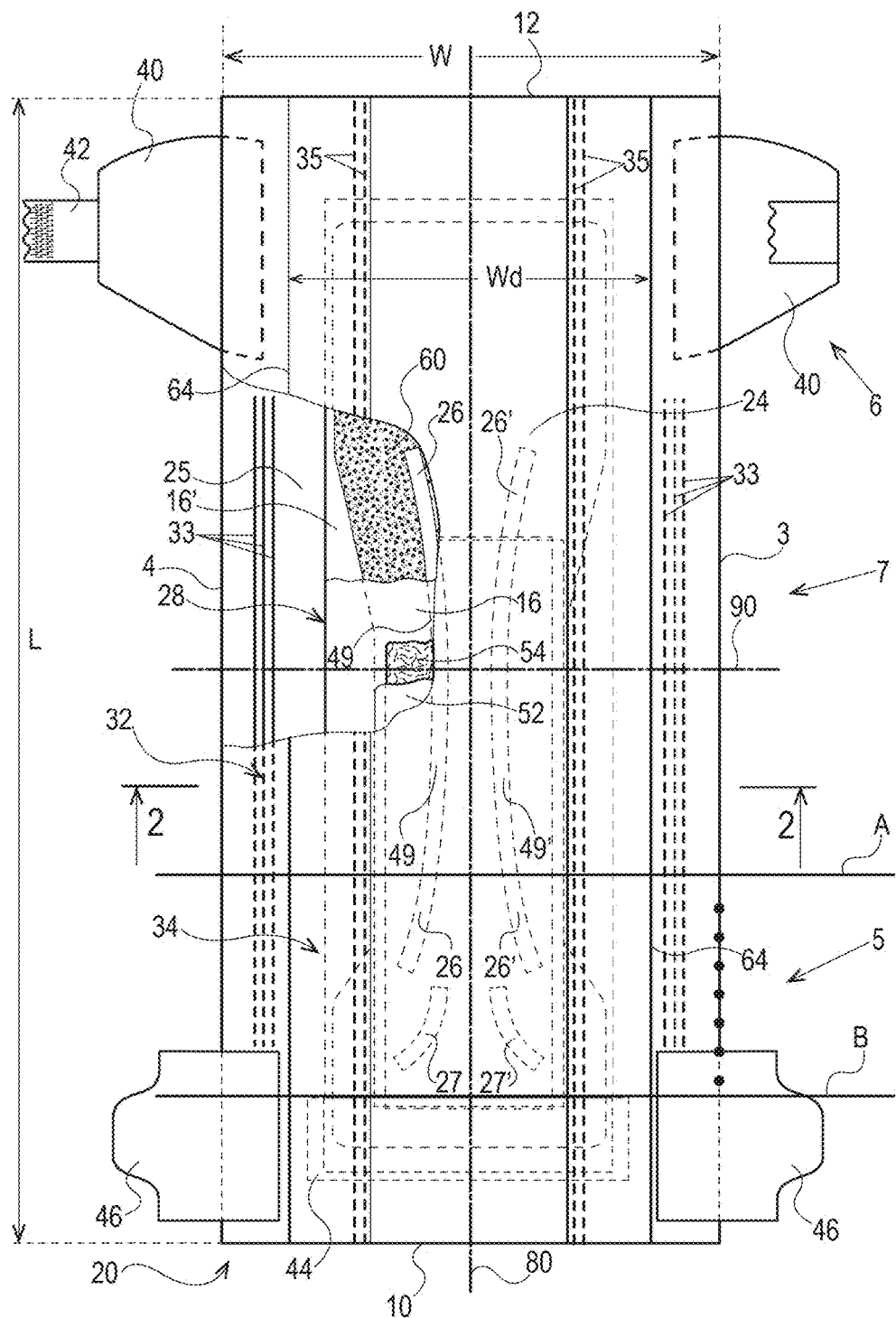
FIG. 1 is a top view of an absorbent article with some layers partially removed in accordance with the present disclosure.

Various non-limiting embodiments of the present disclosure will now be described to provide an overall understanding of the principles of the structure, function, manufacture, and use of the absorbent articles comprising substrates comprising zonal treatments disclosed herein. One or more examples of these non-limiting embodiments are illustrated in the accompanying drawings. Those of ordinary skill in the art will understand that the absorbent articles comprising substrates comprising zonal treatments described herein and illustrated in the accompanying drawings are non-limiting example embodiments and that the scope of the various non-limiting embodiments of the present disclosure are defined solely by the claims. The features illustrated or described in connection with one non-limiting embodiment may be combined with the features of other non-limiting embodiments. Such modifications and variations are intended to be included within the scope of the present disclosure.

Introduction

The term "absorbent article, as used herein, refers to disposable devices such as infant, child, or adult diapers, adult incontinence products, pant-style diapers, training pants, diaper inserts, and the like which are placed against or in proximity to the body of the wearer to absorb and contain the bodily exudates (e.g., urine and BM) discharged from the body. Typically, these articles comprise a topsheet, backsheet, an absorbent core, optionally a LMS, and typically other components, with the absorbent core normally placed at least partially between the backsheet and the LMS (if provided) or between the topsheet and the backsheet. The absorbent articles of the present disclosure will be further illustrated in the below description and in the Figures in the form of a taped diaper. Nothing in this description should be, however, considered to limit the scope of the claims. As such the present disclosure applies to any suitable form of absorbent articles (e.g., training pants, taped diapers, adult incontinence products-in either taped or pant forms).

The term "nonwoven web", as used herein, means a manufactured sheet, web, or batt of directionally or randomly orientated fibers, bonded by friction, and/or cohesion, and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers may have diameters ranging from less than about 0.001 mm to more than about 0.2 mm and may come in several different forms such as short fibers (known as staple, or chopped), continuous single fibers (filaments or monofilaments), untwisted bundles of continuous filaments (tow), and twisted bundles of continuous filaments (yam). Nonwoven webs can be formed by many processes such as meltblowing, spunbonding, solvent spinning, electrospinning, carding, and airlaying. The basis weight of nonwoven webs is usually expressed in grams per square meter (g/m$^2$ or gsm).

The terms "joined" or "bonded" or "attached", as used herein, encompasses configurations whereby an element is directly secured to another element by affixing the element directly to the other element, and configurations whereby an element is indirectly secured to another element by affixing the element to intermediate member(s) which in turn are affixed to the other element.

The term "channel", as used herein, is a region or zone in a material layer that has a substantially lower basis weight (e.g., less than 50%, less than 70%, less than 90%) than the surrounding material in the material layer. The channel may be a region in a material layer that is substantially material-free (e.g., 90% material-free, 95% material-free, or 99% material-free, or completely material-free). A channel may extend through one or more material layers. The channels generally have a lower bending modulus than the surrounding regions of the material layer, enabling the material layer to bend more easily and/or contain more bodily exudates within the channels than in the surrounding areas of the material layer. Thus, a channel is not merely an indentation in the material layer that does not create a reduced basis weight in the material layer in the area of the channel.

The term "geometric treatment", as used herein, means at least a portion or region of a single or multi-layer substrate that comprises elements that are apertures of any suitable size and shape and/or elements that form a morphological treatment.

The term "morphological treatment", as used herein, means at least a portion or region of a single or multi-layer substrate that comprises elements having three-dimensional features, embossments, interpenetration of one layer into or through another layer (e.g., one or more layers of the LMS into the topsheet or the topsheet into one or more layer of the LMS), out-of-plane bumps, out-of-plane ridges, out-of-plane tufts, out-of-plane pleats, out-of-plane ripples, or fold lines. A morphological treatment causes a substantially uniform planar substrate to be transformed from a first morphological configuration (generally flat and planar) to another morphological configuration (generally not flat and planar). The morphological treatment is formed of a plurality of the elements. For the avoidance of doubt, a morphological treatment does not include apertures, but an apertured material may be subjected to a morphological treatment.

The term "chemical treatment", as used herein, means at least a portion or region of a single or multi-layer substrate that has a compound, composition, or substance applied to at least a portion thereof. Some examples are one or more skin care compositions, surfactants, inks, dyes, pigments, hydrophilic coatings, hydrophobic coatings, lotions, enzyme inhibitors, vitamins, and/or active ingredients. The chemical treatment may be sprayed on, printed on, slot coated, or otherwise applied to the at least a portion or region of the substrate.

The term "substantially durable", as used herein, means a chemical treatment where at least 94%, at least 95%, at least 96%, at least 97%, at least 98%, at least 99%, or more of the applied chemical treatment remains on the substrate from the time of manufacture throughout a typical period of intended use (e.g., from a point in time where an absorbent article is applied to a wearer to a point in time when the absorbent article is removed from the wearer and discarded).

The term "substantially transferrable", as used herein, means a chemical treatment where at least 10%, at least 20%, at least 30%, at least 40%, at least 50%, or even at least 60% or more of the applied chemical treatment transfers to the skin of a wearer during a typical period of intended use (e.g., from a point in time where an absorbent article is applied to a wearer to a point in time when the absorbent article is removed from the wearer and discarded).

The term "hydrophilic coating", as used herein, means a chemical treatment applied to a substrate to cause the substrate to become hydrophilic or more hydrophilic.

The term "hydrophilic", as used herein, refers to a substrate or composition having a contact angle less than or equal to 90° according to The American Chemical Society Publication "Contact Angle, Wettability, and Adhesion," edited by Robert F. Gould and copyrighted in 1964.

The term "hydrophobic coating", as used herein, means a chemical treatment applied to a substrate to cause the substrate to become hydrophobic or more hydrophobic.

The term "hydrophobic", as used herein, refers to a substrate or composition having a contact angle greater than or equal to 90° according to The American Chemical Society Publication "Contact Angle, Wettability, and Adhesion," edited by Robert F. Gould and copyrighted in 1964.

The term "flow control material", as used herein, may be a chemical treatment where a substance is applied to a substrate (such as a liquid permeable topsheet) that at least partially restricts, or fully restricts, the flow of bodily exudates therethrough. The flow control material may be a wax, an ink (having a pigment), a non-tack adhesive, a hot melt adhesive, a substantially durable component of a skin care composition, a polyolefin, a high molecular weight alcohol (one example of a component of a skin care composition), or other compositions substantially solid at 20 degrees C., for example. The flow control material may be substantially durable. The flow control material may also comprise when a material is applied to a substrate (e.g., a topsheet) and then the material and the substrate are run through two or more rolls to melt, join, bond, or attach the flow control material to the substrate.

The term "active ingredient", as used herein, means an ingredient that has a chemical, biochemical, and/or biological effect—i.e., causes, initiates, or affects a change in a chemical, biochemical, and/or biological reaction, system, process, or equilibrium. This is opposed to inactive ingredients which may typically be used as carrier media, viscosity modifiers, melt temperature mediators, or for purely physical reasons (i.e., fillers).

The term "enzyme inhibitor", as used herein, means a molecule, which binds to enzymes and decreases their activity.

General Description of the Substrates Having Zonal Treatments

The absorbent articles of the present disclosure comprise one or more single or multi-layer substrates comprising one or more zones, alternatively two or more zones, alternatively three or more zones, and alternatively four or more zones, and so forth. Each of the zones in the substrates may have different treatments or the same treatments. One or more zones of the substrates may not have a treatment at all. Some of, none of, or all of the zones may comprise flow control materials (can be referred to herein as a "treatment" generally). Each of the zones may have different or the same treatments to better provide for urine management or BM management owing to the fact that the rheology and solids content of BM and urine may be quite different. Alternatively, each of the zones may have different or the same treatments to provide the appearance of better urine or BM management or to provide the caregiver or wearer with clues as to the correct orientation of the absorbent article when donned on the wearer.

The substrates may be, for example, a liquid permeable topsheet, a patch or layer positioned over the liquid permeable topsheet, one or more layers of a LMS, and/or other substrates within an absorbent article. The zones in the substrate or substrates (used interchangeably herein) may be formed at least partially in the front and/or back regions of the absorbent article, in the crotch region of the absorbent article, in regions of the absorbent article on a first and second side of either a lateral or longitudinal axis, in regions of the absorbent article on the same or different side of a substantially laterally-extending separation element, in regions of the absorbent article dispersed throughout other regions of the absorbent article, and/or otherwise dispersed throughout regions of the substrates of the absorbent articles. Each zone in the substrate may have one or more of the same or different geometric treatments, morphological treatments, and/or chemical treatments (together "treatments") as another zone in the substrate. By "the same", it is meant that the treatments are of the same type (e.g., both embossments) and have the same pattern, height, length, width, size, shape, frequency, and other dimension, for example. By "different", it is meant that the treatments may be the same (e.g., both embossments), but the pattern, height, length, width, size, shape, frequency, or other dimension is different. Alternatively, "different" can mean that the treatment is not the same as another treatment (e.g., apertures as one treatment and embossments as another treatment). Although the treatments in this scenario are "different" they may form symmetrical or asymmetrical patterns, or repeating or non-repeating patterns, about a lateral or longitudinal axis or a substantially laterally-extending separation element of an absorbent article. One or more zones in the substrate may overlap with, not overlap with, coincide with, or not coincide with other zones in the substrate. As such, the zones may be separate from each other or may overlap with each other. Any number of zones having the same or different treatments, or no treatments, may be provided in a particular substrate. A substrate may have one or more layers and the various treatments may be provided in one, all, or less than all of the layers.

Before the various zones and treatments and/or flow control material within the zones are discussed, a general discussion of absorbent articles will be presented to frame an example context of the zonal treatments and flow control materials of the present disclosure.

General Description of an Example Absorbent Article

Figure 2:
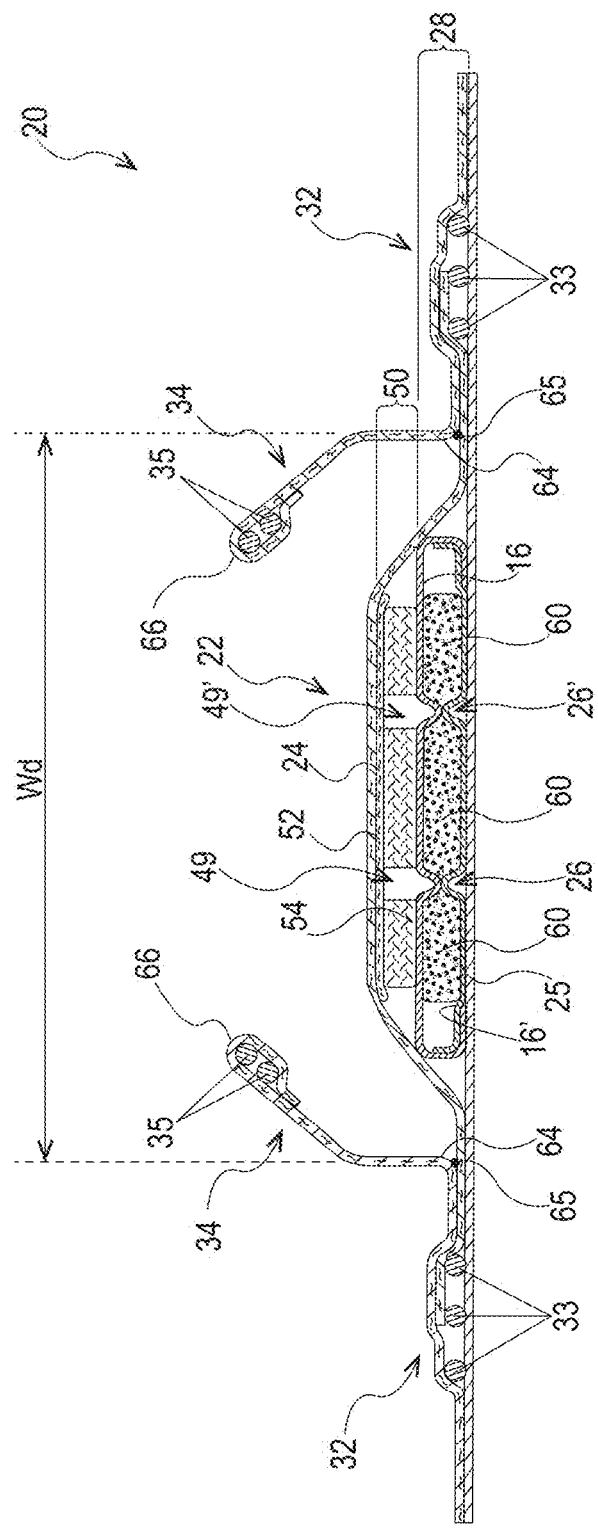
FIG. 2 is a cross-sectional view of the absorbent article taken about line 2-2 of FIG. 1 in accordance with the present disclosure.
Figure 3:
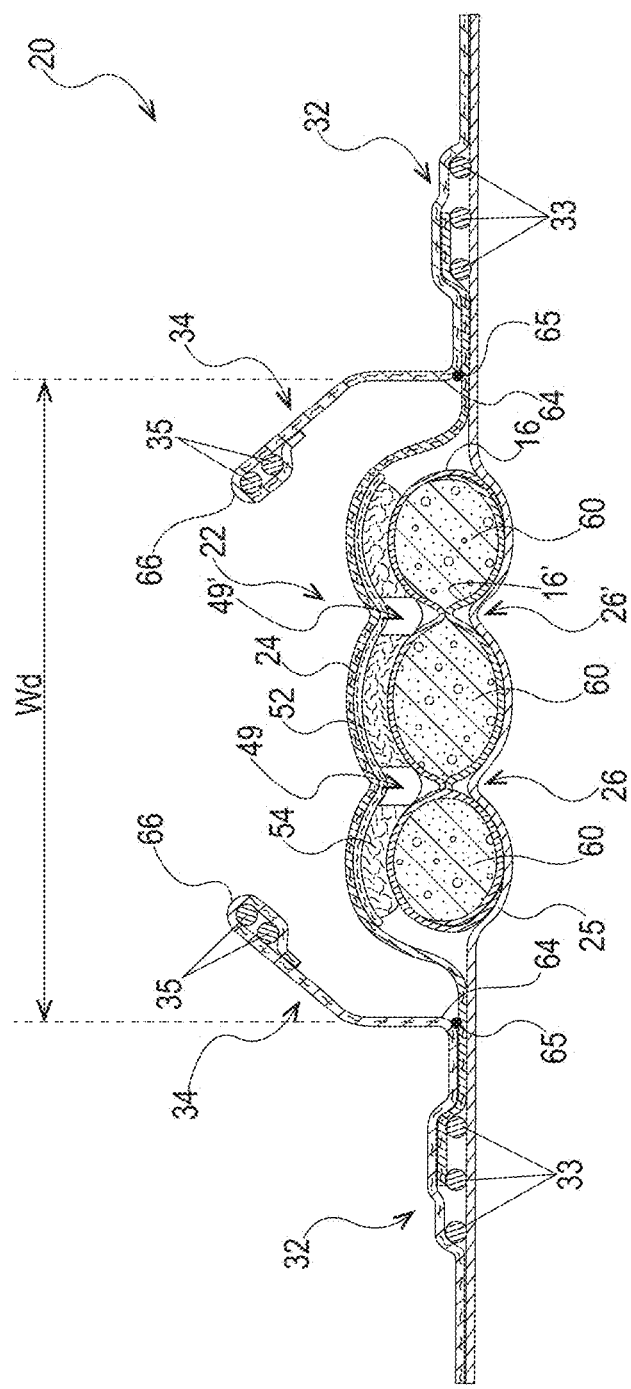
FIG. 3 is a view of the absorbent article of FIG. 2 where the absorbent article has been at least partially loaded with fluid in accordance with the present disclosure.

An example absorbent article 20 according to the present disclosure, shown in the form of a diaper, is represented in FIGS. 1-3. FIG. 1 is a plan view of the diaper, in a flat-out state, wearer-facing surface toward the viewer, with portions of the structure being cut-away to more clearly show the construction of the diaper. This diaper is shown for illustration purpose only as the present disclosure may be used for making a wide variety of diapers and other absorbent articles.

The absorbent article may comprise a liquid permeable topsheet 24, a liquid impermeable backsheet 25, an absorbent core 28 positioned at least partially intermediate the topsheet 24 and the backsheet 25, and barrier leg cuffs 34. The absorbent article may also comprise a liquid management system ("LMS") 50 (shown in FIG. 2), which, in the example represented, comprises a distribution layer 54 and an acquisition layer 52 that will both be further discussed below. In various embodiments, the acquisition layer 52 may instead distribute bodily exudates and the distribution layer 54 may instead acquire bodily exudates or both layers may distribute and/or acquire bodily exudates. The LMS 50 may also be provided as a single layer or two or more layers. The absorbent article may also comprise elasticized gasketing cuffs 32 joined to the chassis of the absorbent article, typically via the topsheet and/or backsheet, and substantially planar with the chassis of the diaper.

The Figures also show typical taped diaper components such as a fastening system comprising adhesive tabs 42 or other mechanical fasteners attached towards the rear edge of the absorbent article 20 and cooperating with a landing zone 44 on the front of the absorbent article 20. The absorbent article may also comprise other typical elements, which are not represented, such as a rear elastic waist feature and a front elastic waist feature, for example.

The absorbent article 20 may comprise a front waist edge 10, a rear waist edge 12 longitudinally opposing the front waist edge 10, a first side edge 3, and a second side edge 4 laterally opposing the first side edge 3. The front waist edge 10 is the edge of the absorbent article 20 which is intended to be placed towards the front of the user when worn, and the rear waist edge 12 is the opposite edge. Together the front waist edge 10 and the rear waist edge form waist opening when the absorbent article 20 is donned on a wearer. The absorbent article 20 may have a longitudinal axis 80 extending from the lateral midpoint of the front waist edge 10 to a lateral midpoint of the rear waist edge 12 of the absorbent article 20 and dividing the absorbent article 20 in two substantially symmetrical halves relative to the longitudinal axis 80, with article placed flat and viewed from the wearer-facing surface as illustrated FIG. 1. The absorbent article may also have a lateral axis 90 extending from the longitudinal midpoint of the first side edge 3 to the longitudinal midpoint of the second side edge 4. The length L of the absorbent article 20 may be measured along the longitudinal axis 80 from the front waist edge 10 to the rear waist edge 12. The crotch width of the absorbent article 20 may be measured along the lateral axis 90 from the first side edge 3 to the second side edge 4. The absorbent article 20 may comprise a front waist region 5, a rear waist region 6, and a crotch region 7. The front waist region, the rear waist region, and the crotch region each define ⅓ of the longitudinal length of the absorbent article. Front and back portions may also be defined on opposite sides of the lateral axis 90.

The topsheet 24, the backsheet 25, the absorbent core 28, and the other article components may be assembled in a variety of configurations, in particular by gluing or heat embossing, for example. Example diaper configurations are described generally in U.S. Pat. Nos. 3,860,003, 5,221,274, 5,554,145, 5,569,234, 5,580,411, and 6,004,306.

The absorbent core 28 may comprise an absorbent material comprising 75% to 100%, at least 80%, at least 85%, at least 90%, at least 95%, or at least 99%, all by weight, of the absorbent material, specifically reciting all 0.1% increments within the above-specified ranges and all ranges formed therein or thereby, and a core wrap enclosing the absorbent material. The core wrap may typically comprise two materials, substrates, or nonwoven materials 16 and 16' (see FIG. 8) for the top side and bottom side of the core.

The absorbent core 28 may comprises one or more channels, represented in FIG. 1 as the four channels 26, 26' and 27, 27'. Additionally or alternative, the LMS 50 may comprises one or more channels, represented in FIGS. 1-3 as channels 49, 49'. In some embodiments, the channels of the LMS 50 may be positioned within the absorbent article 20 such they aligned with, substantially aligned with, overlap, or at least partially overlap, the channels of the absorbent core 28. These and other components of the absorbent articles will now be discussed in more details.

Topsheet

The topsheet 24 is the part of the absorbent article that is directly in contact with the wearer's skin. The topsheet 24 may be joined to the backsheet 25, the core 28 and/or any other layers as is known to those of skill in the art. Usually, the topsheet 24 and the backsheet 25 are joined directly to each other in some locations (e.g., on or close to the periphery of the article) and are indirectly joined together in other locations by directly joining them to one or more other elements of the absorbent article 20.

The topsheet 24 may be compliant, soft-feeling, and non-irritating to the wearer's skin. Further, at least a portion of the topsheet 24 may be liquid permeable, permitting liquids to readily penetrate through its thickness. A suitable topsheet may be manufactured from a wide range of materials, such as porous foams, reticulated foams, apertured plastic films, or woven or nonwoven materials of natural fibers (e.g., wood or cotton fibers), synthetic fibers or filaments (e.g., polyester or polypropylene or bicomponent PE/PP fibers or mixtures thereof), or a combination of natural and synthetic fibers. If the topsheet 24 includes fibers, the fibers may be spunbond, carded, wet-laid, melt-blown, hydroentangled, or otherwise processed as is known in the art, in particular spunbond PP nonwoven.

Typical absorbent article topsheets have a basis weight of from about 5 gsm to about 50 gsm, from about 10 to about 35 gsm or from about 12 to about 30 gsm, but other basis weights are within the scope of the present disclosure.

Backsheet

The backsheet 25 is generally that portion of the absorbent article 20 positioned adjacent the garment-facing surface of the absorbent core 28 and which prevents, or at least inhibits, the bodily exudates absorbed and contained therein from soiling articles such as bedsheets and undergarments. The backsheet 25 is typically impermeable, or at least substantially impermeable, to liquids (e.g., urine, running BM), but permeable to vapors to allow the diaper to "breath". The backsheet may, for example, be or comprise a thin plastic film such as a thermoplastic film having a thickness of about 0.012 mm to about 0.051 mm. Example backsheet films include those manufactured by Tredegar Corporation, based in Richmond, Va., and sold under the trade name CPC2 film. Other suitable backsheet materials may include breathable materials which permit vapors to escape from the absorbent article 20 while still preventing, or at least inhibiting, bodily exudates from passing through the backsheet 25. Example breathable materials may include materials such as woven webs, nonwoven webs, composite materials such as film-coated nonwoven webs, microporous films, and monolithic films.

The backsheet 25 may be joined to the topsheet 24, the absorbent core 28, and/or any other element of the absorbent article 20 by any attachment methods known to those of skill in the art. Suitable attachment methods are described above with respect to methods for joining the topsheet 24 to other elements of the absorbent article 20.

Absorbent Core

As used herein, the term "absorbent core" refers to the individual component of the absorbent article having the most absorbent capacity and that comprises an absorbent material. The absorbent core may comprise a core wrap or core bag (hereafter "core wrap") enclosing the absorbent material. The term "absorbent core" does not include the LMS or any other component of the absorbent article which is not either integral part of the core wrap or placed within the core wrap. The absorbent core may comprise, consist essentially of, or consist of, a core wrap, absorbent material as defined below, and glue enclosed within the core wrap. Pulp or air-felt may also be present within the core wrap and may form a portion of the absorbent material. The absorbent core periphery, which may be the periphery of the core wrap, may define any suitable shape, such as a "T," "Y," "hour-glass," or "dog-bone" shape, for example. An absorbent core periphery having a generally "dog bone" or "hour-glass" shape may taper along its width towards the middle or "crotch" region of the core. In this way, the absorbent core may have a relatively narrow width in an area of the absorbent core intended to be placed in the crotch region of an absorbent article.

The absorbent core 28 of the present disclosure may comprise an absorbent material with a high amount of superabsorbent polymers (herein abbreviated as "SAP") enclosed within a core wrap. The SAP content may represent 70% to 100% or at least 70%, 75%, 80%, 85%, 90%, 95%, 99%, or 100% by weight of the absorbent material contained in the core wrap. The SAP useful with the present disclosure may include a variety of water-insoluble, but water-swellable polymers capable of absorbing large quantities of fluids. The core wrap is not considered as absorbent material for the purpose of assessing the percentage of SAP in the absorbent core. The remainder of the absorbent material in the core 28 may be air-felt.

"Absorbent material" means a material which has some absorbency property or liquid retaining properties, such as SAP, cellulosic fibers as well as synthetic fibers. Typically, glues used in making absorbent cores have no absorbency properties and are not considered as absorbent material. The SAP content may be higher than 80%, for example at least 85%, at least 90%, at least 95%, at least 99%, and even up to and including 100% of the weight of the absorbent material contained within the core wrap, as stated above. This provides a relatively thin core compared to conventional cores typically comprising between 40-60% SAP, for example, and high content of cellulose fibers or airfelt. The absorbent material may comprise less than 15% or less than 10% weight percent of natural or synthetic fibers, less than 5% weight percent, less than 3% weight percent, less than 2% weight percent, less than 1% weight percent, or may even be substantially free of, or free of, natural and/or synthetic fibers, specifically reciting all 0.1% increments within the specified ranges and all ranges formed therein or thereby. The absorbent material may comprise little or no airfelt (cellulose) fibers, in particular the absorbent core may comprise less than 15%, 10%, 5%, 3%, 2%, 1% airfelt (cellulose) fibers by weight, or may even be substantially free of, or free of, cellulose fibers, specifically reciting all 0.1% increments within the specified ranges and all ranges formed therein or thereby.

Figure 4:
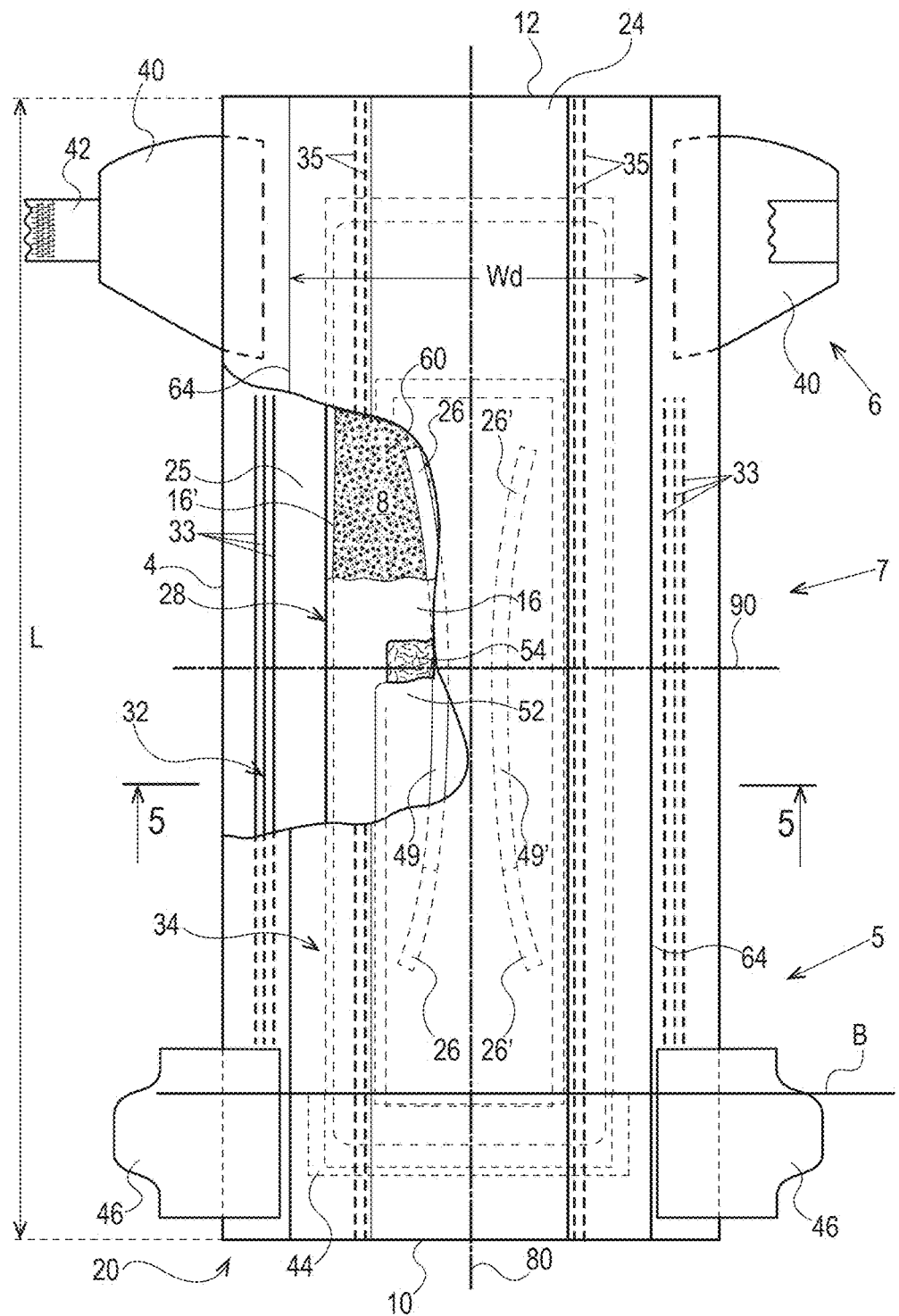
FIG. 4 is a top view of another absorbent article with some layers partially removed in accordance with the present disclosure.
Figure 5:
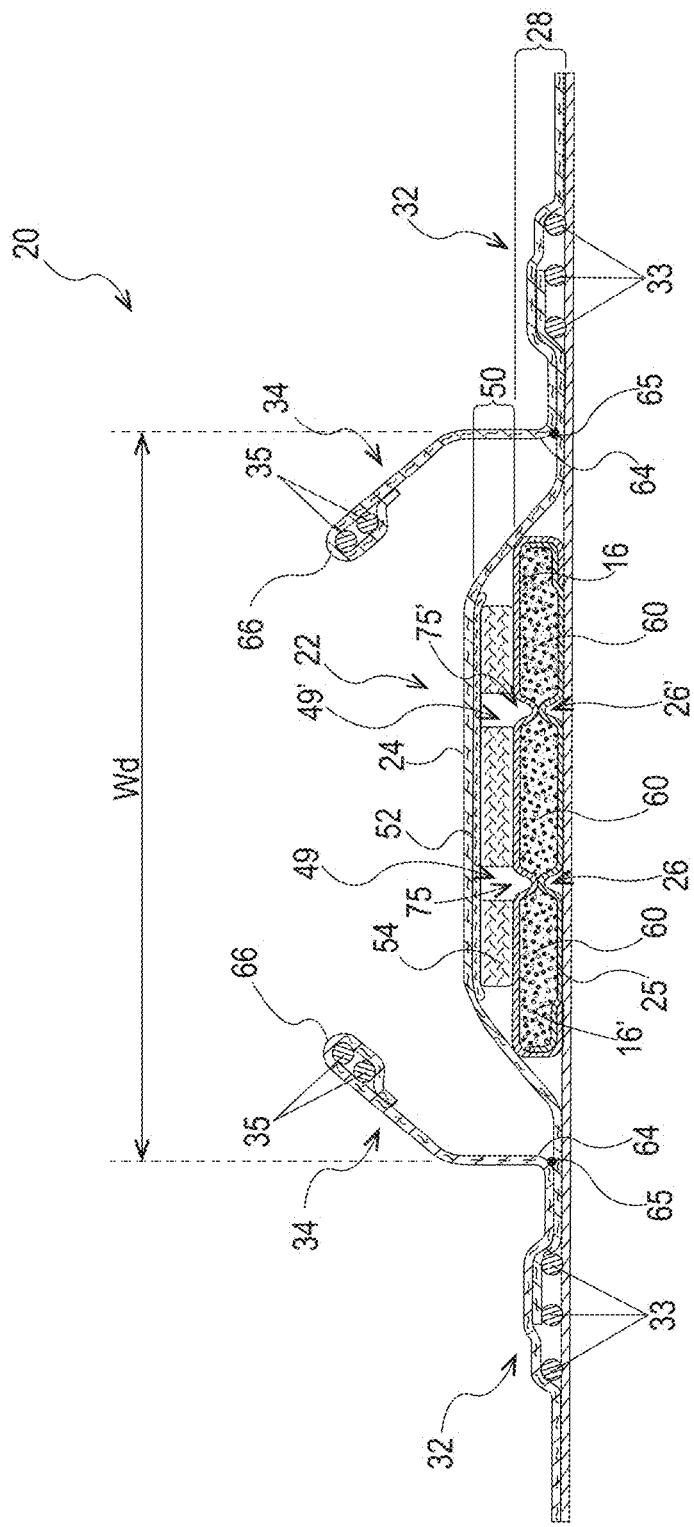
FIG. 5 is a cross-sectional view of the absorbent article taken about line 5-5 of FIG. 4 in accordance with the present disclosure.
Figure 6:
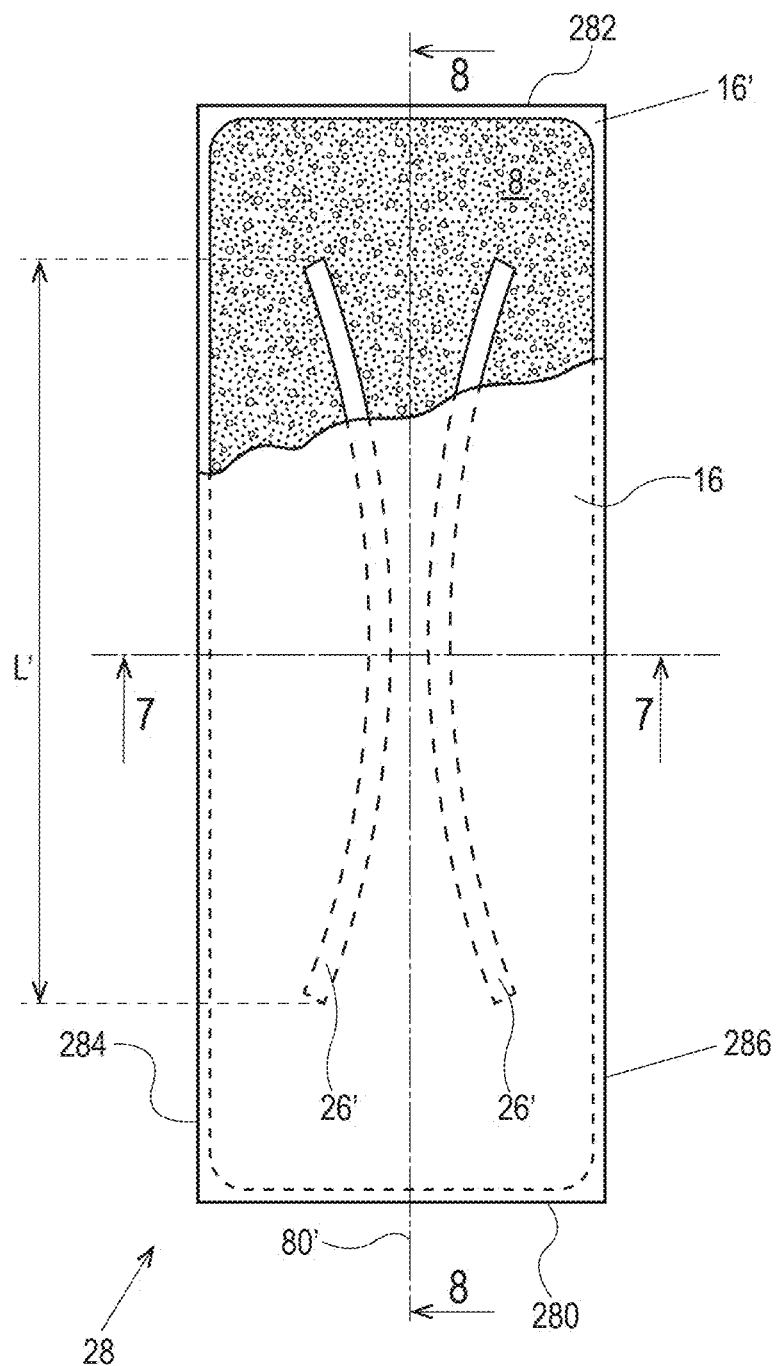
FIG. 6 is a top view of an absorbent core of the absorbent article of FIG. 4 with some layers partially removed in accordance with the present disclosure.
Figure 7:
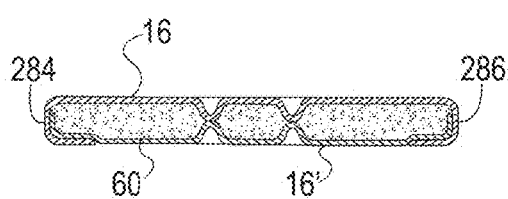
FIG. 7 is a cross-sectional view of the absorbent core taken about line 7-7 of FIG. 6 in accordance with the present disclosure.
Figure 8:
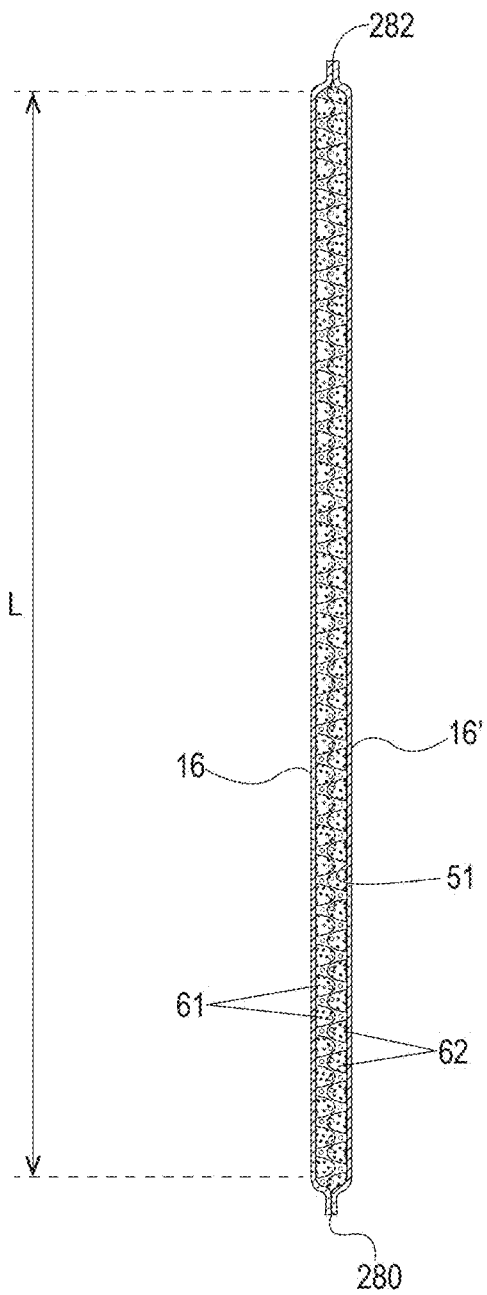
FIG. 8 is a cross-sectional view of the absorbent core taken about line 8-8 of FIG. 6 in accordance with the present disclosure.

The example absorbent core 28 of the absorbent article of FIGS. 4 and 5 is shown in isolation in FIGS. 6-8. The absorbent core 28 may comprises a front side 280, a rear side 282, and two longitudinal sides 284, 286 joining the front side 280 and the rear side 282. The absorbent core 28 may also comprise a generally planar top side and a generally planar bottom side. The front side 280 of the core 28 is the side of the core 28 intended to be placed towards the front waist edge 10 of the absorbent article. The core 28 may have a longitudinal axis 80' corresponding substantially to the longitudinal axis 80 of the absorbent article, as seen from the top in a planar view as in FIG. 1. The absorbent material may be distributed in higher amount towards the front side than towards the rear side as more absorbency may be required at the front in particular articles. The absorbent material may have a non-uniform basis weight or a uniform basis weight across any portion of the core. The core wrap may be formed by two nonwoven materials, substrates, laminates, or other materials, 16, 16' which may be at least partially sealed along the sides of the absorbent core. The core wrap may be at least partially sealed along its front side 280, rear side 282, and two longitudinal sides 284, 286 so that substantially no absorbent material leaks out of the absorbent core wrap. The first material, substrate, or nonwoven 16 may at least partially surround the second material, substrate, or nonwoven 16' to form the core wrap, as illustrated in FIG. 7. The first material 16 may surround a portion of the second material 16' proximate to the first and second side edges 284 and 286.

Cores comprising relatively high amount of SAP with various core designs are disclosed in U.S. Pat. No. 5,599,335 (Goldman), EP 1,447,066 (Busam), WO 95/11652 (Tanzer), U.S. Pat. Publ. No. 2008/0312622A1 (Hundorf), and WO 2012/052172 (Van Malderen).

The absorbent material may be one or more continuous layers present within the core wrap. Alternatively, the absorbent material may be comprised of individual pockets or stripes of absorbent material enclosed within the core wrap. In the first case, the absorbent material may be, for example, obtained by the application of a single continuous layer of absorbent material. The continuous layer of absorbent material, in particular of SAP, may also be obtained by combining two or more absorbent layers having discontinuous absorbent material application pattern, wherein the resulting layer is substantially continuously distributed across the absorbent particulate polymer material area, as disclosed in U.S. Pat. Appl. Publ. No. 2008/0312622A1 (Hundorf), for example. The absorbent core 28 may comprise a first absorbent layer and a second absorbent layer. The first absorbent layer may comprise the first material 16 and a first layer 61 of absorbent material, which may be 100% or less of SAP. The second absorbent layer may comprise the second material 16' and a second layer 62 of absorbent material, which may also be 100% or less of SAP. The absorbent core 28 may also comprise a fibrous thermoplastic adhesive material 51 at least partially bonding each layer of absorbent material 61, 62 to its respective material 16 or 16'. This is illustrated in FIGS. 7-8, as an example, where the first and second SAP layers have been applied as transversal stripes or "land areas" having the same width as the desired absorbent material deposition area on their respective substrate before being combined. The stripes may comprise different amount of absorbent material (SAP) to provide a profiled basis weight along the longitudinal axis of the core 80. The first material 16 and the second material 16' may form the core wrap.

The fibrous thermoplastic adhesive material 51 may be at least partially in contact with the absorbent material 61, 62 in the land areas and at least partially in contact with the materials 16 and 16' in the junction areas. This imparts an essentially three-dimensional structure to the fibrous layer of thermoplastic adhesive material 51, which in itself is essentially a two-dimensional structure of relatively small thickness, as compared to the dimension in length and width directions. Thereby, the fibrous thermoplastic adhesive material may provide cavities to cover the absorbent material in the land area, and thereby immobilizes this absorbent material, which may be 100% or less of SAP.

Core Wrap

The core wrap may be made of a single substrate, material, or nonwoven folded around the absorbent material, or may comprise two (or more) substrates, materials, or nonwovens which are attached to another. Typical attachments are the so-called C-wrap and/or sandwich wrap. In a C-wrap, as illustrated, for example, in FIGS. 2 and 7, the longitudinal and/or transversal edges of one of the substrates are folded over the other substrate to form flaps. These flaps are then bonded to the external surface of the other substrate, typically by gluing. Other techniques may be used to form a core wrap. For example, the longitudinal and/or transversal edges of the substrates may be bonded together and then folded underneath the absorbent core 28 and bonded in that position. The core wrap may be at least partially sealed along all the sides of the absorbent core so that substantially no absorbent material leaks out of the core. By "substantially no absorbent material" it is meant that less than 5%, less than 2%, less than 1%, or about 0% by weight of absorbent material escape the core wrap. The term "seal" is to be understood in a broad sense. The seal does not need to be continuous along the whole periphery of the core wrap but may be discontinuous along part or the whole of it, such as formed by a series of seal points spaced on a line. A seal may be formed by gluing and/or thermal bonding.

The core wrap may also be formed by a single substrate which may enclose as in a parcel wrap the absorbent material and be sealed along the front side and rear side of the core and one longitudinal seal.

SAP Deposition Area

The absorbent material deposition area 8 may be defined by the periphery of the layer formed by the absorbent material 60 within the core wrap, as seen from the top side of the absorbent core. The absorbent material deposition area 8 may have various shapes, in particular, a so-called "dog bone" or "hour-glass" shape, which shows a tapering along its width towards the middle or "crotch" region of the core. In this way, the absorbent material deposition area 8 may have a relatively narrow width in an area of the core intended to be placed in the crotch region of the absorbent article, as illustrated in FIG. 1. This may provide better wearing comfort. The absorbent material deposition area 8 may also be generally rectangular, for example as shown in FIGS. 4-6, but other deposition areas, such as a "T," "Y," "hour-glass," or "dog-bone" shapes are also within the scope of the present disclosure.

Channels in the Absorbent Core

The absorbent material deposition area 8 may comprise at least one channel 26, which is at least partially oriented in the longitudinal direction of the absorbent article 80 (i.e., has a longitudinal vector component). Other channels may be at least partially oriented in the lateral direction (i.e., has a lateral vector component) or in any other direction. In the following, the plural form "channels" will be used to mean "at least one channel". The channels may be circular, oblong, or be in the shape of a variety of other closed polygons. The channels may be formed in various ways. For example, the channels may be formed by zones within the absorbent material deposition area 8 which may be substantially free of, or free of, absorbent material, in particular, SAP. In addition or alternatively, the channels may also be formed by continuously or discontinuously bonding the top side of the core wrap to the bottom side of the core wrap through the absorbent material deposition area 8. The channels may be continuous or intermittent. The liquid management system 50, or another layer of the absorbent article, may also comprise channels, which may or not correspond to the channels of the absorbent core, as described in more detail below.

The absorbent core 28 may comprise more than two channels, for example, at least 3, at least 4, etc. Shorter channels may also be present, for example in the rear waist region 6 or the front waist region 5 of the core as represented by the pair of channels 27, 27' in FIG. 1 towards the front of the absorbent article 20. The channels may comprise one or more pairs of channels symmetrically arranged, or otherwise arranged relative to the longitudinal axis 80 or the lateral axis 90.

At least some or all of the channels may be permanent channels, meaning their integrity is at least partially maintained both in the dry state and in the wet state. Permanent channels may be obtained by provision of one or more adhesive materials, for example, the fibrous layer of adhesive material or construction glue that helps adhere a substrate with an absorbent material within the walls of the channel. Permanent channels may also be formed by bonding the upper side and lower side of the core wrap (e.g., the first substrate 16 and the second substrate 16') and/or the topsheet 24 to the backsheet 25 together through the channels. Typically, an adhesive may be used to bond both sides of the core wrap or the topsheet and the a backsheet through the channels, but it is possible to bond via other known processes, such as pressure bonding, ultrasonic bonding, heat bonding, or combination thereof. The core wrap or the topsheet 24 and the backsheet 25 may be continuously bonded or intermittently bonded along the channels. The channels may advantageously remain or become visible at least through the topsheet and/or backsheet when the absorbent article is fully loaded with a fluid. This may be obtained by making the channels substantially free of SAP, so they will not swell, and sufficiently large so that they will not close when wet. Furthermore, bonding the core wrap to itself or the topsheet to the backsheet through the channels may be advantageous.

Absorbent cores and/or LMSs without any channels are also within the scope of the present disclosure. These cores may include airfelt-free cores, SAP/pulp cores, pulp cores, or other cores known to those of skill in the art.

Barrier Leg Cuffs

The absorbent article may comprise a pair of barrier leg cuffs 34. Each barrier leg cuff may be formed by a piece of material which is bonded to the absorbent article so it can extend upwards from the inner surface of the absorbent article and provide improved containment of liquids and other bodily exudates approximately at the junction of the torso and legs of the wearer. The barrier leg cuffs 34 are delimited by a proximal edge 64 joined directly or indirectly to the topsheet 24 and/or the backsheet 25 and a free terminal edge 66, which is intended to contact and form a seal with the wearer's skin. The barrier leg cuffs 34 extend at least partially between the front waist edge 10 and the rear waist edge 12 of the absorbent article on opposite sides of the longitudinal axis 80 and are at least present in the crotch region 7. The barrier leg cuffs 34 may be joined at the proximal edge 64 with the chassis of the absorbent article by a bond 65 which may be made by gluing, fusion bonding, or combination of other suitable bonding processes. The bond 65 at the proximal edge 64 may be continuous or intermittent. The bond 65 closest to the raised section of the leg cuffs 34 delimits the proximal edge 64 of the standing up section of the leg cuffs 34.

The barrier leg cuffs 34 may be integral with the topsheet 24 and the backsheet 25 or may be a separate material joined to the absorbent article's chassis. The material of the barrier leg cuffs 34 may extend through the whole length of the diapers but may be "tack bonded" to the topsheet 24 towards the front waist edge 10 and rear waist edge 12 of the absorbent article so that in these sections the barrier leg cuff material remains flush with the topsheet 24.

Each barrier leg cuff 34 may comprise one, two or more elastic strands or strips of film 35 close to this free terminal edge 66 to provide a better seal.

In addition to the barrier leg cuffs 34, the absorbent article may comprise gasketing cuffs 32, which are joined to the chassis of the absorbent article, in particular to the topsheet 24 and/or the backsheet 25 and are placed externally relative to the barrier leg cuffs 34. The gasketing cuffs 32 may provide a better seal around the thighs of the wearer. Each gasketing leg cuff may comprise one or more elastic strings or elastic elements in the chassis of the absorbent article between the topsheet 24 and backsheet 25 in the area of the leg openings. All or a portion of the barrier leg and/or gasketing cuffs may be treated with a lotion or skin care composition. The barrier leg cuffs may be constructed in a number of different configurations, including those described in U.S. Pat. App. Publ. No. 2012/0277713.

Front and Rear Ears

In an embodiment, the absorbent article may comprise front ears 46 and rear ears 40. The ears may be an integral part of the chassis, such as formed from the topsheet 24 and/or backsheet 25 as side panel. Alternatively, as represented on FIG. 1, the ears (46, 40) may be separate elements attached by gluing, heat embossing, and/or pressure bonding. The rear ears 40 may be stretchable to facilitate the attachment of the tabs 42 to the landing zone 44 and maintain the taped diapers in place around the wearer's waist. The rear ears 40 may also be elastic or extensible to provide a more comfortable and contouring fit by initially conformably fitting the absorbent article to the wearer and sustaining this fit throughout the time of wear well past when absorbent article has been loaded with exudates since the elasticized ears allow the sides of the absorbent article to expand and contract.

Liquid Management System (LMS)

One function of the LMS 50 is to quickly acquire the fluid and distribute it to the absorbent core 28 in an efficient manner. The LMS 50 may comprise one or more layers, which may form a unitary layer or may remain as discrete layers which may be attached to each other. The LMS 50 may comprise two layers: a distribution layer 54 and an acquisition layer 52 disposed between the absorbent core and the topsheet, but the present disclosure is not limited to such a configuration.

The LMS 50 may comprise SAP as this may slow the acquisition and distribution of the fluid. In other embodiments, the LMS may be substantially free (e.g., 80%, 85%, 90%, 95%, or 99% free of) or completely free of SAP. The LMS may also comprise one or more of a variety of other suitable types of materials, such as opened-cell foam, airlaid fibers, or carded, resin bonded nonwoven materials, for example. Suitable example LMSs are described in WO 2000/59430 (Daley), WO 95/10996 (Richards), U.S. Pat. No. 5,700,254 (McDowall), and WO 02/067809 (Graef), for example.

Distribution Layer

The LMS 50 may comprise a distribution layer 54. The distribution layer 54 may comprise at least 50% or more by weight of cross-linked cellulose fibers, for example. The cross-linked cellulosic fibers may be crimped, twisted, or curled, or a combination thereof including crimped, twisted, and curled. This type of material is disclosed in U.S. Pat. Publ. No. 2008/0312622 A1 (Hundorf).

Acquistion Layer

The LMS 50 may alternatively or additionally comprise an acquisition layer 52. The acquisition layer 52 may be disposed, for example, between the distribution layer 54 and the topsheet 24. The acquisition layer 52 may be or may comprise a non-woven material, such as an SMS or SMMS material, comprising a spunbonded, a melt-blown and a further spunbonded layer or alternatively a carded chemical-bonded nonwoven. The acquisition layer 52 may comprise air or wet-laid cellulosic, cross-linked cellulosic, or synthetic fibers, or blends thereof. The acquisition layer 52 may comprise a roll-stock web of synthetic fibers (which may be processed to increase void space, such as by solid state formation), or a combination of synthetic and cellulosic fibers, bonded together to form a highloft material. Alternatively, the acquisition layer 52 may comprise absorbent open cell foam. The nonwoven material may be latex bonded.

Channels in Liquid Management System

The LMS 50 of the absorbent article 20 may comprise channels that may generally enable better conformation of the absorbent article to the wearer's anatomy, leading to increased freedom-of-movement and reduced gapping. One or more of the channels of the LMS 50 may be configured to work in concert with various channels in the absorbent core 28, as discussed above. Furthermore, channels in the LMS 50 may also provide increased void space to hold and distribute urine, BM or other bodily exudates within the absorbent article, leading to reduced leakage and skin contact. Channels in the LMS 50 may also provide internal serviceable indicia, especially when highlighted via physical differences in texture, color, and/or pattern, to facilitate achieving the correct alignment of the absorbent article on a wearer. Thus, such physical differences may be, for example, visually and/or tactilely noticeable.

Similar to the channels in the absorbent core 28, a channel in the LMS 50 may be any region in a layer, or extending through more than one layer, that has a substantially lower basis weight or thickness than the surrounding material, as set forth in the definition of "channel" above. The channels in the LMS 50 may also serve to reduce the tension forces to enable controlled bending and maintain the LMS 50 in close proximity to the absorbent core 28. Thus, the presence of channels in the LMS 50, which may or may not be aligned with any channels in an underlying absorbent core 28, may generally function as hinges to allow for a more flexible composite structure. In some cases, for example, the channels of the LMS 50 allow for the LMS 50 to move toward the absorbent core 28 in a controlled bending arrangement, thereby limiting the separation between the LMS 50 and the absorbent core 28. Moreover, a channel in the LMS 50 may assist in the routing of fluid or other bodily exudates from one region of the absorbent article 20 to another region of the absorbent article 20. Such routing may desirably improve the overall distribution of fluid through the absorbent article 20 and may lead to increase in comfort, wearability, or longevity of the article.

For multi-layered LMSs, the channels may be present in one or more layers of the LMS 50 and may vary in their dimensions in all three planes of reference. The width of a given channel in the LMS 50 may vary in the longitudinal direction (i.e., in a direction substantially parallel to the longitudinal axis of the absorbent article). A channel may also have a different width, length, and/or volume in front of a lateral axis or lateral separation element of the absorbent article than behind the lateral axis or lateral separation element. The channels of the LMS 50 may have a range of widths, lengths, shapes, volumes, and patterns, similar to the channels described above with regard to the absorbent core 28.

One or more channels in the LMS 50 may at least partially overlap, or fully overlap, a channel in the absorbent core 28, creating a deeper recess in the overlapping regions. For embodiments where the LMS 50 includes more than one layer, the layer closest to the absorbent core 28 may include a channel. One or more layers in the structure, such as the topsheet 24, an acquisition layer 52, distribution layer 54, or other layers, may be bonded to an element of the absorbent core 28 in this region to increase the depth of the combined channel. In an embodiment, the channel in the acquisition layer 52 of the LMS 50 and the channel in the absorbent core 28 are coincident such that the channels are completely overlapping. In another embodiment, channels in the LMS and storage layers have no overlapping area. Other embodiments have a vertical overlap between the channels in the two layers that encompass the intervening range such that they partially overlap.

Referring again to FIGS. 1-5, the LMS 50 in the illustrated example is shown defining two channels 49, 49'. The channels 49, 49' are at least partially oriented in the longitudinal direction of the absorbent article 80 (i.e., has a longitudinal vector component). Other channels in the LMS may be at least partially oriented in the lateral direction (i.e., has a lateral vector component), or in any other direction, and the channels in the LMS 50 may be continuous or intermittent. Some channels in the LMS may be round, oblong, square, rectangular, triangular or any other suitable shape. The channels may be formed in various ways. For example, the channels may be formed by zones within the LMS 50 which may be substantially free of, or free of, acquisition or distribution material.

The channels of the LMS 50 may be present at least at the same longitudinal level as the lateral axis 90 in the absorbent article, as represented in FIG. 1 with the two longitudinally extending channels 49, 49'. The channels may also extend from the crotch region 7 or may be present in the front waist region 5 and/or in the rear waist region 6 of the absorbent article. In FIG. 1, the channels 49, 49' are generally coincident with channels 26, 26', with channels 26, 26' having a longer length in the longitudinal direction towards the front waist edge 10 of the absorbent article 20.

The LMS 50 may define any suitable number of channels, such as at least one or more than two channels. Shorter channels may also be present, for example in the rear waist region 6 or the front waist region 5 of the LMS 50. The channels of the LMS 50 may comprise one or more pairs of channels symmetrically arranged, or otherwise arranged relative to the longitudinal axis 80 and/or the lateral axis 90, or other transverse axis. The channels may extend substantially longitudinally or substantially laterally.

At least some or all of the channels in the LMS 50 may be permanent channels, meaning their integrity is at least partially maintained both in the dry state and in the wet state. Permanent channels may be obtained by provision of one or more adhesive materials, for example, the fibrous layer of adhesive material or construction glue that helps adhere a substrate with an absorbent material within the walls of the channel. Permanent channels may also be formed by bonding the topsheet 24 to the backsheet 25 together through a channel of the LMS 50. Typically, an adhesive may be used to bond the topsheet 24 and the backsheet 25 through the channels, but it is possible to bond via other known processes, such as pressure bonding, ultrasonic bonding, heat bonding, or combination thereof. The topsheet 24 and the backsheet 25 may be continuously bonded or intermittently bonded along or within portions of or all of the channels.

In an embodiment, referring to FIG. 1, the LMS 50 may comprise at least two channels (e.g., 49, 49'). These channels may be free of, or substantially free of (e.g., less than 10%, less than 5%, less than 3%, less than 2%, or less than 1%), non-woven material or cross-linked cellulose fibers and may be at least partially oriented in the longitudinal direction and/or may be at least partially oriented in the lateral direction.

Figure 9:
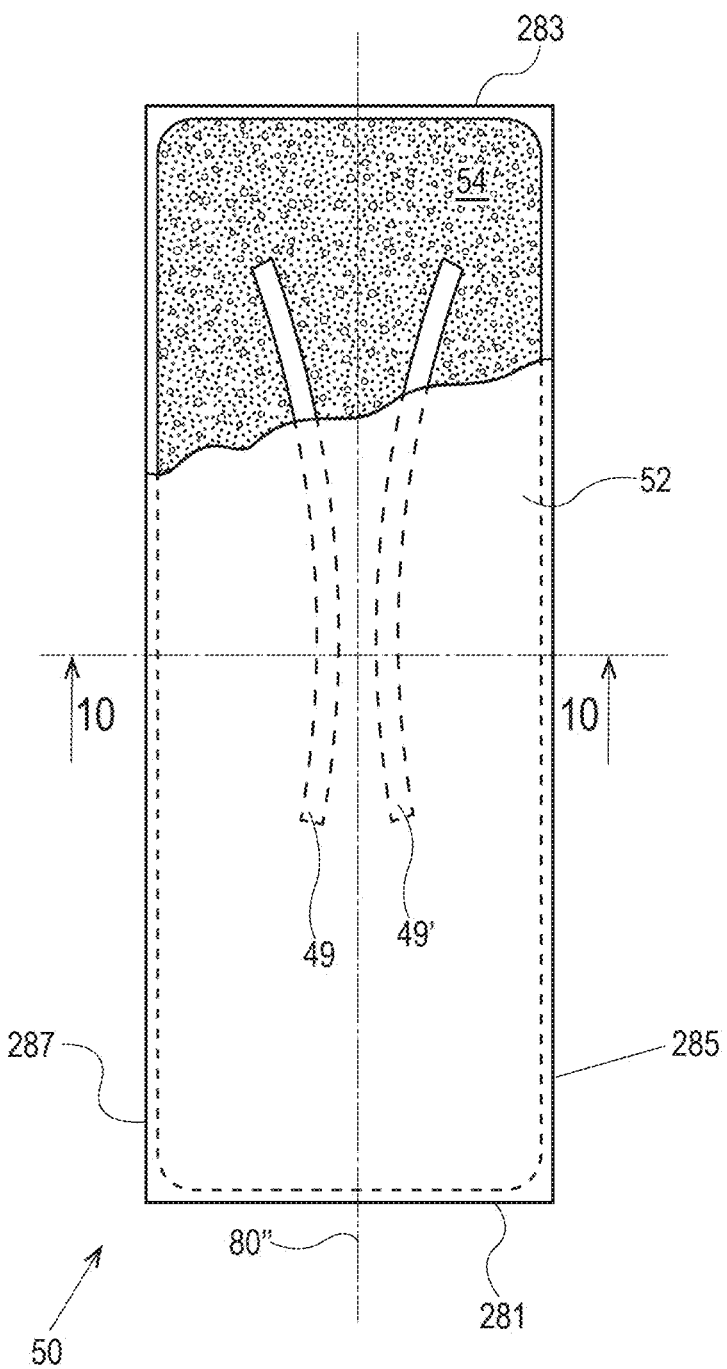
FIG. 9 is a top view of a LMS of the absorbent article of FIG. 4 with some layers partially removed in accordance with the present disclosure.
Figure 10:
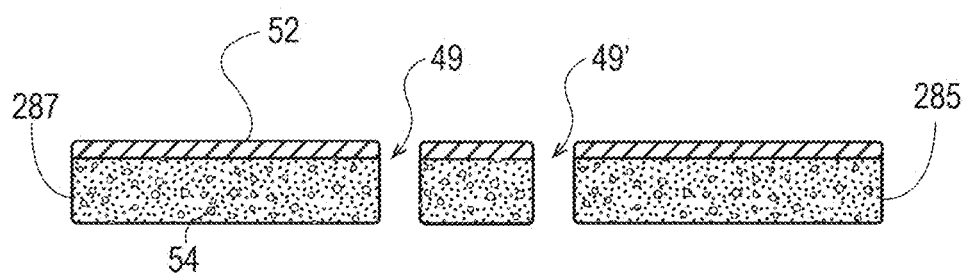
FIG. 10 is a cross-sectional view of the liquid management system taken about line 10-10 of FIG. 9 in accordance with the present disclosure.
Figure 11:
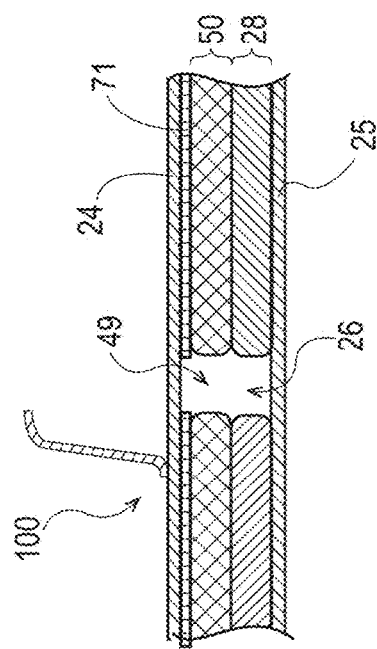
FIGS. 11-14 are examples longitudinal cross-sectional views of a portion of an absorbent article having a channel in an absorbent core and an LMS and a substantially laterally-extending separation element extending from the topsheet in accordance with the present disclosure.
Figure 12:
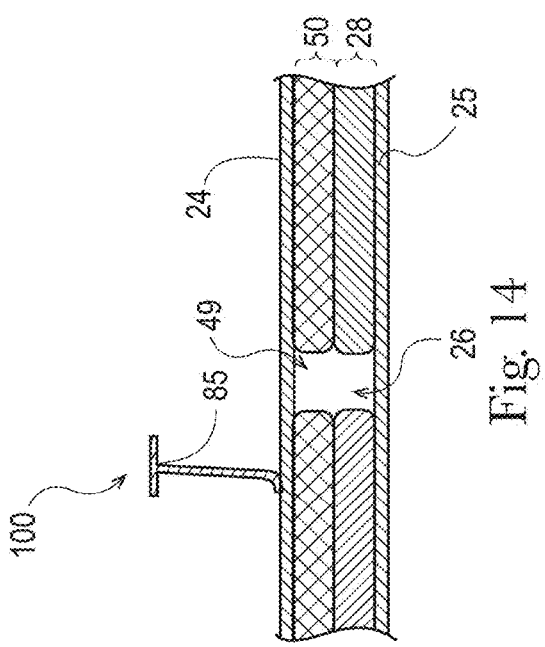
Figure 13:
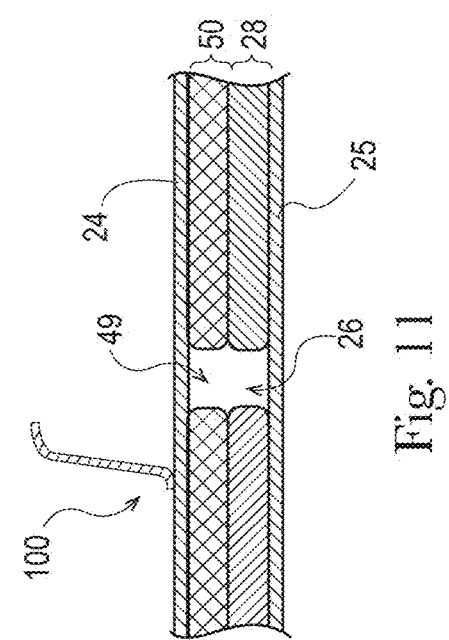
Figure 14:
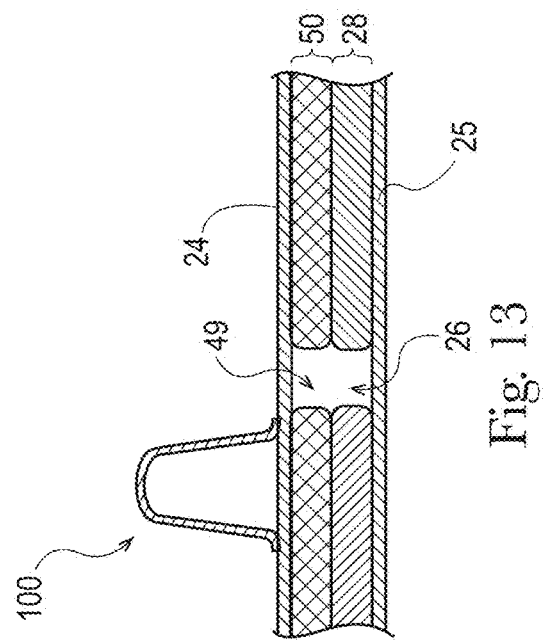

The example LMS 50 of the absorbent article of FIGS. 4-5 is shown in isolation in FIGS. 9-10 where FIG. 10 is a cross-sectional view of the LMS 50 taken about line 10-10 of FIG. 9. The LMS 50 may comprises a front side 281, a rear side 283, and two longitudinal sides 285, 287 joining the front side 281 and the rear side 283. The LMS 50 may also comprise a generally planar top side and a generally planar bottom side. The front side 281 of the LMS is the side of the LMS intended to be placed towards the front waist edge 10 of the absorbent article. The LMS 50 may have a longitudinal axis 80'' corresponding substantially to the longitudinal axis 80 of the absorbent article, as seen from the top in a planar view as in FIG. 1. In the illustrated embodiment, the LMS 50 comprises a distribution layer 54 and an acquisition layer 52 which cooperate to define the channels 49, 49'. In other embodiments, less than all of the layers of the LMS 50 may define the channel such that at least one layer of the LMS 50 is continuous while another layer of the LMS 50 is discontinuous.

While portions of the channels 26, 26' of the absorbent core 28 and the channels 49, 49' of the LMS 50 shown in FIGS. 1-10 are generally aligned, this disclosure is not so limited. In fact, as is to be appreciated, particular arrangements of the channels in an LMS 50 and/or an absorbent core 28 may vary.

Substantially Laterally-Extending Separation Element

A wearer-facing surface, or topsheet, of an absorbent article may have a visual front portion and a visual back portion. The visual front portion and the visual back portion may be separated by a substantially laterally-extending separation element 100. The term "substantially laterally" means within +/−15 degrees from a direction parallel to the lateral axis. The substantially laterally-extending separation element 100 may be, for example, a graphical indicia printed on the topsheet of the absorbent article, or other layer of the absorbent article (e.g., LMS 50), that is visible through the topsheet. The substantially laterally-extending separation element 100 may also be a portion of a tinted layer that is visible through the wearer-facing surface of the topsheet or the end of an underlying layer that has a different color than the topsheet. Alternatively or additionally, the visual front portion may be visually distinct from the visual back portion based on a color difference and/or a printed pattern difference. Such visual separation between the visual front portion and the visual back portion may help for proper alignment of the absorbent article during its application and help the appearance of separate zones configured for urine management and, separately, for BM management.

The substantially laterally-extending separation element 100, in various forms, may comprise a structural separator that is located in the region of the absorbent article generally corresponding to the perineal region of the wearer (i.e., disposed between the urethra and the anus). The structural separator may, for example, prevent, or at least somewhat inhibit, the surface migration of urine to the back of the absorbent article and BM to the front of the absorbent article. A structural separator may include any three-dimensional feature or component that functions as a transverse or laterally extending barrier ("TVB"), such as one or more projections above the wearer-facing surface of the absorbent article, recesses below the plane of the wearer-facing surface, and combinations thereof. One example includes a substantially laterally-oriented web or sheet that is attached to the wearer-facing surface of the absorbent article and that is attached on its ends to the barrier leg cuffs. Attachment to the barrier leg cuffs and the wearer-facing surface may provide a "seal" created by the TVB with respect to the front and back regions of the absorbent article to prevent, or at least inhibit, bodily exudates flow between the regions.

The structural separator may be rectangular or square when laid out flat in a relaxed, contracted state onto an even horizontal surface. The structural separator may also be trapezoidal when laid out flat in a relaxed, contracted state onto an even horizontal surface. The structural separator may be hydrophobic (e.g., it may be hydrophilic and made hydrophobic with a hydrophobic coating, for example a wax or a hydrophobic surface coating comprising one or more silicone polymers or fluorinated polymers.) The structural separator may have an elastic behavior such that it can be significantly elastically extensible in a lateral, transverse direction or other direction. The structural separator may have a certain tension during wear of the absorbent article to ensure that the structural separator forms an effective separator (barrier) with a Z-direction dimension, to avoid, or at least inhibit, migration of feces from the back to the front of the structural separator. Other structural separators may include raised or thicker portions of the topsheet, elements of the LMS or absorbent core, separately applied elements, or holes or depressions in one or more of the absorbent core elements or LMS.

Further to the above, the structural separator may have any suitable structure and may be a ridge, bump, and/or flap, for example. Some example cross-sectional views of substantially laterally-extending separation elements 100 configurations in the form of structural separators are illustrated in FIGS. 11-14. Any other suitable structural separators are within the scope of the present disclosure. The structural separator may be placed along a lateral axis of an absorbent article or may be positioned at an angle that is oblique to the lateral axis. The structural separator may also be placed in other locations that are not along the lateral axis (e.g., location in front of or behind the lateral axis). One or more structural separators may be incorporated into absorbent articles having a variety of configurations. Suitable structural separators and substantially laterally-extending separation elements are disclosed in greater detail in U.S. Provisional Patent Application Ser. No. 61/870,365, filed on Aug. 27, 2013, for example.

Substrates, such as topsheets and/or LMS, for example, may have one or more zones in different regions or areas of the substrates. Some example configurations of zones in a topsheet and/or an LMS are illustrated in FIGS. 15-32. In various figures, the zones are labeled Z1-Z6, although it is within the scope of the present disclosure to have any number of zones having any number of configurations, shapes, and/or sizes. While the topsheet 24 is illustrated as rectangular in FIGS. 15-19, it is within the scope of the present disclosure to have the topsheet be any suitable shape for absorbent articles, such as an hourglass shape, for example. The wearer-facing surface of the topsheet 24 is facing the viewer in FIGS. 15-32. Throughout FIGS. 15-32, if applicable, element 100 is the substantially laterally-extending separation element, element 90 is a lateral axis of the absorbent article, element 80 is a longitudinal axis of the absorbent article, F stands for the front of the absorbent article, and B stands for the back of the absorbent article. The lateral axis and the longitudinal axis will be apparent in all of FIGS. 15-32, although not illustrated in each figure.

For all of the zones discussed below, it will be understood that although a particular treatment may be specified for a specific zone, the zone may also include one or more other treatments or flow control materials. For example, if a certain morphological treatment is specified in a certain zone, another morphological treatment and/or another chemical or geometric treatment may also be provided in the same zone, or a portion thereof, although not specifically stated for each zone in the examples below. The zones may also have any suitable size and/or shape and are not limited by the examples illustrated below.

Figure 15:
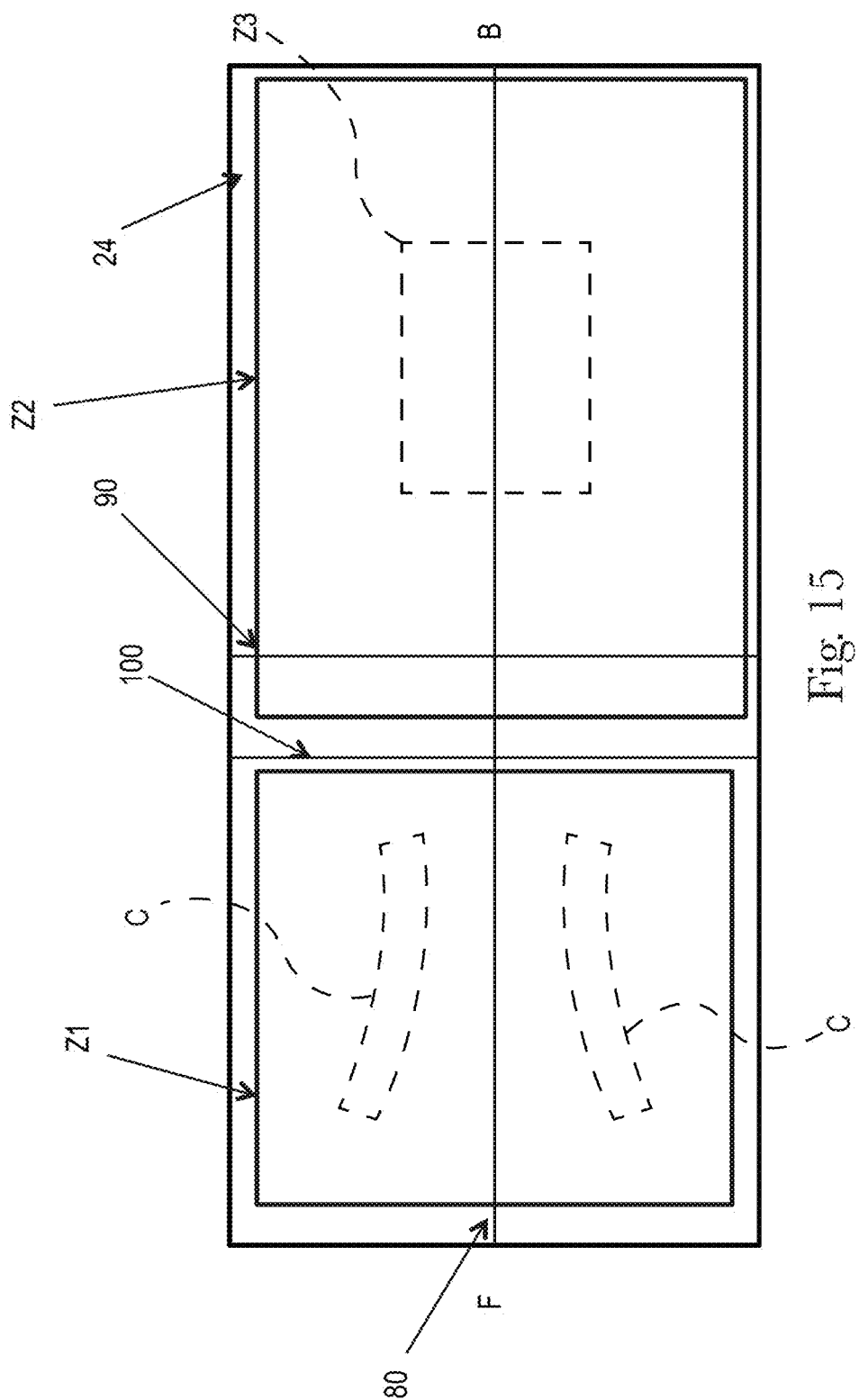
FIGS. 15-17 illustrate examples topsheets (and LMSs if interpenetrating the topsheets) having two zones, each zone having one or more treatments or no treatments, in accordance with the present disclosure.

Referring to FIG. 15, the topsheet 24 comprises a first zone Z1 in the front of the absorbent article and a second zone Z2 at least partially in the back of the absorbent article. Zone Z1 is positioned on a first side of the substantially laterally-extending separation element 100 (e.g., a recess, a raised portion, a structural separator, a printed line or graphic) and zone Z2 is positioned on a second side of the substantially laterally-extending separation element 100. Zones Z1 and Z2 may both overlap the longitudinal axis 80 and only zone Z2 may overlap the lateral axis 90. In other instances, only zone Z1 may overlap the lateral axis 90. In the example of FIG. 15, the substantially laterally-extending separation element 100 may be optional. The first and second zones Z1 and Z2 may each comprise any number of geometric, morphological, chemical treatments and/or flow control materials, or one of the zones Z1 or Z2, or portions thereof, may not comprise a treatment or a flow control material at all. Either of, or both of, zones Z1 or Z2 may also comprise apertures.

Referring again to FIG. 15, the substantially laterally-extending separation element 100 may define a visual front portion and a visual back portion on either side thereof. The visual front portion comprises zone Z1 and the visual back portion comprises zone Z2. Zone Z1 may comprise a first geometric treatment and zone Z2 may comprise a second geometric treatment. The first and second geometric treatments may be the same or different. The first and second geometric treatments may comprise elements that differ in depth, length, frequency, size, shape, pattern, dimensions, and/or structure. Either of the first and second geometric treatments may comprise apertures or morphological treatments (see e.g., FIGS. 52 and 54). The apertures may be different or the same in either of the treatments. The morphological treatments may be the same or different. The topsheet 24 may comprise a third geometric treatment Z3 (illustrated in dash) in either of the zones Z1 or Z2. A portion of an absorbent core and/or a liquid management system may have one or more channels, C, defined therein. A portion of the zones Z1 and/or Z2 may or may not overlap at least a portion of, or all of the channel(s).

Referring again to FIG. 15, the topsheet 24 may comprise zone Z1 at least partially in the front region (i.e., first side of the lateral axis 90) and a zone Z2 at least partially in the back region (i.e., second side of the lateral axis 90). Zone Z1 may comprise a first morphological treatment configured for urine handling and zone Z2 may comprise a second morphological treatment configured for BM handling. A pattern of the first morphological treatment in zone Z1 may be nonsymmetrical or symmetrical to a pattern of the second morphological treatment in zone Z2 about the lateral axis 90. Either of the zones Z1 and Z2 may have apertures defined therein. The apertures may have any suitable effective aperture areas and the topsheet 24 may have any suitable % open areas in the various zones. The first and second morphological treatments may be those illustrated in FIG. 52 or 54 hereof, for example. Either or both of the zones Z1 or Z2 may comprise a chemical treatment or a third morphological treatment. An area of zone Z1 may be smaller or larger than an area of zone Z2. Zone Z1 may have a dimension of at least 30 mm or at least 40 mm measured in a direction parallel to the lateral axis 90 and zone Z2 may have a dimension of at least 30 mm or at least 40 mm measured in the direction parallel to the lateral axis 90. Although not illustrated in FIG. 15, the absorbent article may comprise barrier leg cuffs and a waist edge.

Still referring to FIG. 15, zone Z1 may comprise a substantially transferrable chemical treatment and zone Z2 may comprise a substantially transferrable chemical treatment. The substantially transferrable chemical treatments may be the same or different. A basis weight of the substantially transferrable chemical treatment in zone Z2 may be greater than, less than, substantially the same as, or the same as, the substantially transferrable chemical treatment in zone Z1. The substantially transferrable chemical treatment may comprise a skin care composition or a BM anti-stick lotion. At least one of the zones Z1 or Z2 may also comprise a substantially durable chemical treatment. The substantially durable chemical treatment may comprise a pigment or an ink, for example. The zones Z1 and Z2 (or Z3) may also comprise one or more morphological or geometric treatments. The chemical treatments may or may not overlap with the morphological or geometric treatments. Zone Z1 or Z2 may comprise at least a third chemical treatment (e.g., Z3 in FIG. 15) that may either be substantially transferrable or substantially durable. Any of the chemical treatments may overlap at least a portion of, or all of, one or more channels C. In other instances, the various chemical treatments may not overlap any of the channels C. The substantially transferrable chemical treatment in zone Z1 may be hydrophobic and the substantially transferrable chemical treatment in zone Z2 may have a different hydrophilicity. The substantially transferrable chemical treatment in zone Z1 may be more hydrophilic or more hydrophobic than the substantially transferrable chemical treatment in zone Z2. In other instance, the substantially transferrable chemical treatment in zone Z2 may be hydrophobic or hydrophilic. The substantially transferrable chemical treatments may overlap or not overlap with one or more morphological treatments (see e.g., FIGS. 52 and 54 hereof) or one or more geometrical treatments.

Again referring to FIG. 15, zone Z1 may comprise a substantially durable chemical treatment and zone Z2 may comprise a substantially durable chemical treatment. The substantially durable chemical treatments may be the same or different. A basis weight of the substantially durable chemical treatment in zone Z2 may be greater than, less than, or the same as, the substantially durable chemical treatment in zone Z1. One both of the zones Z1 or Z2 may also comprise a substantially transferrable chemical treatment.

In other instances, one of the zones Z1 or Z2 may comprise a substantially durable chemical treatment and the other of the zones may comprise a substantially transferrable chemical treatment.

Figure 16:
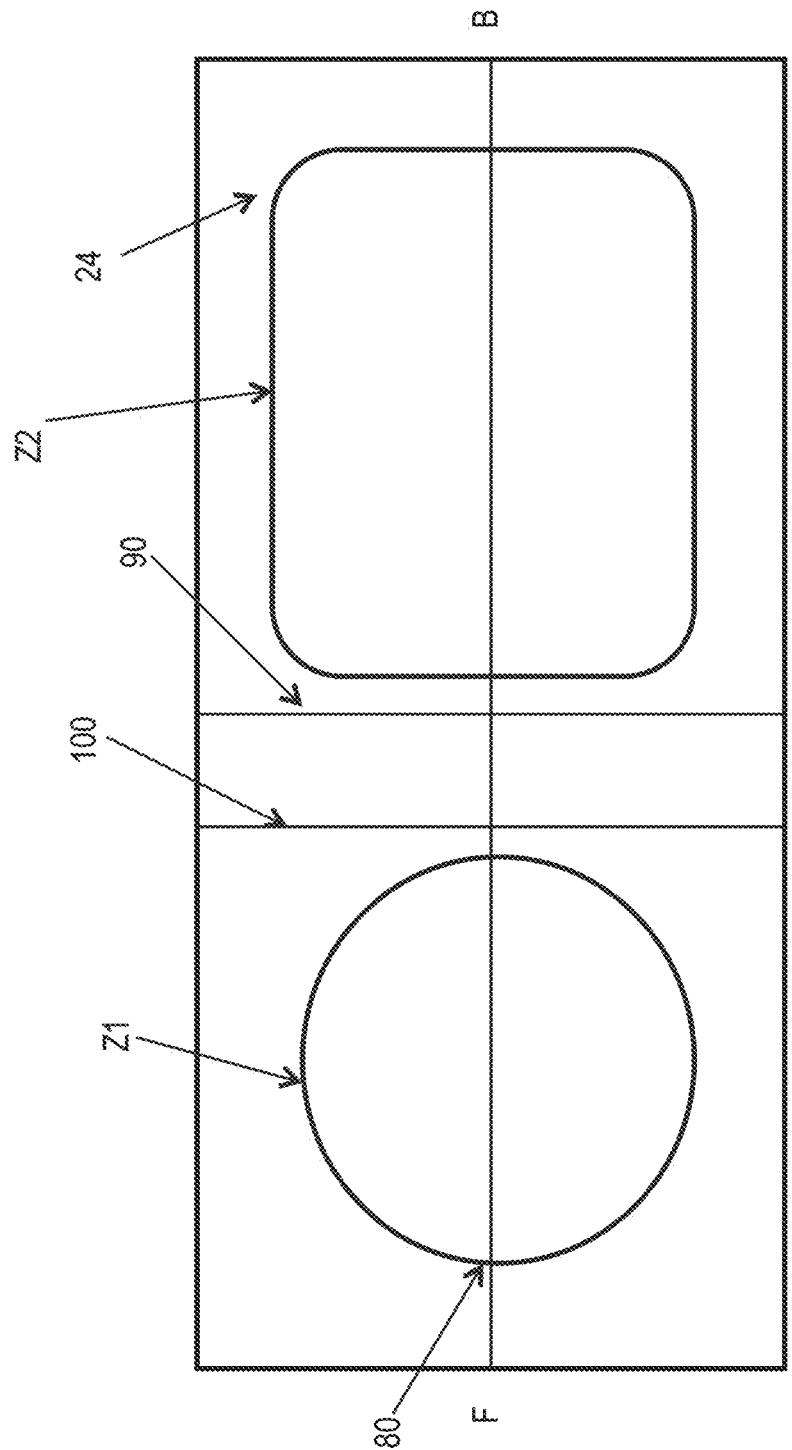

Referring to FIG. 16, the topsheet 24 comprises a first zone Z1 in the front of the absorbent article and a second zone Z2 in the back of the absorbent article. Zone Z1 is positioned on a first side of the substantially laterally-extending separation element 100 and zone Z2 is positioned on a second side of the substantially laterally-extending separation element 100. In the example of FIG. 16, the substantially laterally-extending separation element 100 may be optional. Zones Z1 and Z2 may both overlap the longitudinal axis 80 and neither of the zones Z1 and Z2 may overlap the lateral axis 90. In other instances, only zone Z1 or only zone Z2 may overlap the lateral axis 90. The first and second zones Z1 and Z2 may comprise any number of geometric, morphological, chemical treatments and/or flow control materials, or one of the zones Z1 or Z2, or portions thereof, may not comprise a treatment or a flow control material at all. Either of zones Z1 or Z2 may also comprise apertures.

Figure 17:
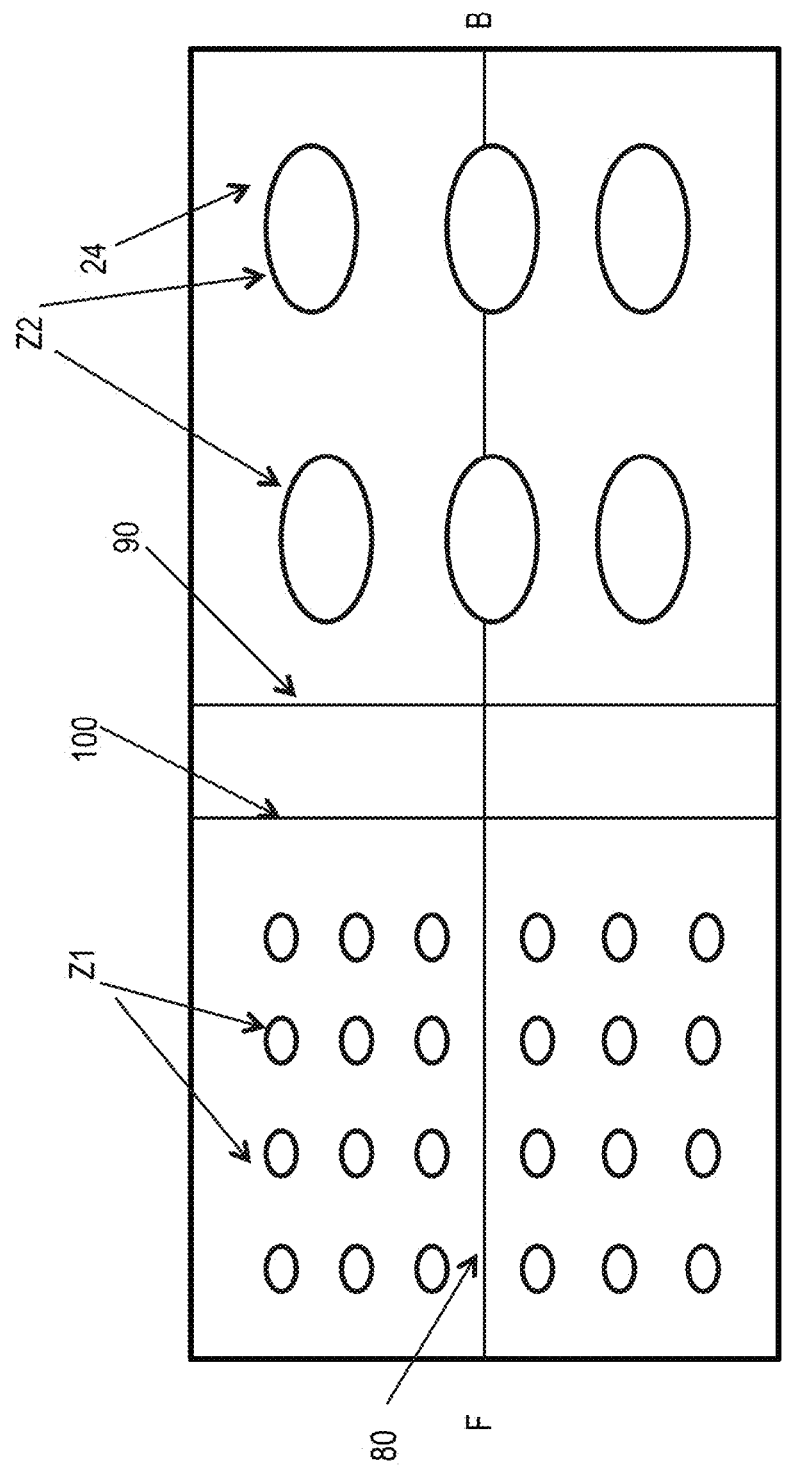

Referring to FIG. 17, the topsheet 24 comprises a first zone Z1 comprising a plurality of elements in the front portion of the absorbent article and a second zone Z2 comprising a plurality of elements in the back portion of the absorbent article. Zone Z1 is positioned on a first side of the substantially laterally-extending separation element 100 and zone Z2 is positioned on a second side of the substantially laterally-extending separation element 100. In the example of FIG. 17, the substantially laterally-extending separation element 100 may be optional. The elements of the first zone Z1 do not overlap the lateral axis 90 or the longitudinal axis 80 and some of the elements of the second zone Z2 overlap only the longitudinal axis. It is within the scope of the present disclosure to have at least some of the elements of either zone overlap or not overlap one of the axes 80 or 90. The elements that make up zones Z1 and Z2 may comprise a plurality of apertures. The apertures in zone Z1 may be smaller than the apertures in zone Z2 or vice versa. The smaller apertures in zone Z1 may be configured for urine management, while the larger apertures in zone Z2 may be configured for BM management. Example effective aperture areas and example % effective open areas are described herein. While the apertures of the first and second zones Z1 and Z2 are illustrated as generally ovate, they may have any suitable size, shape, and/or pattern. In other instances, the elements that make up zones Z1 and/or Z2 may not form apertures and instead they may comprise one or more other treatments and/or flow control materials.

Figure 18:
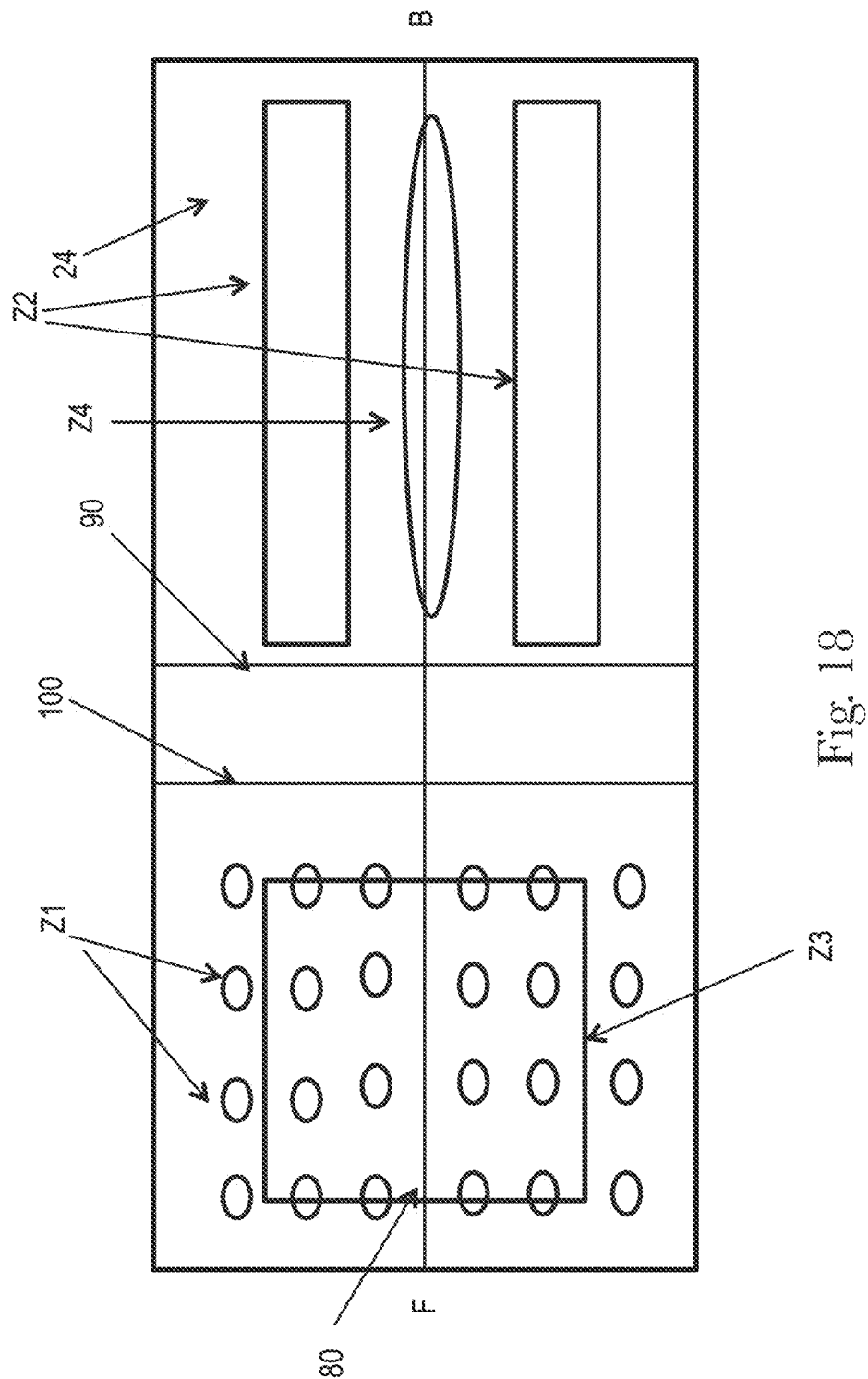
FIGS. 18 and 19 illustrate examples topsheets (and LMSs if interpenetrating the topsheets) having four zones, each zone having one or more treatments or no treatments, in accordance with the present disclosure.

Referring to FIG. 18, the topsheet 24 has a first zone Z1 comprising a plurality of elements in the front of the absorbent article and a second zone Z2 comprising a plurality of elements in the back portion of the absorbent article. The topsheet 24 also has a third zone Z3 in the front of the absorbent article and a fourth zone Z4 in the back of the absorbent article. Zones Z1 and Z3 are positioned on a first side of the substantially laterally-extending separation element 100 and a first side of the lateral axis 90 and zones Z2 and Z4 are positioned on a second side of the substantially laterally-extending separation element 100 and on a second side of the lateral axis 90. The elements of the first and second zones Z1 and Z2 do not overlap the lateral axis 90 or the longitudinal axis 80 and the third and fourth zones Z3 and Z4 do not overlap the lateral axis 90, but do overlap the longitudinal axis. It is within the scope of the present disclosure to have any of the zones (or elements forming the zones) overlap or not overlap one of the axes 80 or 90. Zone Z1 may comprise a plurality of elements that are apertures or that comprise another treatment or flow control material. Zone Z4 may comprise one large aperture, embossment, or other treatment, such as a chemical treatment or a flow control material, for example. The apertures in zone Z1 may be smaller than the aperture of zone Z4. The smaller apertures in zone Z1 may be configured for urine management, while the large aperture in zone Z4 may be configured for BM management. Zone Z3 overlaps at a least a portion of zone Z1 while zones Z2 and Z4 do not overlap with any other zone. It is within the scope of the present disclosure to have any of the various zones in any of the zonal examples to overlap or not overlap each other.

Figure 19:
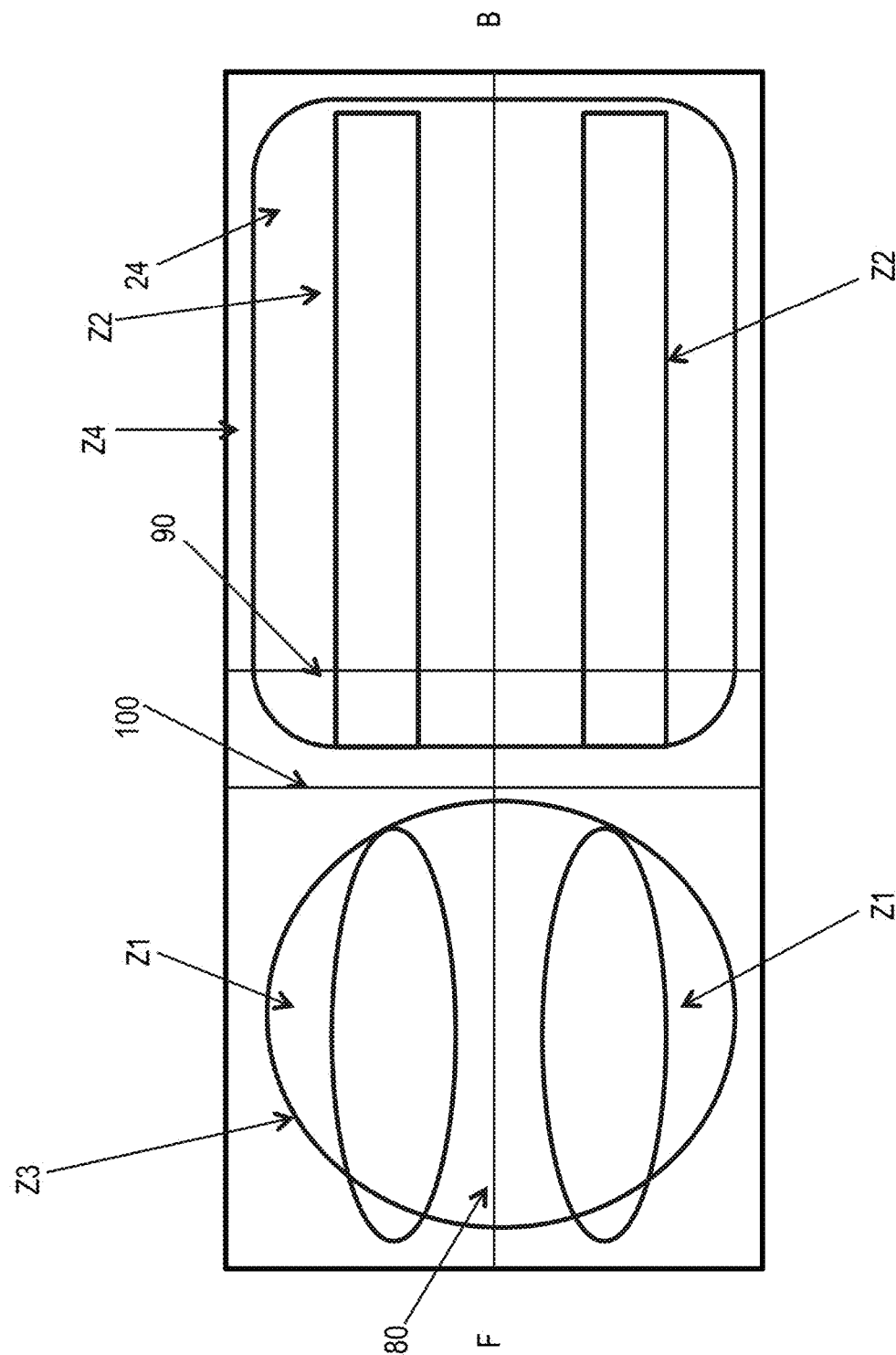

Referring to FIG. 19, the topsheet 24 comprises a first zone Z1 comprising a plurality of elements in the front of the absorbent article and a second zone Z2 comprising a plurality of elements at least partially in the back of the absorbent article. The topsheet 24 comprises a third zone Z3 in the front of the absorbent article and a fourth zone Z4 at least partially in the back of the absorbent article. Zones Z1 and Z3 are positioned on a first side of the substantially laterally-extending separation element 100 and zones Z2 and Z4 are positioned on a second side of the substantially laterally-extending separation element 100. The first and second zones Z1 and Z2 do not overlap the longitudinal axis 80 and the second and fourth zones Z2 and Z4 overlap the lateral axis 90. The fourth zone Z4 overlaps the lateral axis 90 and the longitudinal axis 80. It is within the scope of the present disclosure to have any of the zones overlap or not overlap one of the axes 80 or 90. The elements of zone Z1 may be apertures, or not. Zone Z3 overlaps at a least a portion of zone Z1 and zone Z4 overlaps at least a portion of zone Z2.

Figure 20:
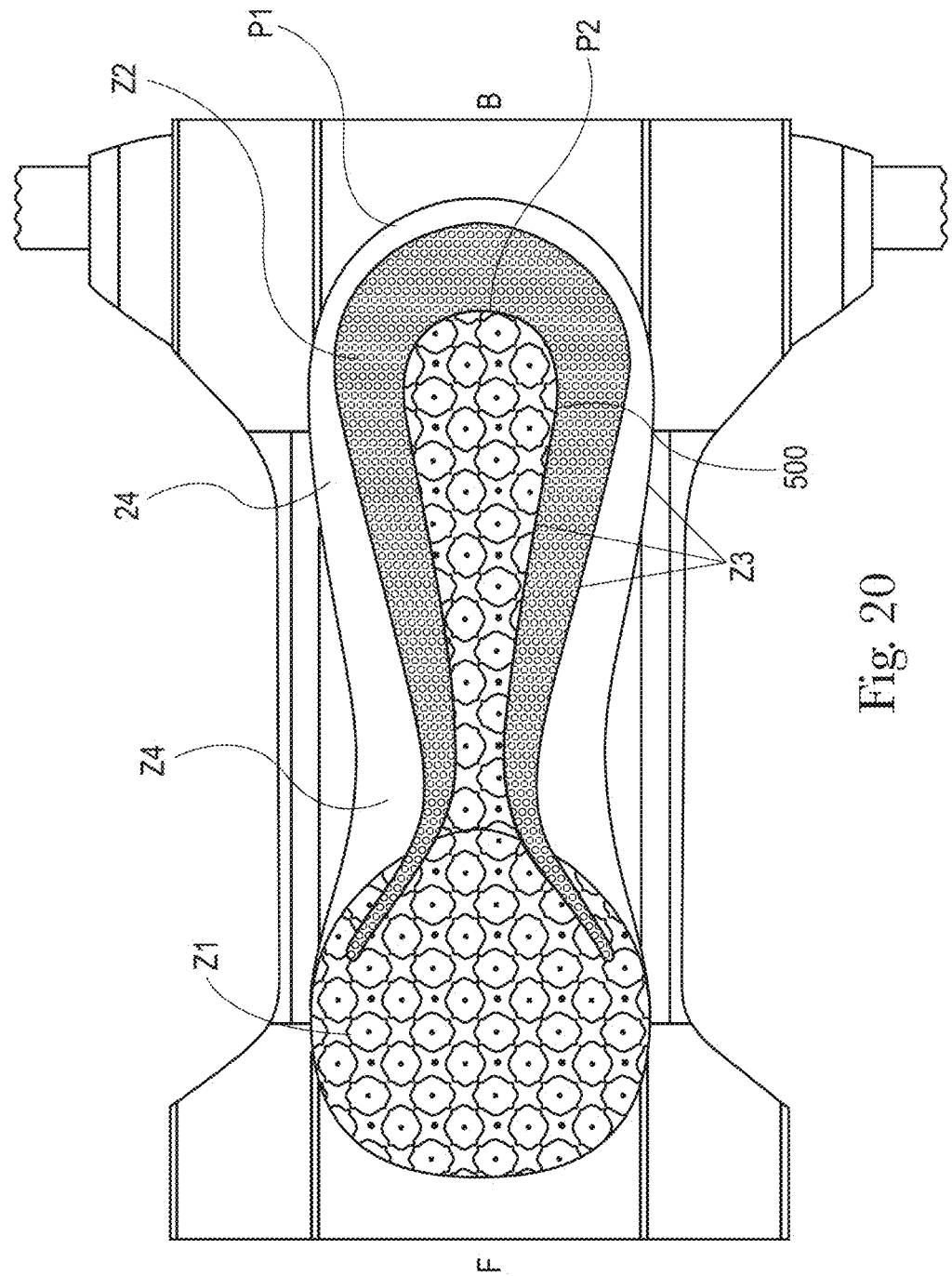
FIGS. 20 to 21C illustrate example topsheets (and LMSs if interpenetrating the topsheets) having three or more zones, each zone having one or more treatments or no treatments, in accordance with the present disclosure.

Referring to FIG. 20, a topsheet 24 of an absorbent article is illustrated with four zones, Z1-Z4. The zones Z1-Z4 may comprise any number of geometric, morphological, and/or chemical treatments or flow control materials, or one or more of the zones, or portions thereof, may not comprise a treatment or a flow control material at all. Zone Z3 may comprise deep emboss lines. Zone Z1 may comprise a morphological treatment (e.g., see FIG. 52 or 54) and/or a printed pattern. Zone Z2 may comprise a morphological treatment (e.g., see FIG. 52 or 54). Zone 4 may not comprise a treatment or may comprise a flow control material. Zone Z3 may also comprise a flow control material at least partially forming an enclosed perimeter over at least a portion of an absorbent core of the absorbent article.

Referring to FIG. 20A, a topsheet 24 of an absorbent article is illustrated with five zones, Z1-Z5. Zones Z1 and Z5 may comprise a morphological treatment (e.g., see FIG. 52 or 54). Zone Z2 may comprise a flow control material for urine, for example. The flow control material may form a fully enclosed perimeter within the topsheet 24. Zone Z3 may comprise a morphological treatment (e.g., FIG. 52 or 54), a printed pattern, and/or a flow control material. Zone Z4 may comprise a flow control material for BM, for example that may form a partially enclosed perimeter within the topsheet 24. Any of the zones may also comprise one or more additional treatments and/or flow control materials.

Figure 21:
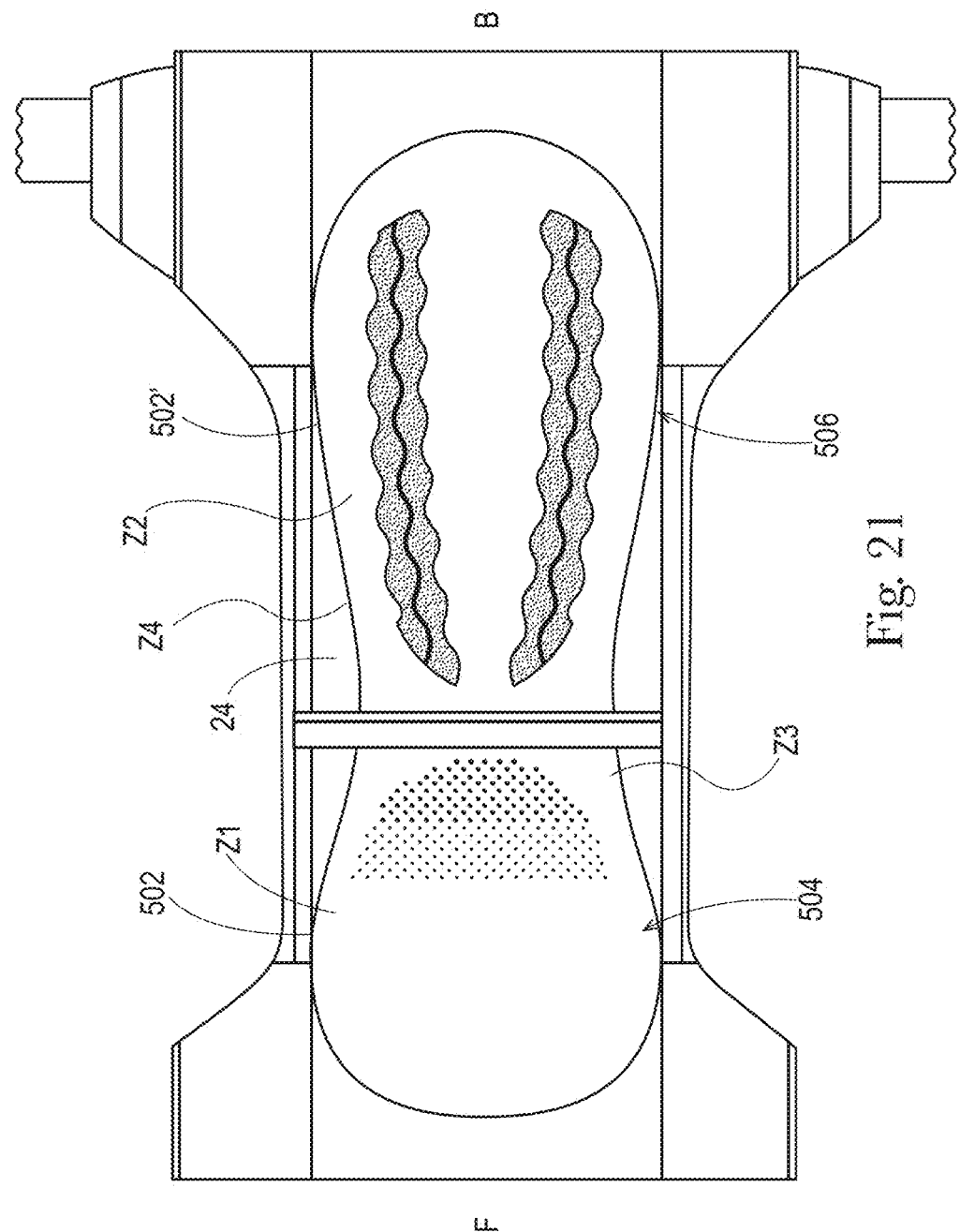

Referring to FIG. 21, an absorbent article comprising a topsheet 24 is illustrated with four zones Z1-Z4. Zone Z1 may comprise a chemical treatment of printed dots and/or a geometric treatment of apertures. Zone Z2 may comprise a chemical treatment of printed diamonds and/or a morphological treatment of puckering. Zone Z2 may also comprise apertures. Zone Z3 may or may not have a treatment. Zone Z4 may comprise a flow control material forming a fully enclosed, continuous perimeter in the topsheet and over a portion of the absorbent core. Although not illustrated, the enclosed perimeter of Zone Z4 may also be discontinuous or may only form an at least mostly enclosed perimeter over a portion of the absorbent core.

Referring to FIG. 21A, an absorbent article comprising a topsheet 24 is illustrated with five zones Z1-Z5. Zone Z1 may comprise a hydrophobic skin care composition. Zone Z2 may comprise a morphological treatment (see e.g., FIG. 52 or 54). Zone Z3 may comprise a morphological treatment (see e.g., FIG. 52 or 54). Zone Z4 may comprise a skin care composition that is more or less hydrophobic than the skin care composition of Zone Z1. Zone Z5 may comprise an embossed FIG. 8-like shape and/or a flow control material forming an enclosed, continuous perimeter. The continuous perimeter may surround one or more urine and/or BM insult zones (e.g., Zones Z1 and Z3). Although not illustrated, the perimeter may be discontinuous and at least mostly enclosed. Any of the zones may also comprise one or more additional treatments and/or flow control materials. The absorbent article may optionally comprise a lateral separation element LSE.

Figure 21B:
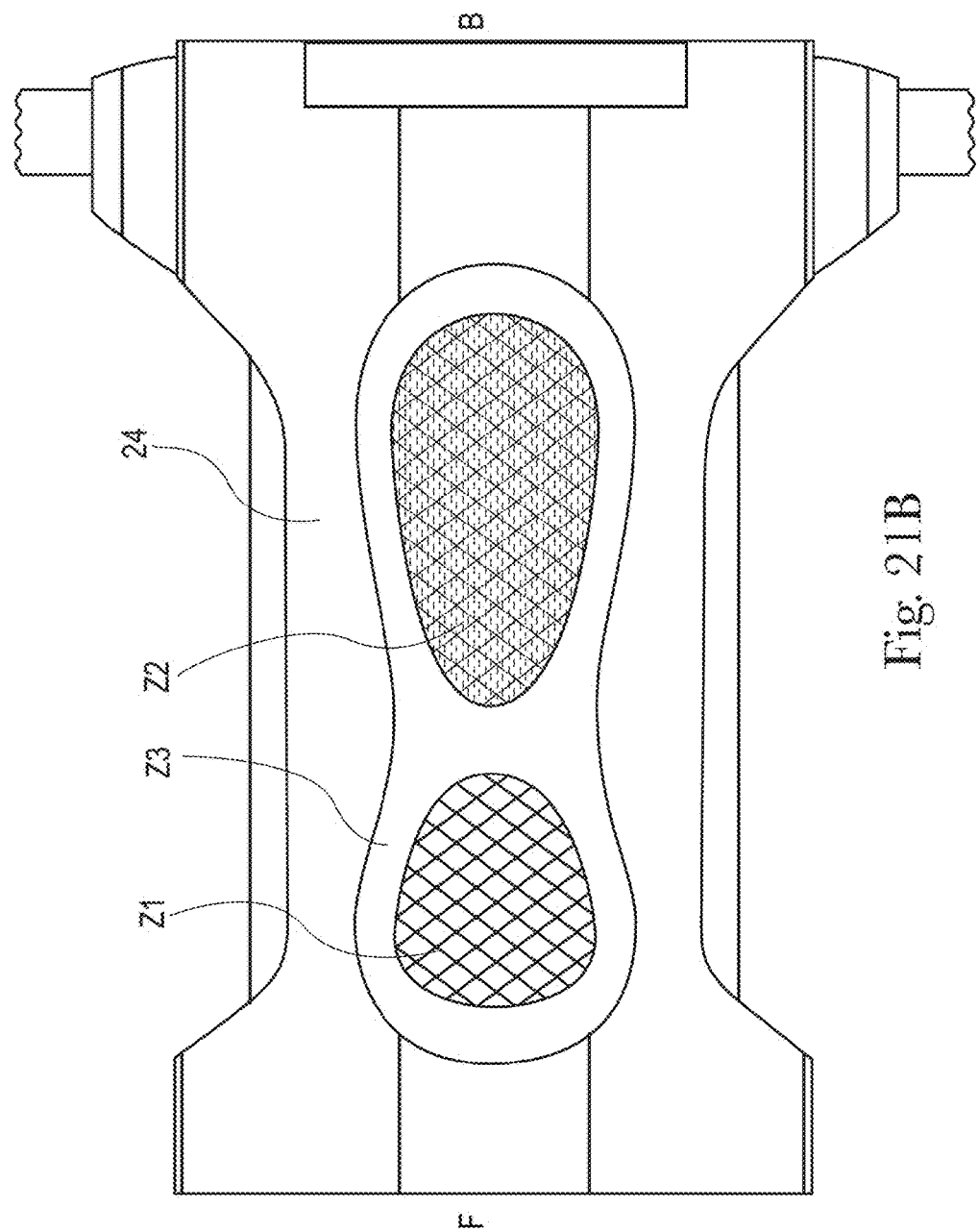

Referring to FIG. 21B, an absorbent article comprising a topsheet 24 is illustrated with three zones Z1-Z3. Zone Z1 may comprise a morphological treatment (see e.g., FIG. 52 or 54) to provide absorbency and dryness during and after a urination event. Zone Z2 may comprise a morphological treatment (see e.g., FIG. 52 or 54) to at least inhibit BM spreading. Zone Z3 may comprise a flow control material. The flow control material may form an enclosed perimeter around two bodily exudate receiving zones. The flow control material may be continuous or discontinuous. Any of the zones may also comprise one or more additional treatments and/or flow control materials. The absorbent article may optionally comprise a lateral separation element (not illustrated).

Figure 21C:
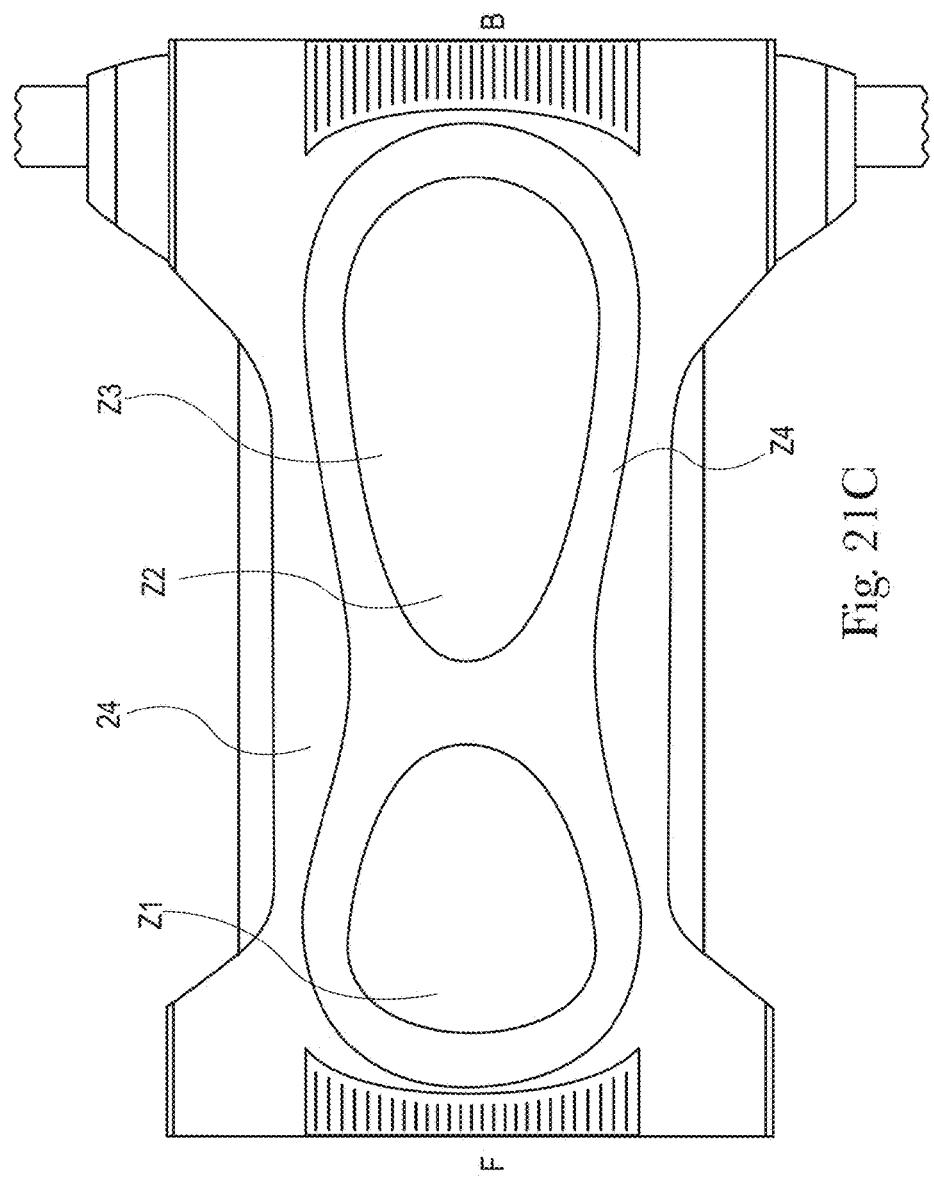

Referring to FIG. 21C, an absorbent article comprising a topsheet 24 is illustrated with four zones Z1-Z4. Zone Z1 may comprise a geometric treatment comprising apertures or may comprise a morphological treatment. The % effective open area of Zone Z1 may be about 5% to about 20% or about 10%. Zone Z2 may comprise a geometric treatment comprising apertures or may comprise a morphological treatment. The % effective open area of Zone Z2 may be about 15% to about 50% or about 30%. Zone Z3 may comprise an anti-stick lotion. Zone Z4 may comprise a morphological treatment and/or may comprise a flow control material. Any of the zones may also comprise one or more additional treatments and/or flow control materials. The absorbent article may optionally comprise a lateral separation element (not illustrated).

Referring to FIG. 22, an absorbent article comprising a topsheet 24 is illustrated with six zones. Zone Z1 may comprise deep embossed lines, printed lines, flow control materials, and/or other treatments. Zones Z2 to Z5 may each comprise any number of chemical, geometric, and/or morphological treatments or no treatments at all. Some of the zones may form arcuate shapes.

Figure 23:
FIG. 23 is a photograph of the example topsheet (and LMS) of FIG. 22, in accordance with the present disclosure.

FIG. 23 is a photograph of an actual absorbent article comprising a topsheet similar to the example topsheet of FIG. 22.

Figure 24:
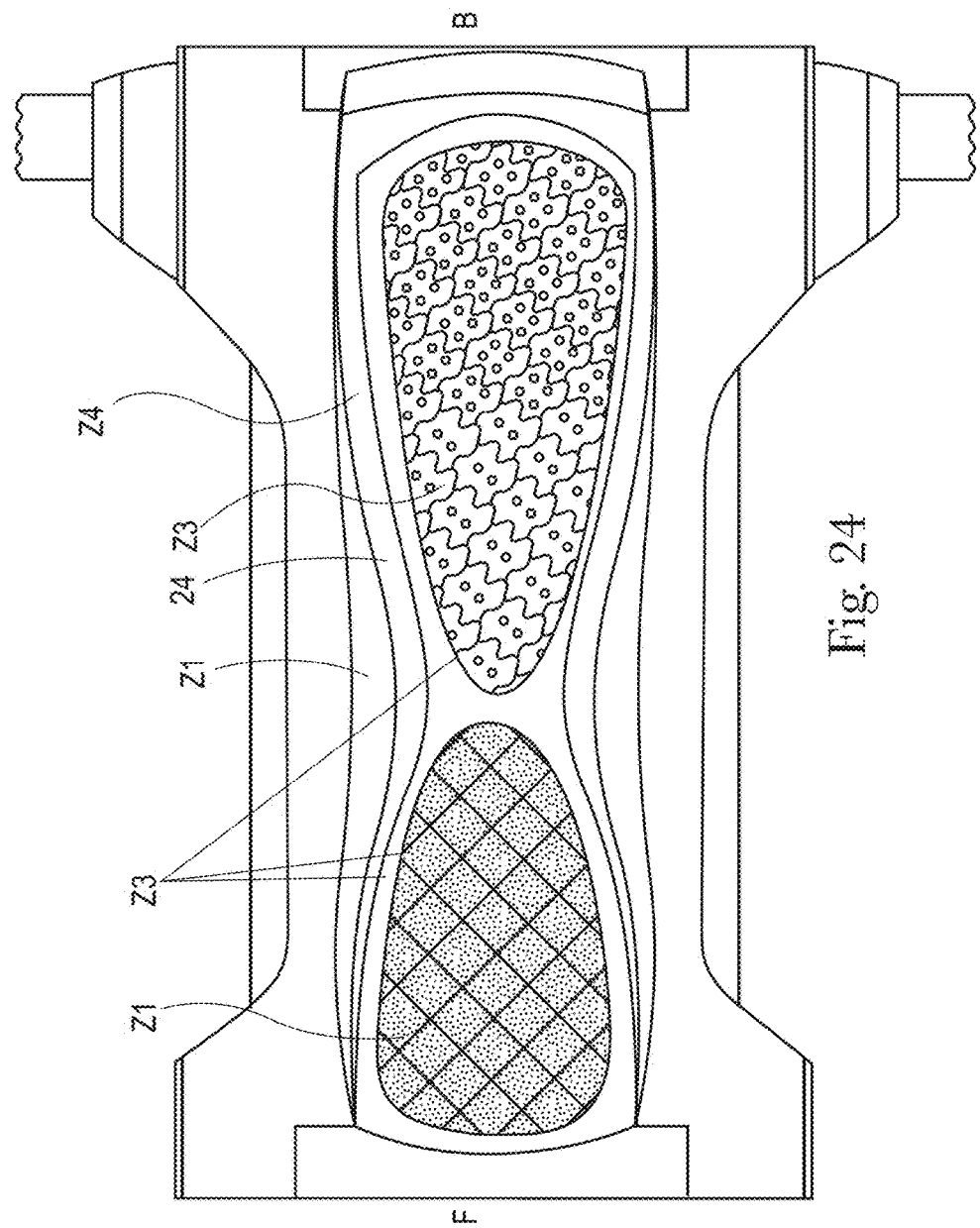
FIG. 24 is an example of a topsheet (and LMS if interpenetrating the topsheet) having five zones, each zone having one or more treatments or no treatments, in accordance with the present disclosure.

Referring to FIG. 24, an absorbent article comprising a topsheet 24 is illustrated with four zones. Zone Z1 may comprise a flow control material. Zone Z2 may comprise an embossing pattern or a printed pattern and/or one or more geometrical treatments. Zone Z3 may comprise embossing and/or a flow control material. Zone Z4 may have one or more treatments and/or flow control materials, or not. Any of zones Z1-Z4 may have one or more chemical treatments or other treatments.

Figure 25:
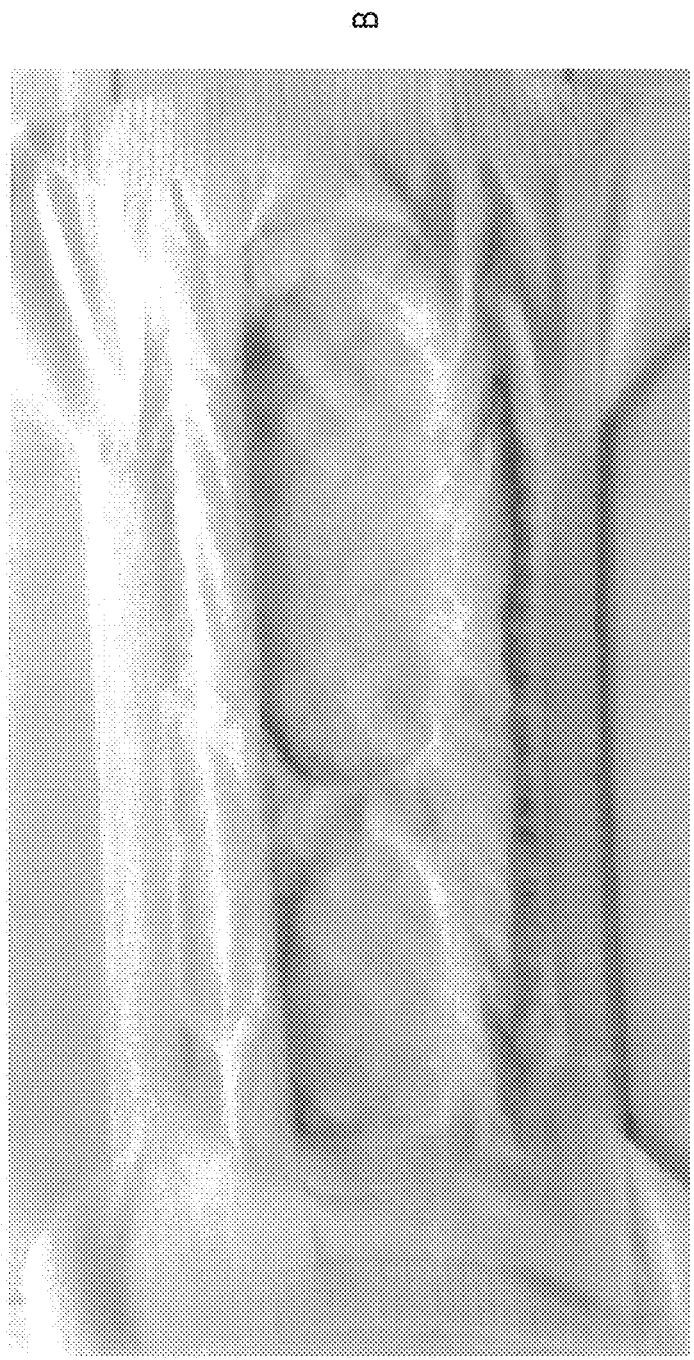
FIG. 25 is a photograph of the example topsheet (and LMS) of FIG. 24, in accordance with the present disclosure.

FIG. 25 is a photograph of an actual absorbent article comprising a zoned topsheet. The topsheet has at least two zones of embossing and may have other treatments.

Figure 26:
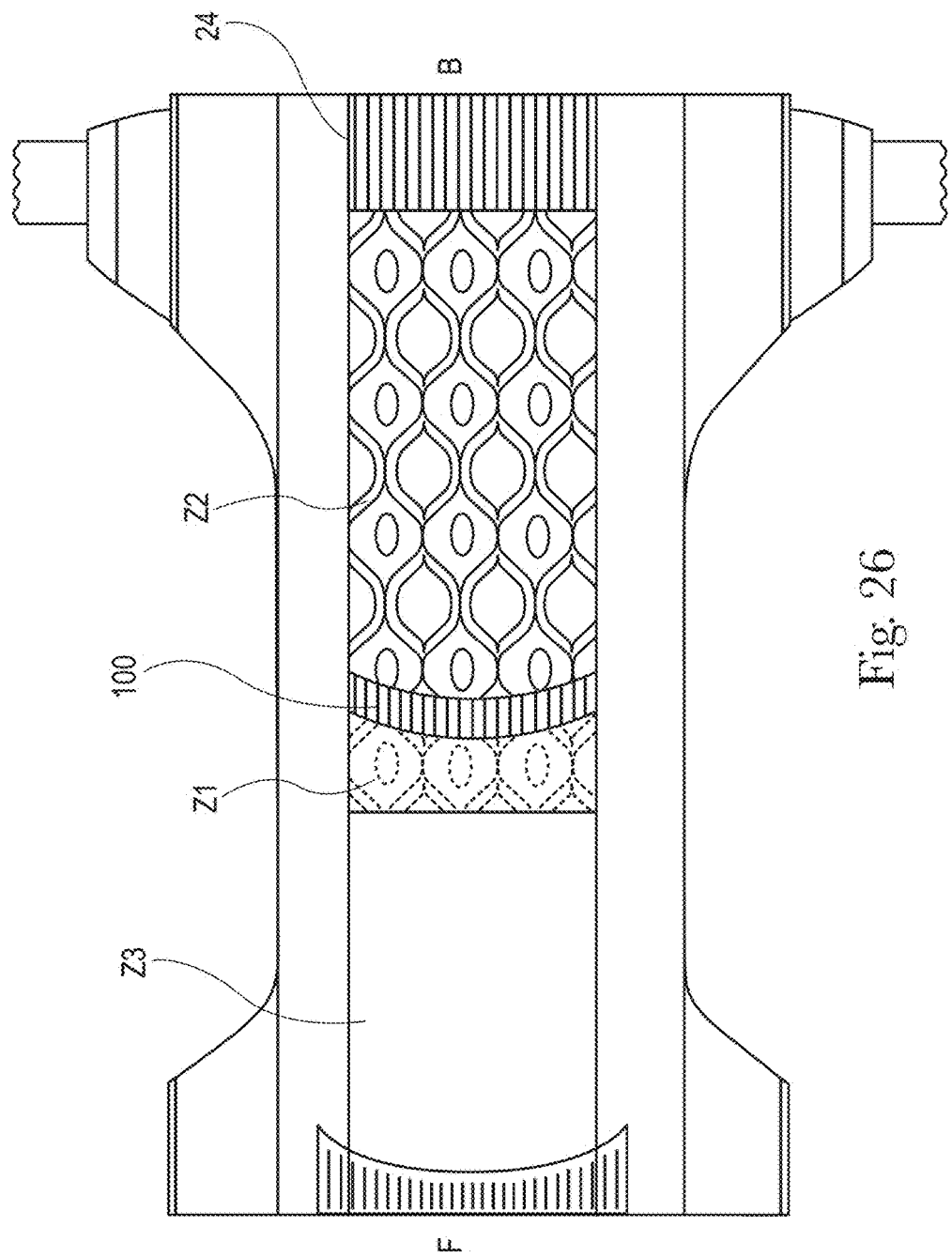
FIG. 26 is an example of a topsheet (and LMS if interpenetrating the topsheet) having four zones, each zone having one or more treatments or no treatments, in accordance with the present disclosure.

Referring to FIG. 26, an absorbent article comprising a topsheet 24 is illustrated with three zones. Zone Z1 may comprise embossing or other treatment having a first pattern, zone Z2 may comprise embossing or other treatment having a different pattern, and zone Z3 may comprise one or more treatments or may not. The article may also comprise a substantially laterally extending separation element.

Figure 27:
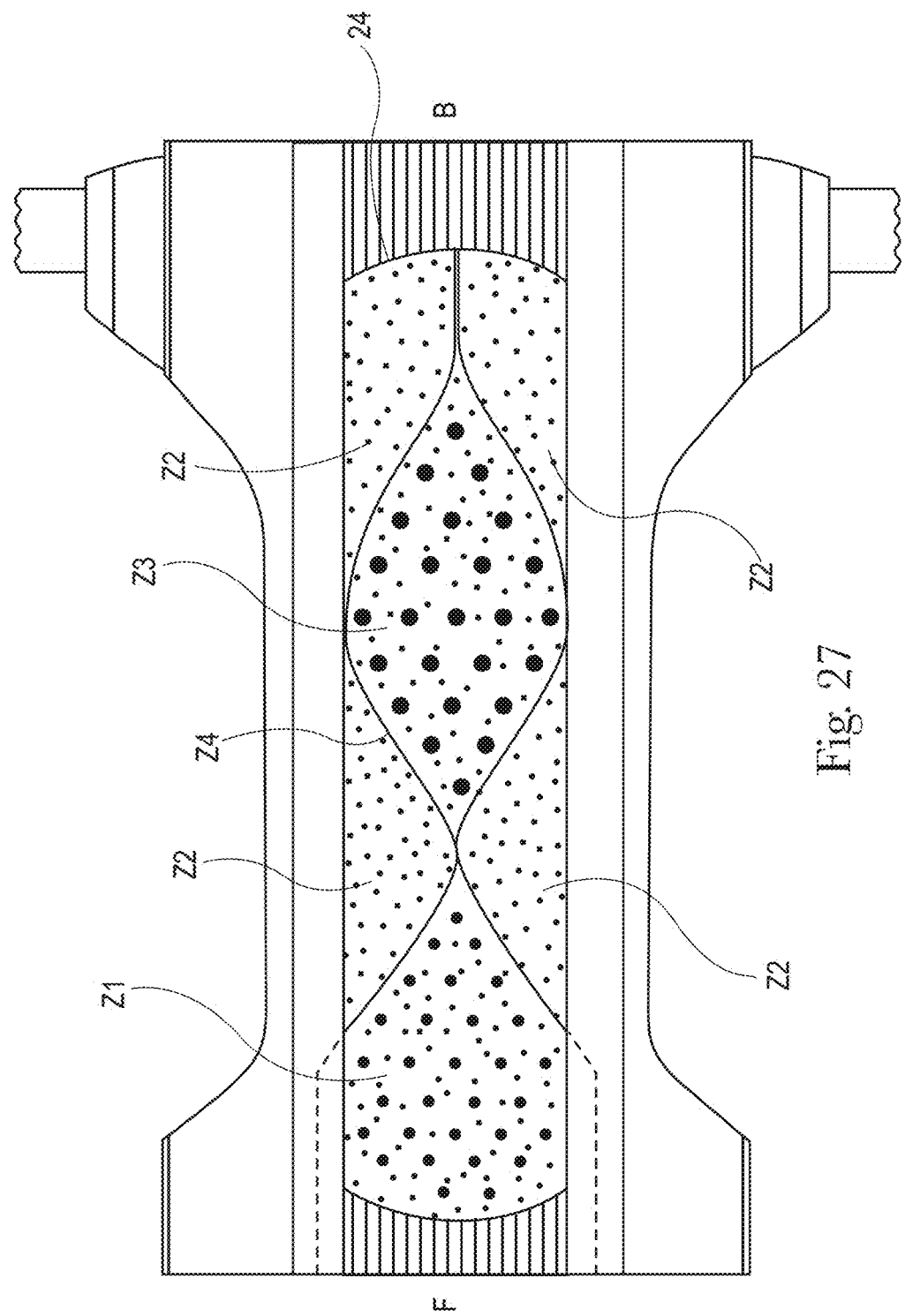
FIG. 27 is an example of a topsheet (and LMS if interpenetrating the topsheet) having four zones, each zone having one or more treatments or no treatments, in accordance with the present disclosure.

Referring to FIG. 27, an absorbent article comprising a topsheet 24 is illustrated with four zones. Zones Z1 and Z2 may each comprise a chemical treatment of small printed dots or may each comprise apertures. The dots and/or the apertures may be the same size or different sizes. The treatments in zones Z1 and Z2 may be same or different. Zone Z3 may comprise a chemical treatment of larger printed dots or apertures than the dots or apertures in zones Z1 and Z2. Zone Z4 may comprise fold lines, embossed lines, printed lines, a flow control material, or another treatment. The fold lines may be formed from portions of the topsheet or may be separate materials attached to the topsheet.

Figure 28:
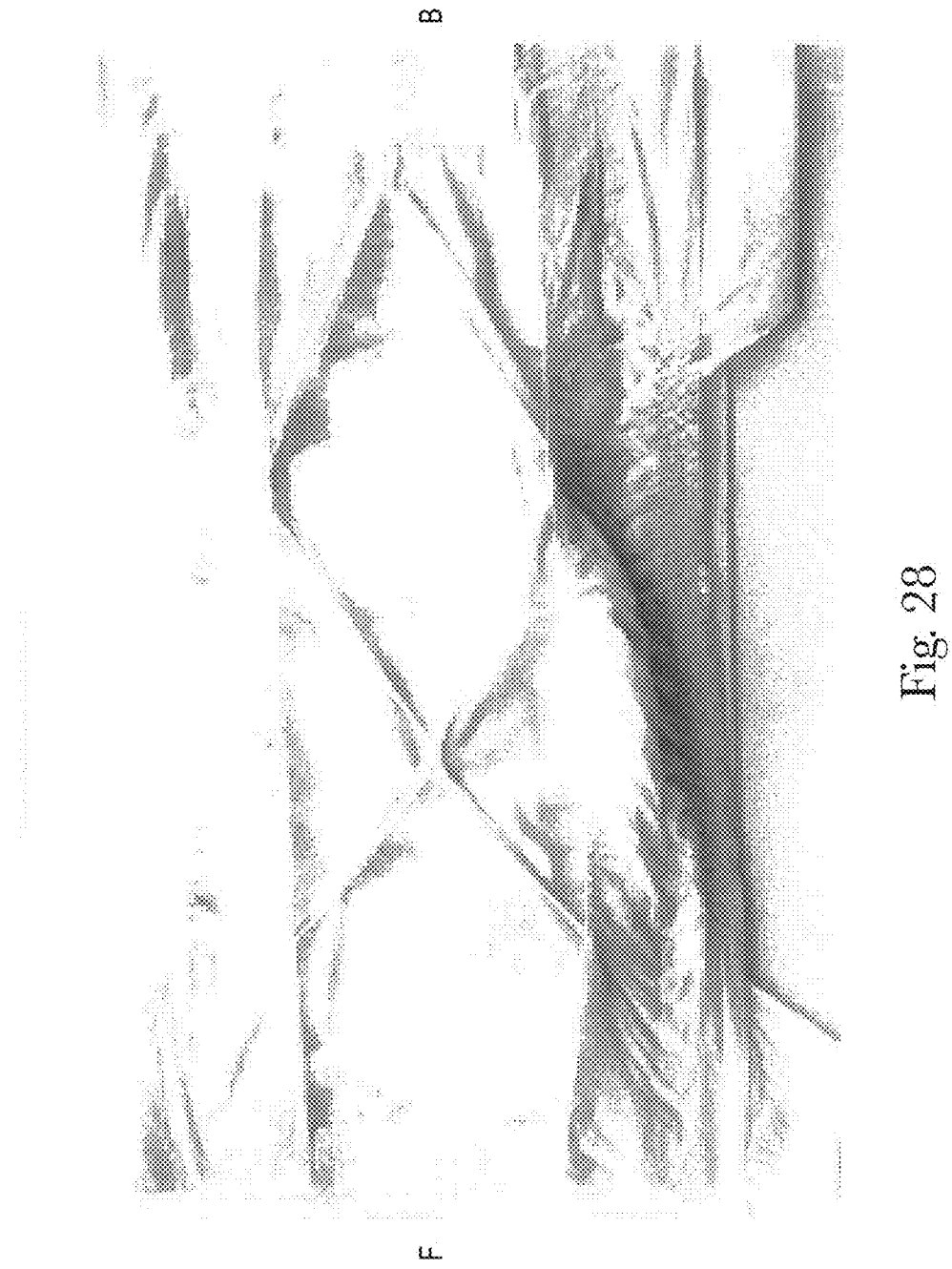
FIG. 28 is a photograph of the example topsheet (and LMS) of FIG. 27, in accordance with the present disclosure.

FIG. 28 is a photograph of an actual absorbent article comprising a topsheet somewhat similar to the example topsheet of FIG. 27.

Figure 29:
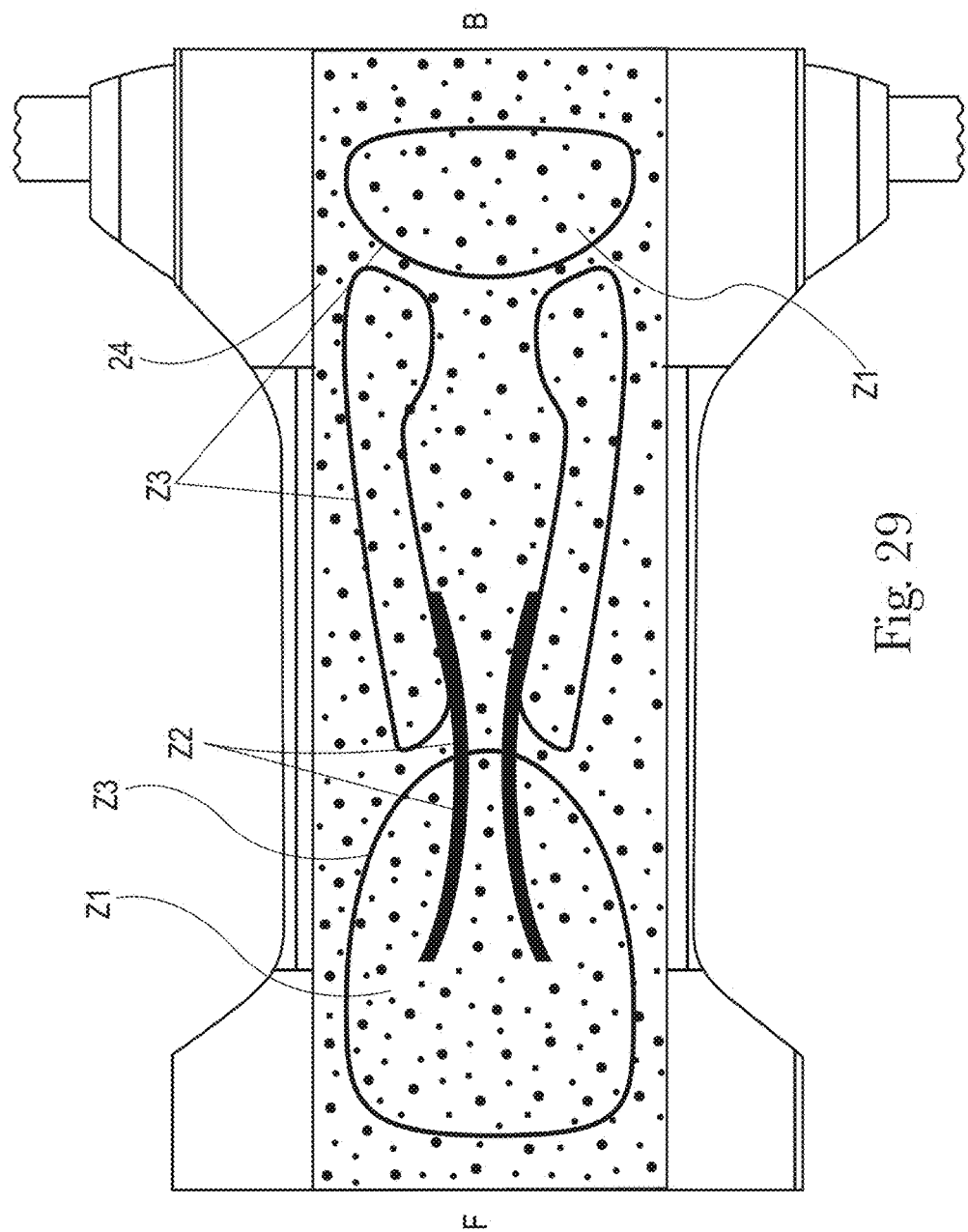
FIG. 29 is an example of a topsheet (and LMS if interpenetrating the topsheet) having four zones, each zone having one or more treatments or no treatments, in accordance with the present disclosure.

Referring to FIG. 29, an absorbent article comprising a topsheet 24 is illustrated with three zones. Zone Z1 may comprise a chemical treatment of small printed dots or may comprise apertures. Zone Z2 may comprise embossed lines, printed, lines or another treatment. Zone Z3 may comprise embossed lines, printed lines, or another treatment. Zone Z4 may comprise small printed dots or apertures.

Figure 30:
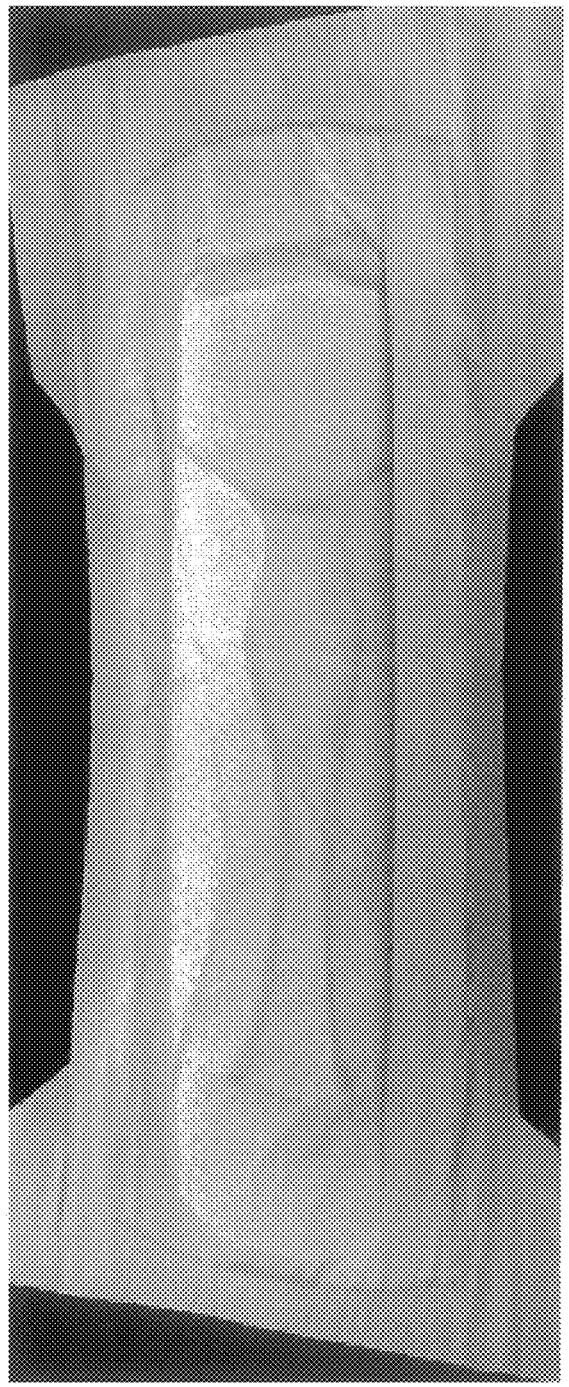
FIG. 30 is a photograph of the example topsheet (and LMS) of FIG. 29, in accordance with the present disclosure.

FIG. 30 is a photograph of an actual absorbent article comprising a topsheet similar to the example topsheet of FIG. 29.

Figure 31:
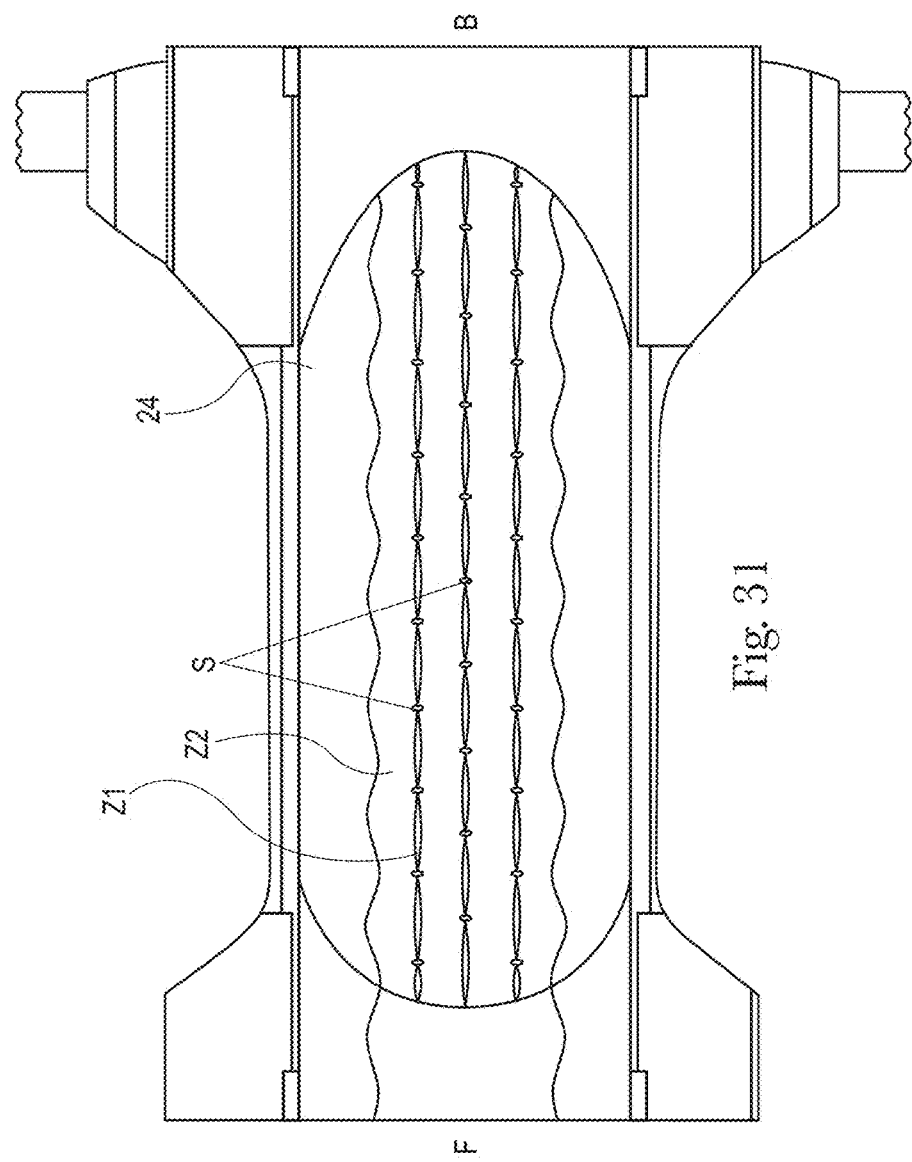
FIG. 31 is an example of a topsheet (and LMS if interpenetrating the topsheet) having two zones, each zone having one or more treatments or no treatments, in accordance with the present disclosure.

Referring to FIG. 31, an absorbent article comprising a topsheet 24 is illustrated with two zones. Zone Z1 may comprise slits. Zone Z2 may comprise folds, embossed lines, printed lines or no treatments. Either or both of the zones may also comprise a chemical treatment, such as a print. The pleats may be formed in a two layer topsheet. A first layer may be slit using a rotary die before or after the first layer is attached to a second layer. The first layer may be high pressure bonded to the second layer incrementally along the slits. The bond sites, S, may encompass a portion of the first layer on either side of the slits and attach the portions to the second layer.

Figure 32:
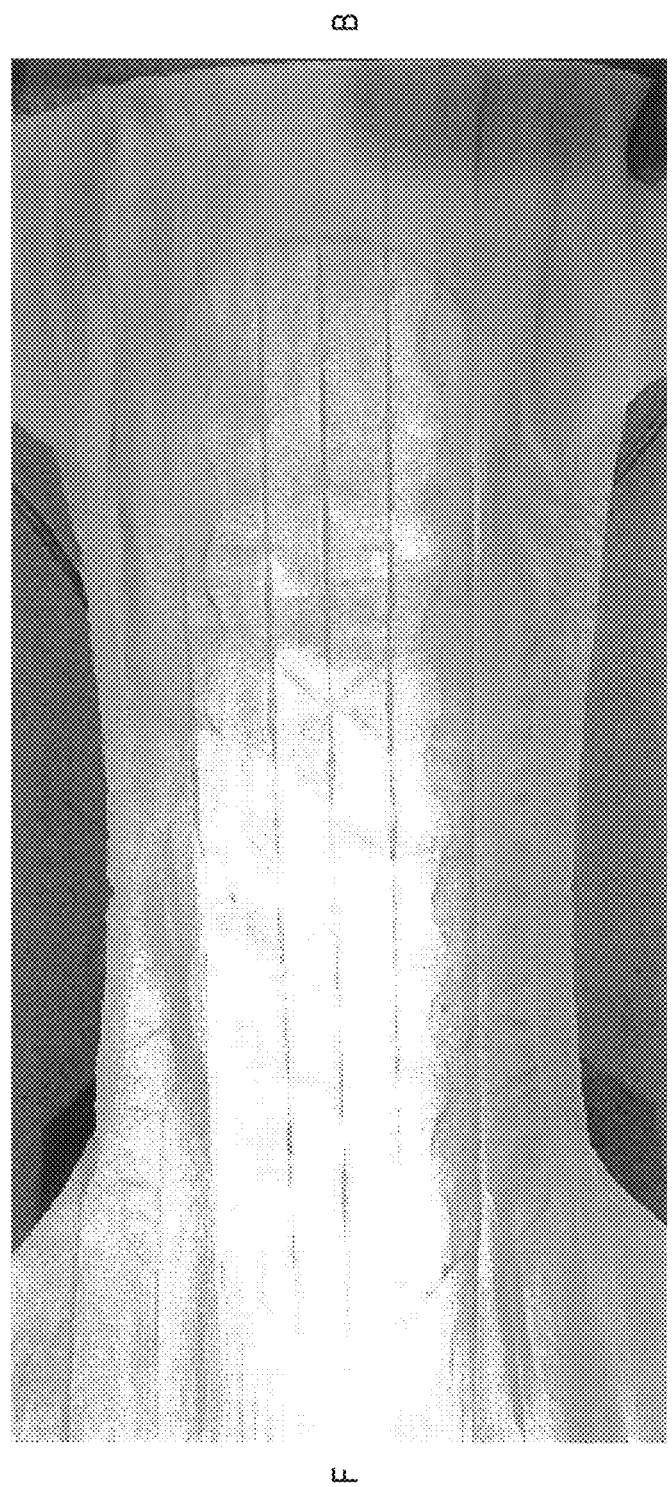
FIG. 32 is a photograph of the example topsheet (and LMS) of FIG. 31, in accordance with the present disclosure.
Figure 33:
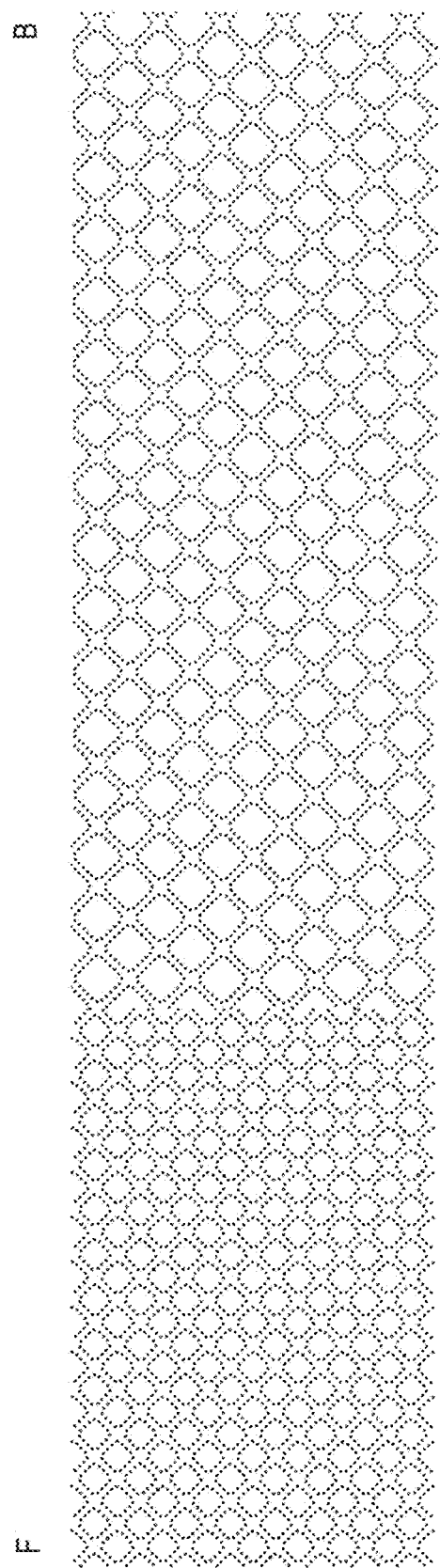
FIGS. 33-42 are example patterns of zonal topsheets in accordance with the present disclosure.
Figure 34:
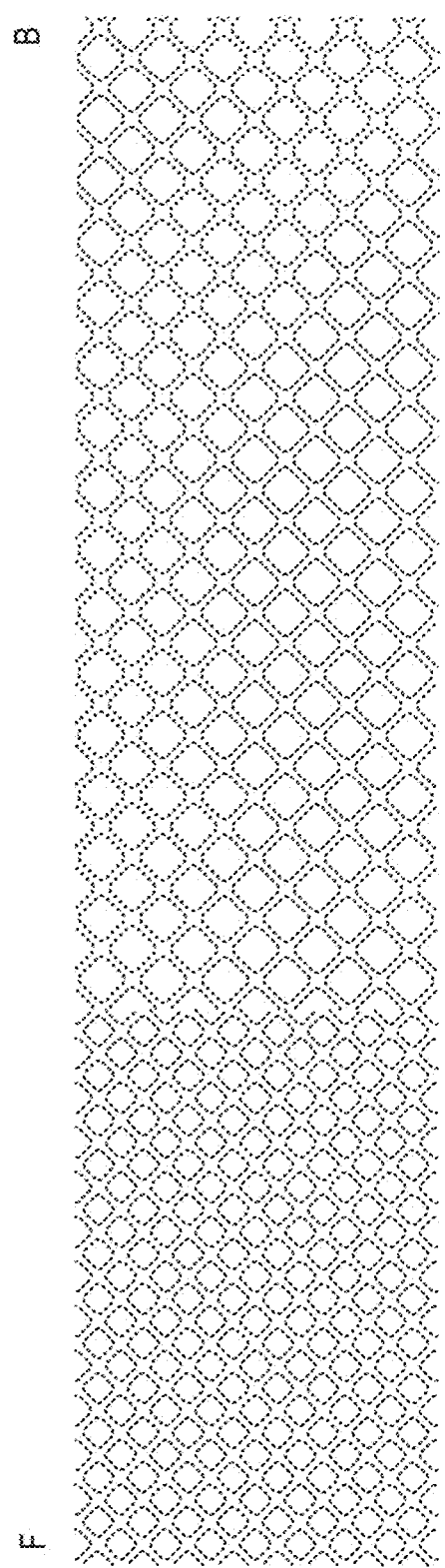
Figure 35:
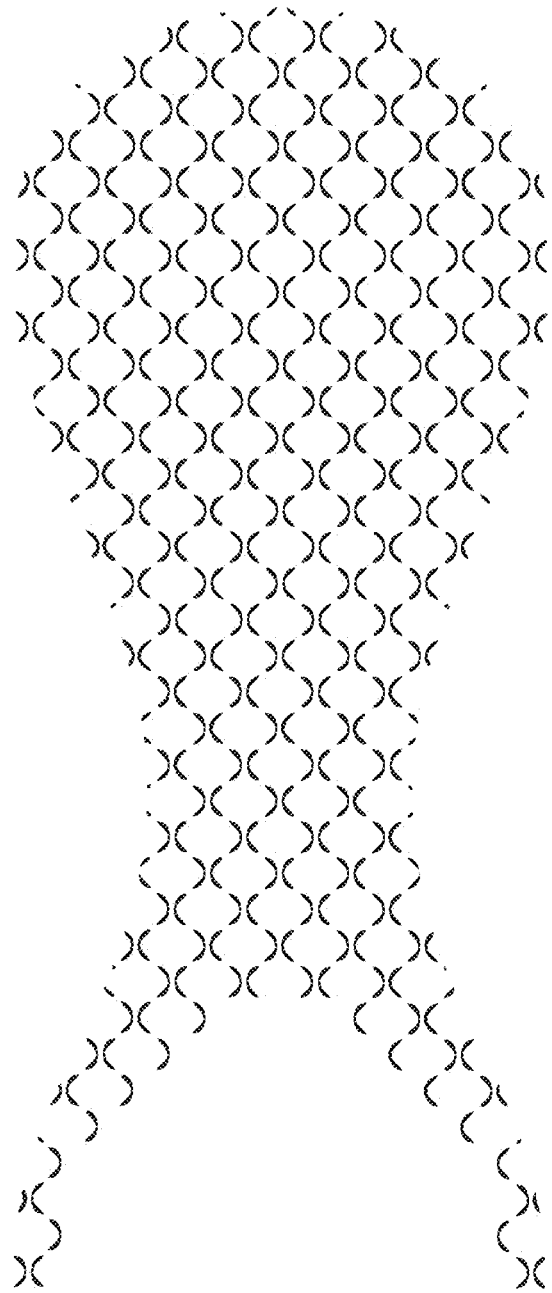
Figure 36:
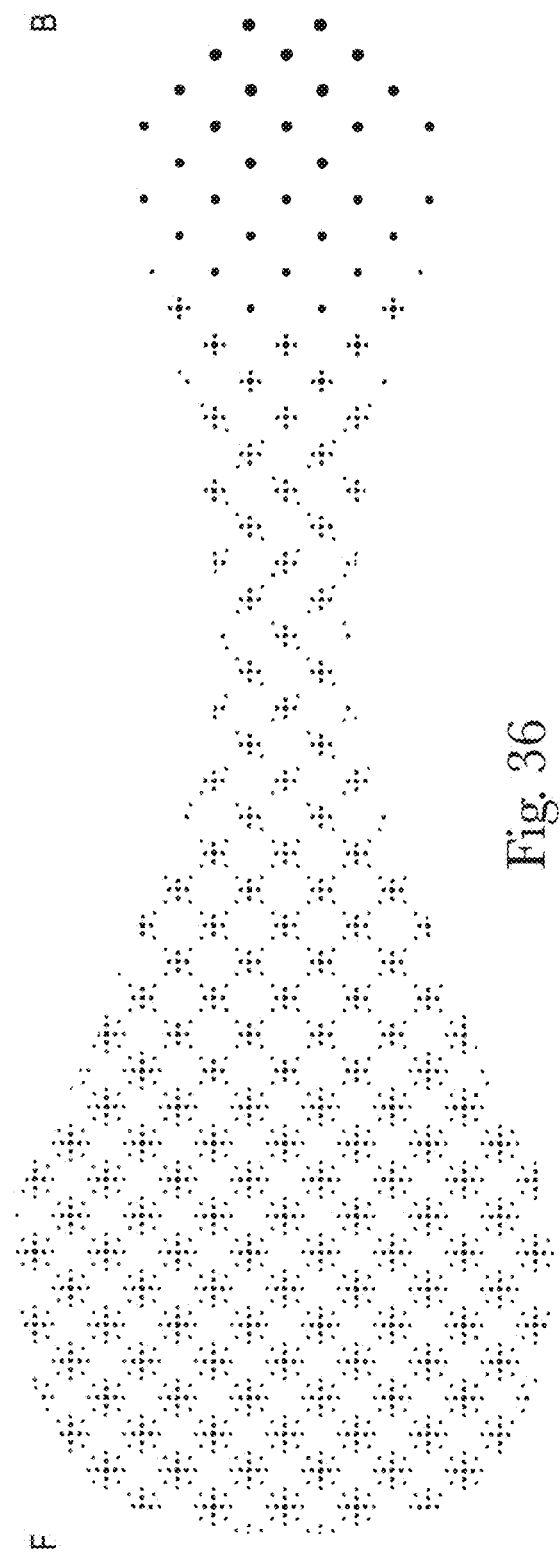
Figure 37:
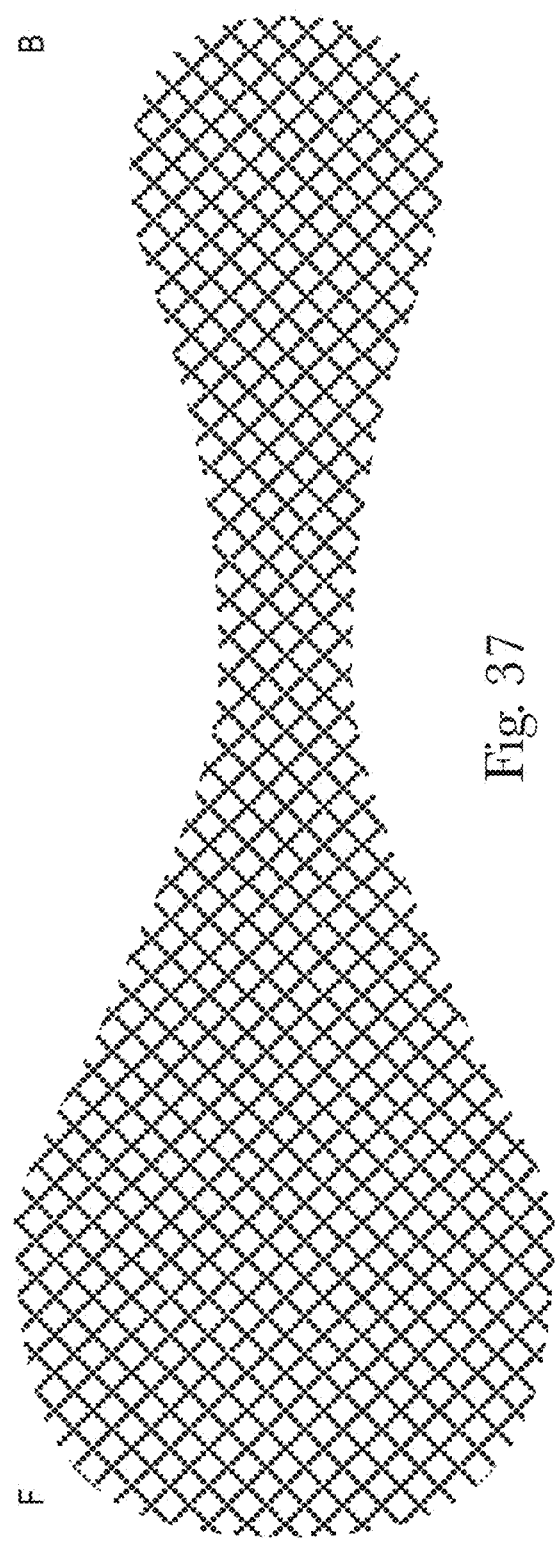
Figure 38:
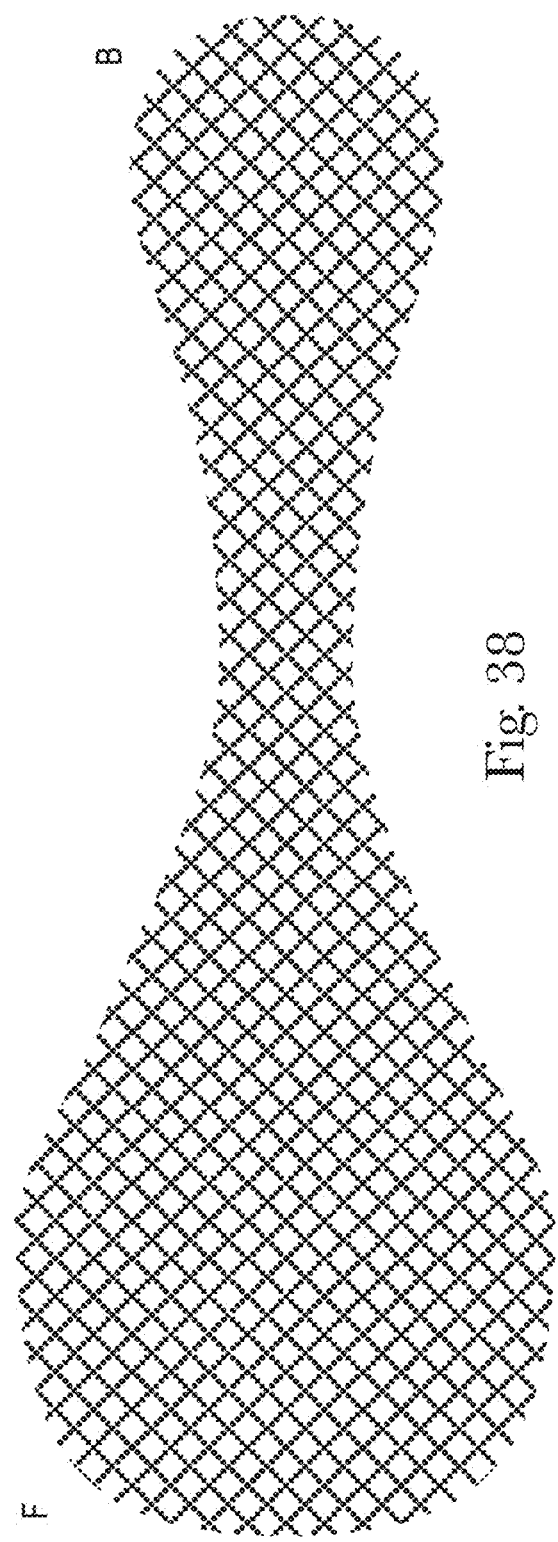
Figure 39:
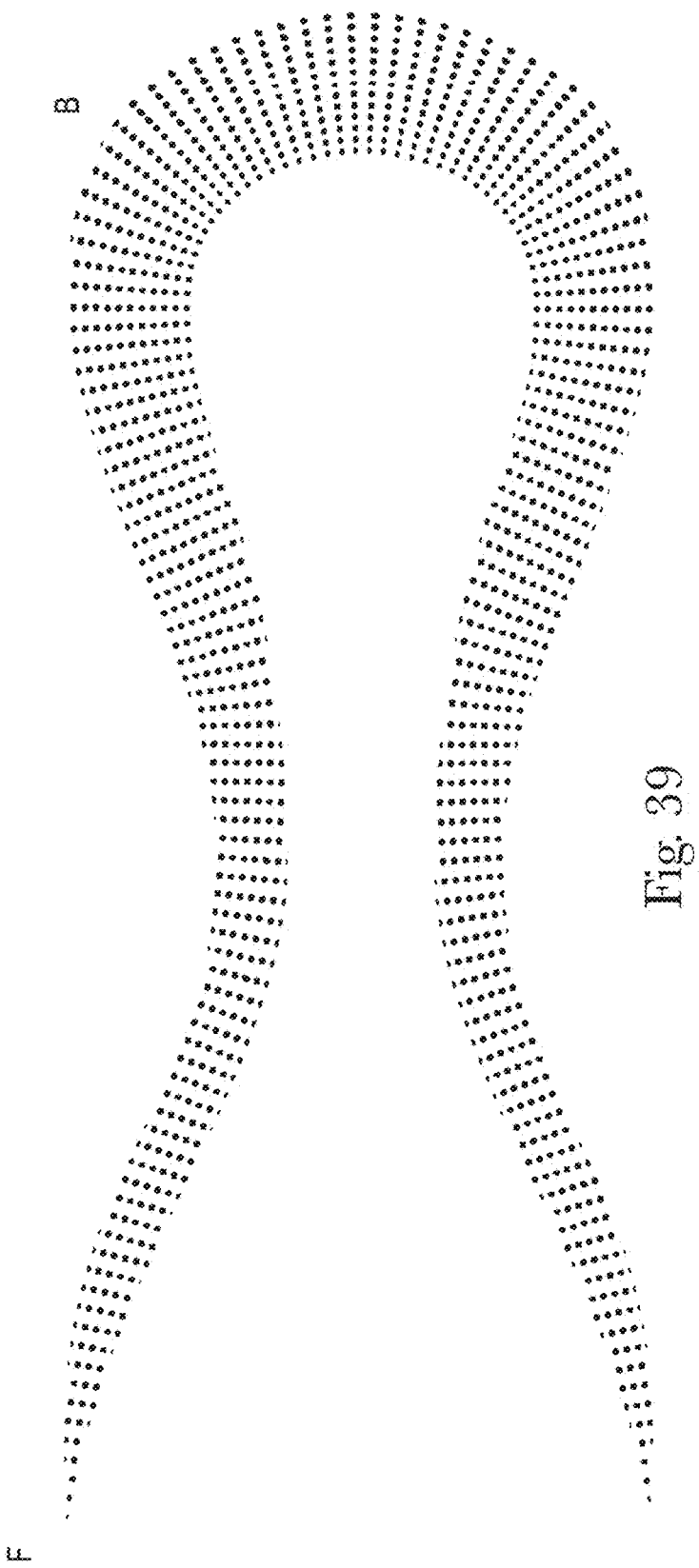

FIG. 32 is a photograph of an actual absorbent article comprising a topsheet similar to the example topsheet of FIG. 31.

Figure 40:
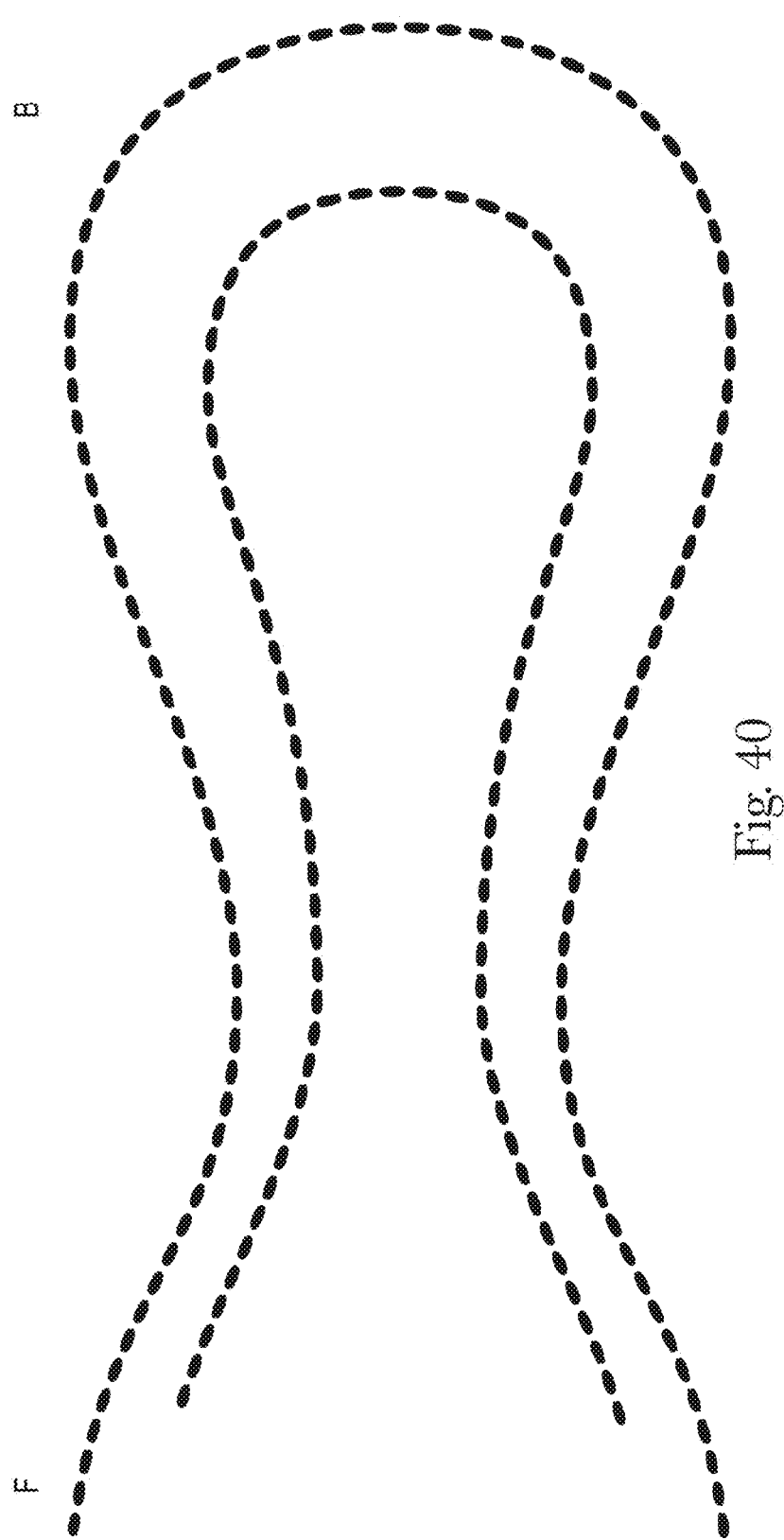
Figure 41:
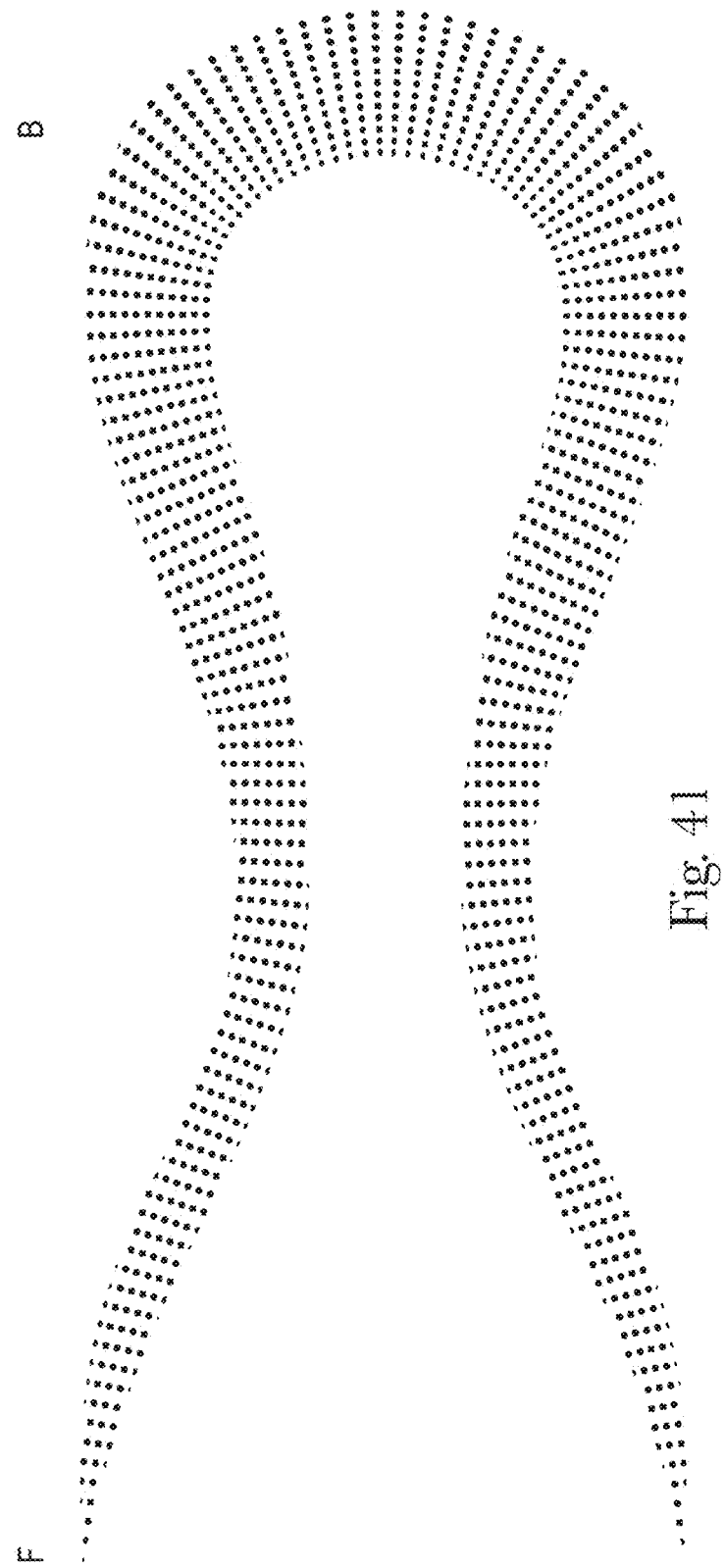
Figure 42:
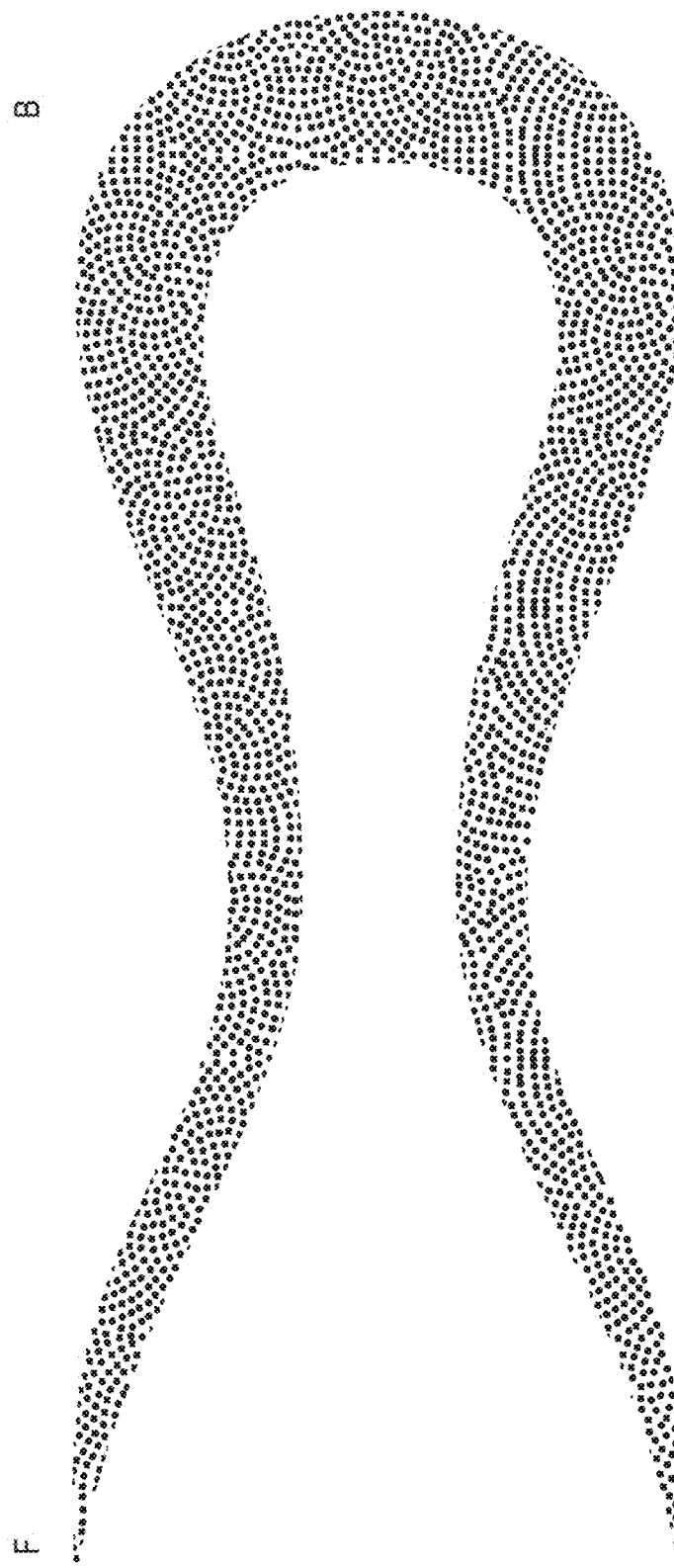

FIGS. 33-42 are examples of designs for topsheets, or portions thereof, for absorbent articles. The designs may comprise geometric, morphological, and/or chemical treatments in one or more patterns. The designs may also comprise flow control materials that may or may not for an at least mostly enclosed perimeter. The patterns may vary throughout the length, or a portion of the length, of the topsheet. The front portion of the topsheet is labeled F and the back portion of the topsheet is labeled B. The topsheets may be rectangular or any other suitable shape and have the designs thereon or therein. The treatments may be embossments, printed graphics, flow control materials, and/or apertures, or combinations thereof, for example. FIGS. 40-42 illustrate designs that comprise one or more flow control materials that form an at least mostly enclosed perimeter and are discontinuous. FIG. 40 illustrates two flow control materials that each form an at least mostly enclosed perimeter and that are both discontinuous, although one or both of them could be continuous.

As is illustrated in the various substrates (e.g., topsheets) with zones illustrated in FIGS. 15-42, the zones may take on a variety of configurations, sizes, and shapes, and the zones, or portions thereof, may comprise chemical, geometric, and/or morphological treatments or, a particular zone may not comprise treatments at all. The zones or portions thereof may comprise flow control materials. The various treatments will be discussed below in greater detail below. Apertures may be created via punching, slitting, hydroforming, or overbonding followed by ringrolling. 3D structures may be formed with various solid state formation technologies, such as SELFing, IPS, or rIPS.

Geometric Treatments

Some example geometric treatments are now discussed with reference to the figures. Because the phrase "geometric treatments" includes morphological treatments and apertures, only apertures will be discussed here, although it will be understood that the morphological treatments discussed below are also within the scope of the phrase "geometric treatments" as per the definition of geometric treatment.

Figure 43:
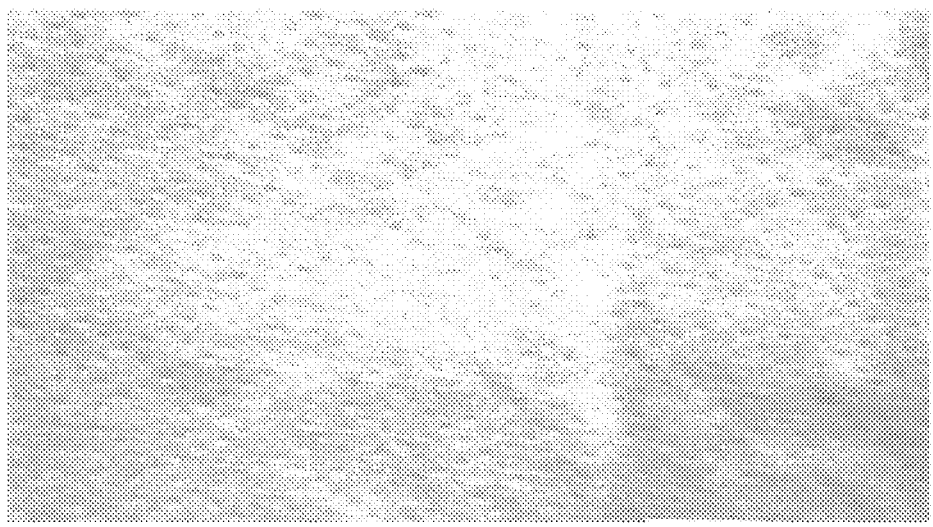
FIG. 43 is an example of a geometric treatment comprising apertures in accordance with the present disclosure.
Figure 44A:
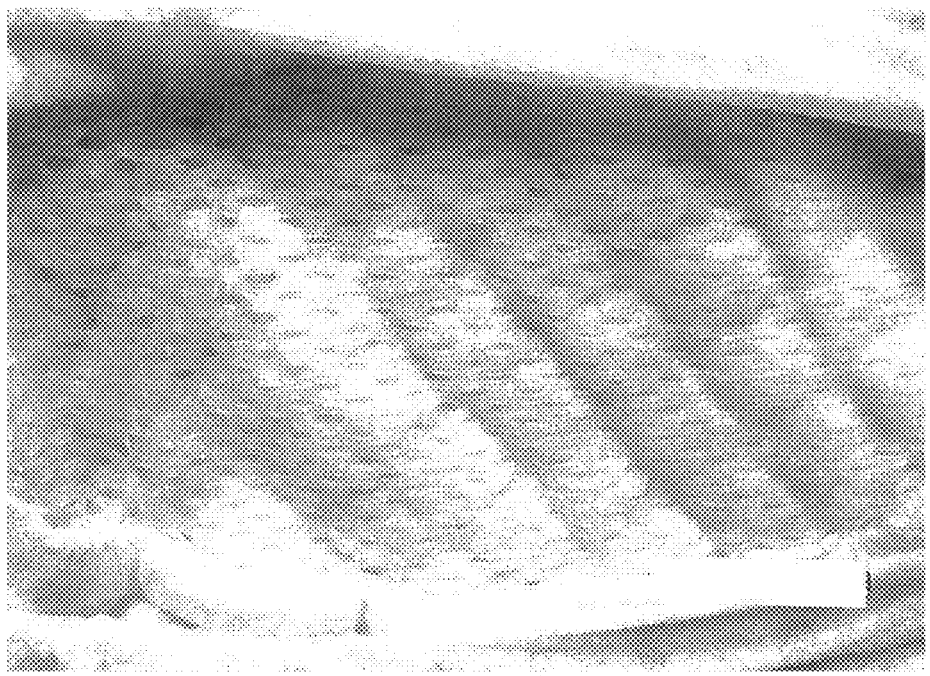
FIG. 44A is an example geometric treatment comprising apertures and embossing in accordance with the present disclosure.
Figure 44B:
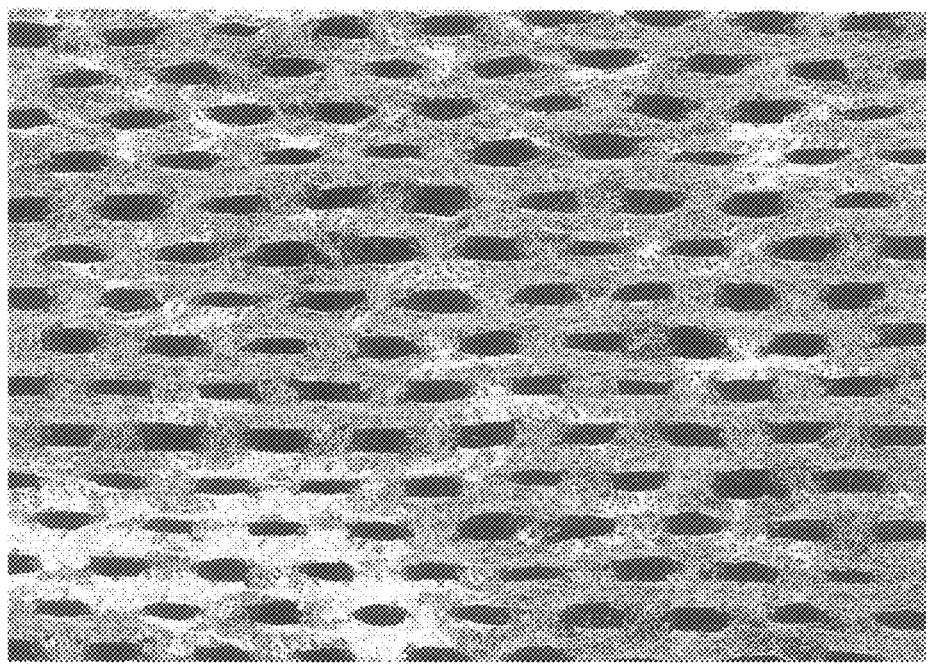
FIG. 44B illustrates an example substrate for use a portion of, or all of, a topsheet in accordance with the present disclosure.
Figure 44C:
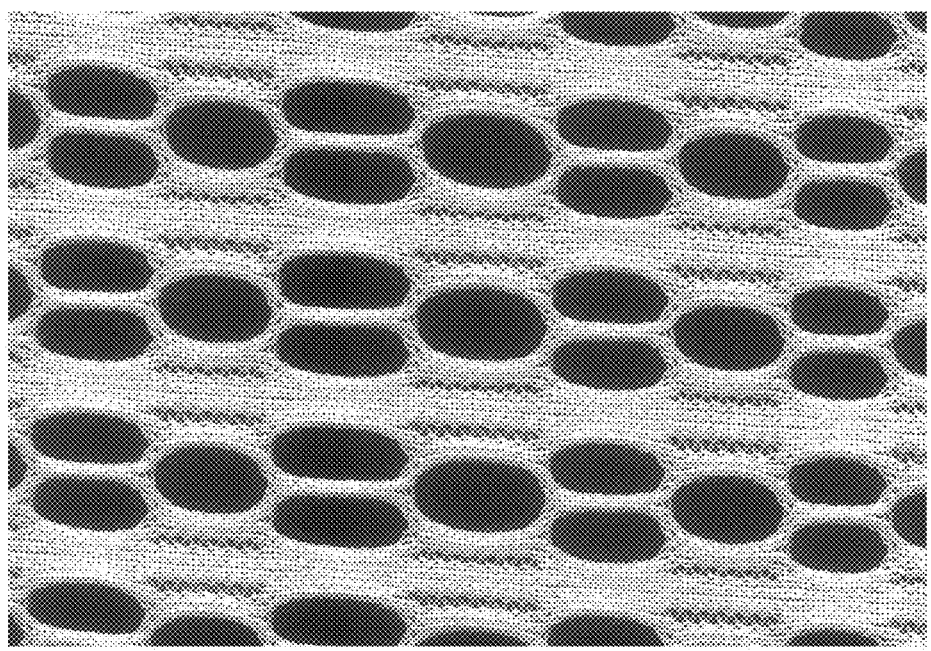
FIG. 44C illustrates an example fabric substrate for use a portion of, or all of, a topsheet in accordance with the present disclosure.
Figure 44D:
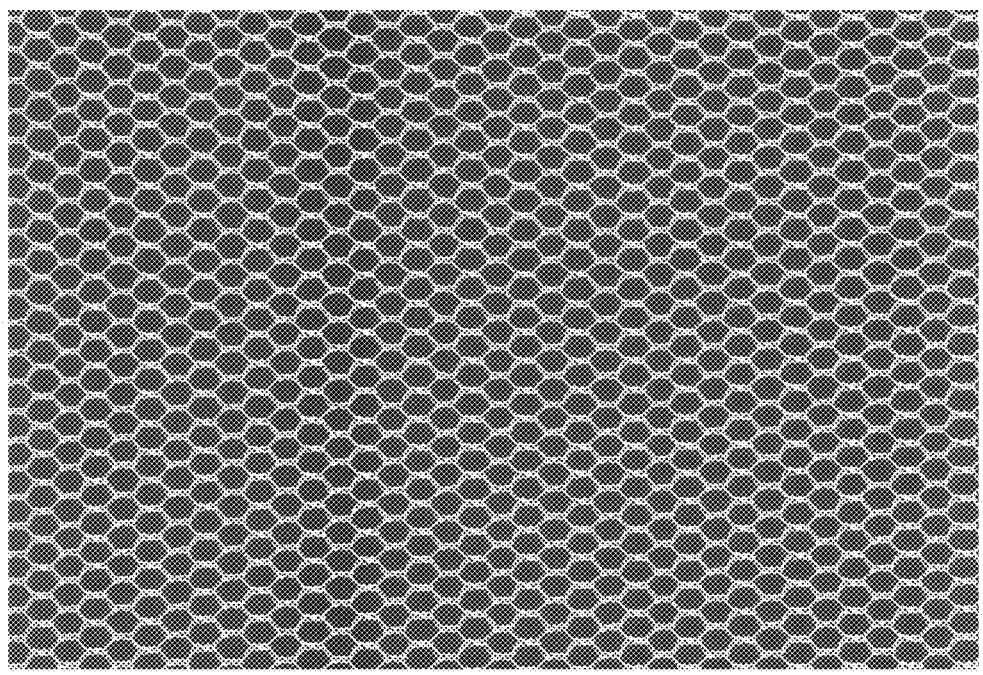
FIG. 44D illustrates an example mesh for use a portion of, or all of, a topsheet in accordance with the present disclosure.
Figure 44E:
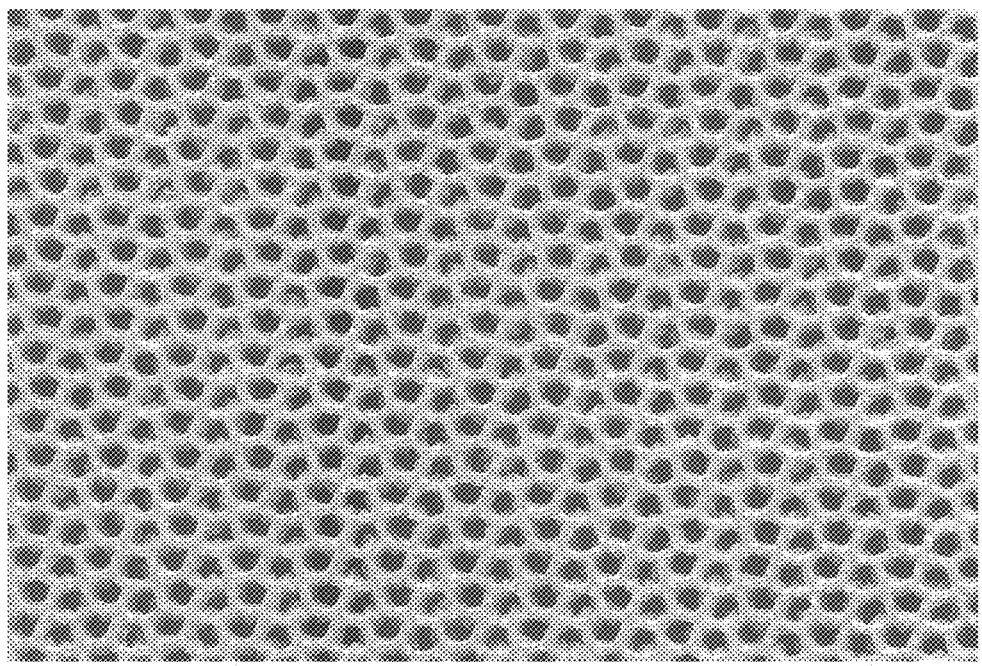
FIG. 44E illustrates an example film for use a portion of, or all of, a topsheet in accordance with the present disclosure.
Figure 44F:
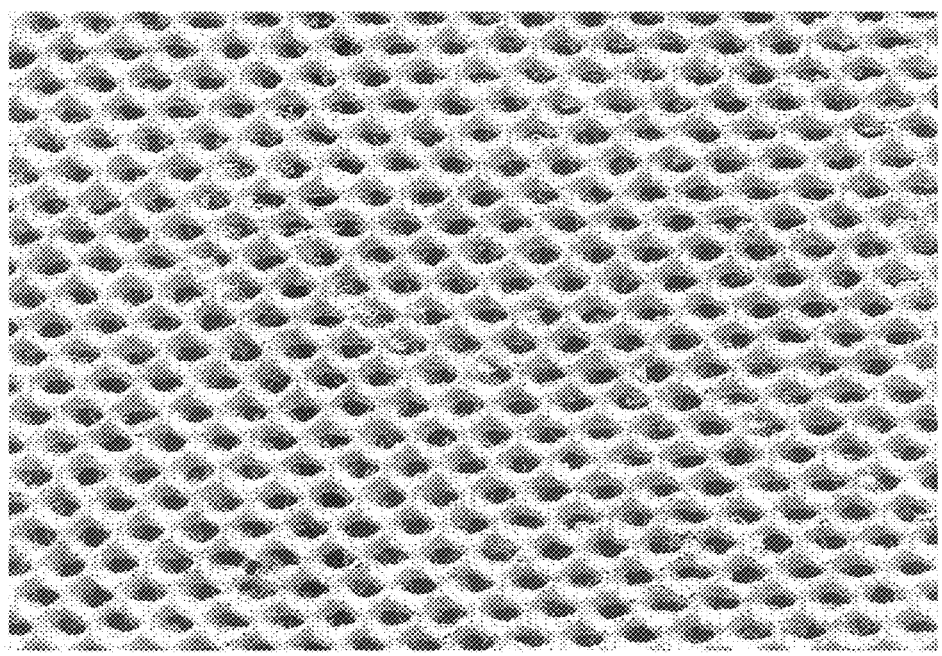
FIG. 44F illustrates an example film for use a portion of, or all of, a topsheet in accordance with the present disclosure.

FIGS. 43 through 44F illustrate example substrates (e.g., topsheets or portions thereof) that comprise geometric treatments comprising apertures. FIGS. 43 illustrates a 27 gsm nonwoven web having apertures defined therein, while FIG. 44A illustrates an 18 gsm bicomponent nonwoven web having apertures defined therein. The apertures of a geometric treatment may have any suitable size, shape, configuration, and/or pattern. The apertures may be formed by any aperturing process generally known in the art, such as overbonding and ring rolling to rupture the overbonds, and pinholing, for example. The apertures may be uniformly spaced or non-uniformly spaced relative to each other. Furthermore, the apertures in each zone may be the same size or different sizes in the same zone or in different zones. FIGS. 17-19, 21, 21A, and 27-30, among other figures, show various non-limiting examples of geometric treatments comprising apertures in a topsheet or other substrate. FIG. 44B illustrates an example substrate for use as a portion of, or all of, a topsheet. FIG. 44C illustrates an example fabric substrate for use as a portion of, or all of, a topsheet. FIG. 44D illustrates an example mesh substrate for use as a portion of, or all of, a topsheet. FIG. 44E illustrates an example film for use as a portion of, or all of, a topsheet. FIG. 44F illustrates an example film for use as a portion of, or all of, a topsheet.

The example substrate of FIG. 44B may have an effective aperture area (according to the Aperture Test below) in the range of about 0.5 $mm^2$ to about 10 $mm^2$, about 1 $mm^2$ to about 8 $mm^2$, about 1 $mm^2$ to about 6 $mm^2$, about 1 $mm^2$ to about 5 $mm^2$, about 1 $mm^2$ to about 3 $mm^2$, about 1.5 $mm^2$ to about 2.5 $mm^2$, about 1.9 $mm^2$, about 2.0 $mm^2$, about 2.1 $mm^2$, or about 2.011 $mm^2$, specifically reciting all 0.1 $mm^2$ increments within the specified ranges and all ranges formed therein or thereby. The example substrate of FIG. 44B may have a % effective open area (according to the Aperture Test below) in the range of about 5% to about 40%, about 10% to about 30%, about 15% to about 25%, about 16% to about 20%, about 17%, about 18%, or about 19%, specifically reciting all 0.1% increments within the specified ranges and all ranges formed therein or thereby.

The example fabric substrate of FIG. 44C may have an effective aperture area (according to the Aperture Test below) in the range of about 3 $mm^2$ to about 30 $mm^2$, about 6 $mm^2$ to about 20 $mm^2$, about 8 $mm^2$ to about 14 $mm^2$, about 9 $mm^2$ to about 13 $mm^2$, about 10 $mm^2$ to about 12 $mm^2$, about 11 $mm^2$, about 12 $mm^2$, about 11.1 $mm^2$, about 11.2 $mm^2$, or about 11.11 $mm^2$, specifically reciting all 0.1 $mm^2$ increments within the specified ranges and all ranges formed therein or thereby. The example substrate of FIG. 44C may have a % effective open area (according to the Aperture Test below) in the range of about 15% to about 55%, about 20% to about 45%, about 25% to about 45%, about 30% to about 40%, about 35%, about 34%, or about 34.7%, specifically reciting all 0.1% increments within the specified ranges and all ranges formed therein or thereby.

The example mesh substrate of FIG. 44D may have an effective aperture area (according to the Aperture Test below) in the range of about 0.2 $mm^2$ to about 4 $mm^2$, about 0.5 $mm^2$ to about 3 $mm^2$, about 0.5 $mm^2$ to about 2 $mm^2$, about 0.5 $mm^2$ to about 1.5 $mm^2$, about 0.8 $mm^2$ to about 1.3 $mm^2$, about 0.9 $mm^2$, about 1 $mm^2$, about 1.1 $mm^2$, about 1.2 $mm^2$, or about 1.018 $mm^2$, specifically reciting all 0.1 $mm^2$ increments within the specified ranges and all ranges formed therein or thereby. The example substrate of FIG. 44D may have a % effective open area (according to the Aperture Test below) in the range of about 20% to about 90%, about 30% to about 80%, about 50% to about 80%, about 50% to about 70%, about 55% to about 70%, about 60%, about 63.9%, or about 65%, specifically reciting all 0.1% increments within the specified ranges and all ranges formed therein or thereby.

The example film of FIG. 44E may have an effective aperture area (according to the Aperture Test below) in the range of about 0.1 mm$^2$ to about 2 mm$^2$, about 0.1 mm$^2$ to about 1.5 mm$^2$, about 0.3 mm$^2$ to about 1 mm$^2$, about 0.4 mm$^2$ to about 0.9 mm$^2$, about 0.4 mm$^2$ to about 0.75 mm$^2$, about 0.5 mm$^2$, about 0.508 mm$^2$, about 0.51 mm$^2$, or about 0.52 mm$^2$, specifically reciting all 0.1 mm$^2$ increments within the specified ranges and all ranges formed therein or thereby. The example film of FIG. 44E may have a % effective open area (according to the Aperture Test below) in the range of about 5% to about 50%, about 10% to about 35%, about 10% to about 30%, about 12% to about 25%, about 15%, about 18%, about 18.2%, or about 19%, specifically reciting all 0.1% increments within the specified ranges and all ranges formed therein or thereby.

The example film of FIG. 44F may have an effective aperture area (according to the Aperture Test below) in the range of about 0.1 mm$^2$ to about 2 mm$^2$, about 0.1 mm$^2$ to about 1.5 mm$^2$, about 0.3 mm$^2$ to about 1 mm$^2$, about 0.4 mm$^2$ to about 0.9 mm$^2$, about 0.4 mm$^2$ to about 0.75 mm$^2$, about 0.4 mm$^2$, about 0.486 mm$^2$, or about 0.5 mm$^2$, specifically reciting all 0.1 mm$^2$ increments within the specified ranges and all ranges formed therein or thereby. The example film of FIG. 44F may have a % effective open area (according to the Aperture Test below) in the range of about 3% to about 35%, about 3% to about 20%, about 3% to about 15%, about 5% to about 13%, about 6%, about 11%, about 8%, about 8.7%, or about 9%, specifically reciting all 0.1% increments within the specified ranges and all ranges formed therein or thereby.

A topsheet of an absorbent article may have two or more zones with at least a first zone being positioned on a first side of a lateral axis or a first side of a substantially laterally-extending separation element and with a second zone being positioned on a second side of the lateral axis or a second side of a substantially laterally-extending separation element. The first zone may have apertures defined therein which may have an effective aperture area in the range of about 0.2 mm$^2$ to about 15 mm$^2$, specifically reciting all 0.1 mm$^2$ increments within the specified range, according to the Aperture Test described below. The first zone may have an effective open area of about 15% to about 40%, specifically reciting all 0.1% increments within the specified range, according to the Aperture Test described below. The second zone may have apertures defined therein which may have an effective aperture area in the range of about 0.1 mm$^2$ to about 2.0 mm$^2$, about 0.05 mm$^2$ to about 2 mm$^2$, about 0.5 mm$^2$ to about 2 mm$^2$, or about 1.0 mm$^2$, according to the Aperture Test described below. The second zone may have a % effective open area of about 2% to about 15%, specifically reciting all 0.1% increments within the specified range, according to the Aperture Test described below. The apertures in the first zone may be larger than the apertures in the second zone (e.g., 15-35% larger or 25% larger) such that the first zone is configured for BM management and such that the second zone is configured for urine management. Either of the first and second zones may comprise one or more chemical treatments and/or one or more morphological treatments. The morphological treatment may be present in a portion of, or all of, the first zone and/or the second zone. The absorbent article may also comprise barrier leg cuffs and a waist edge.

Any of the apertures of the geometric treatments may overlap or not overlap portions of, and/or all of, the channels (e.g., 49, 49') in the liquid management system 50 or the channels (e.g., 26, 26', 27, 27') in the absorbent core 28, if either set of channels is provided.

Morphological Treatments

Figure 45:
FIG. 45 is an example morphological treatment comprising embossing in accordance with the present disclosure.
Figure 46A:
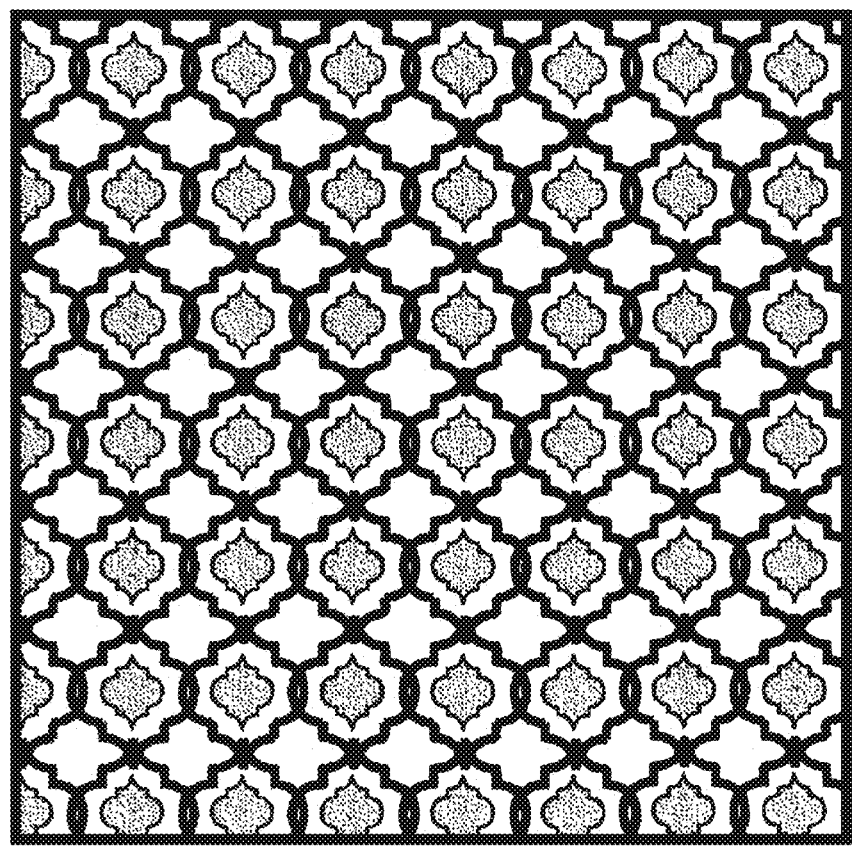
FIG. 46A is an illustration of an example morphological treatment comprising embossing in accordance with the present disclosure.
Figure 46B:
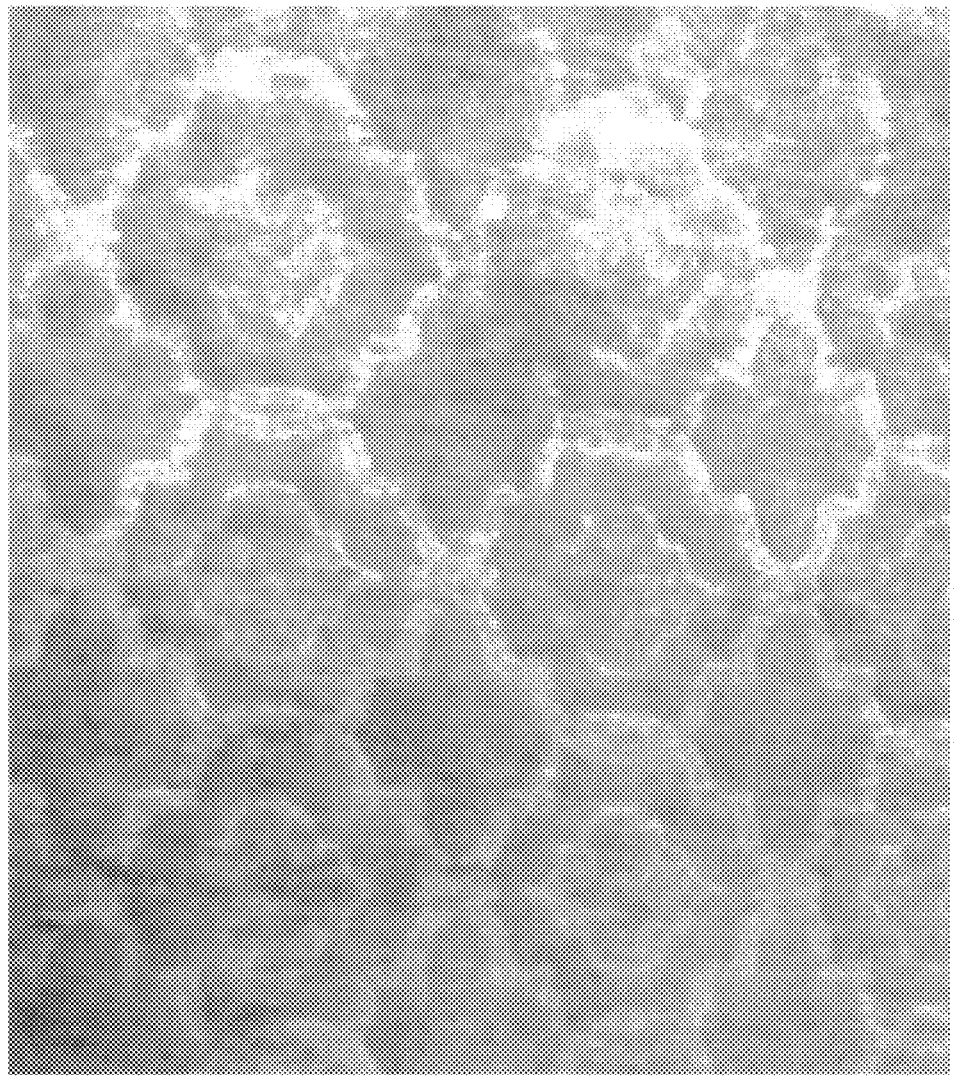
FIG. 46B is a photograph of a topsheet having the morphological treatment of FIG. 46A in accordance with the present disclosure.
Figure 47:
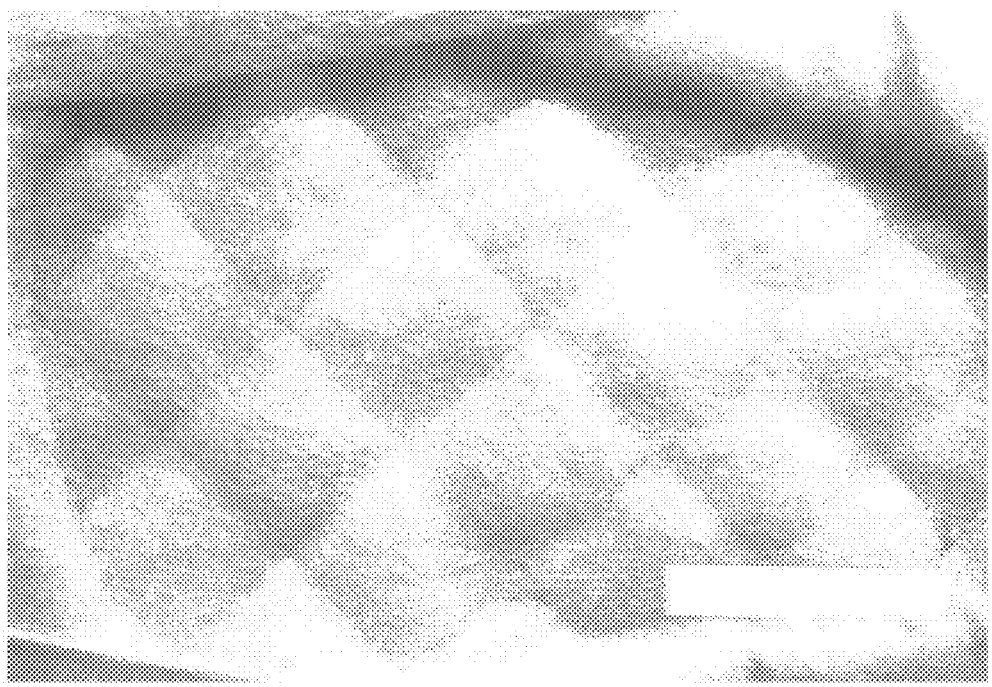
FIGS. 47-49 are examples morphological treatments comprising embossing in accordance with the present disclosure.
Figure 48:
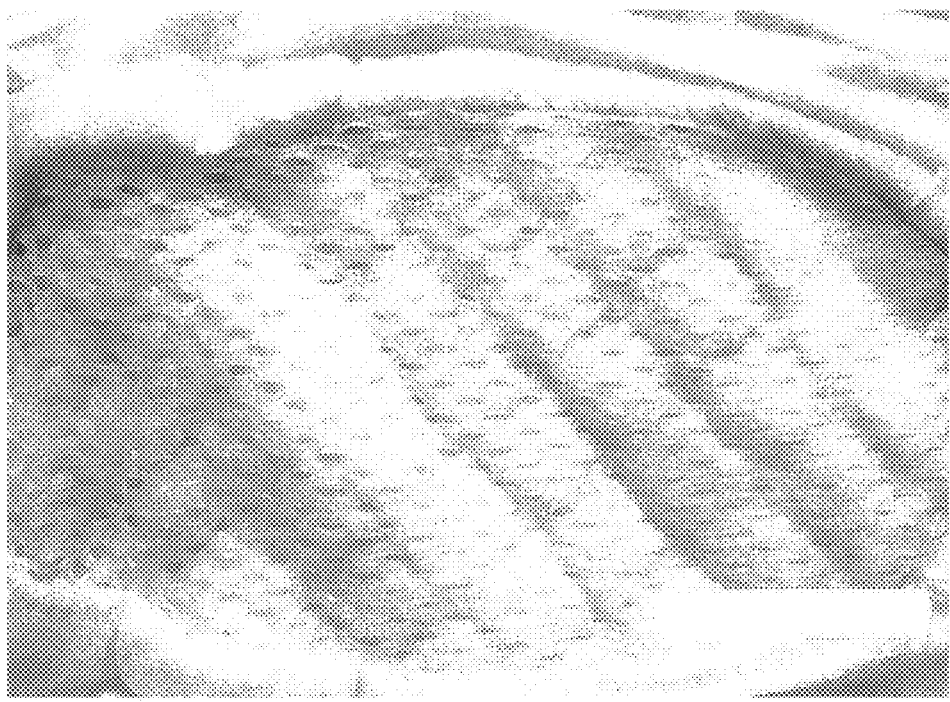
Figure 49:
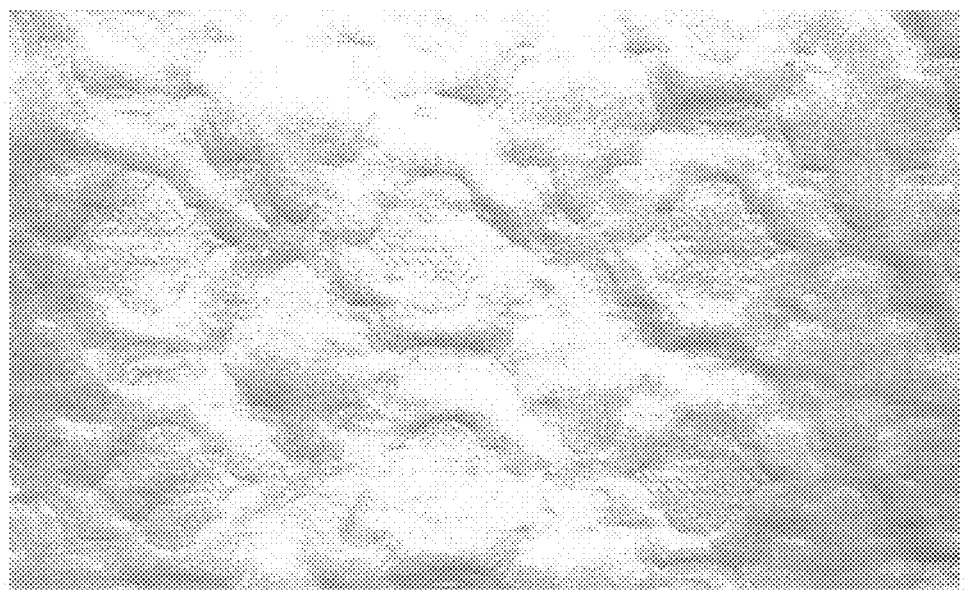
Figure 50:
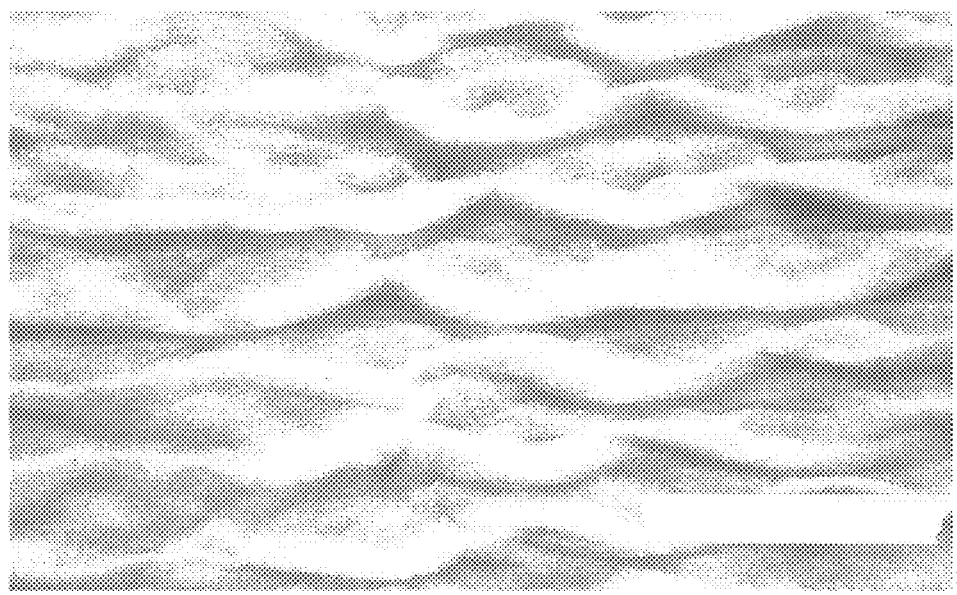
FIG. 50 is an example of a morphological treatment comprising puckering in accordance with the present disclosure.
Figure 51:
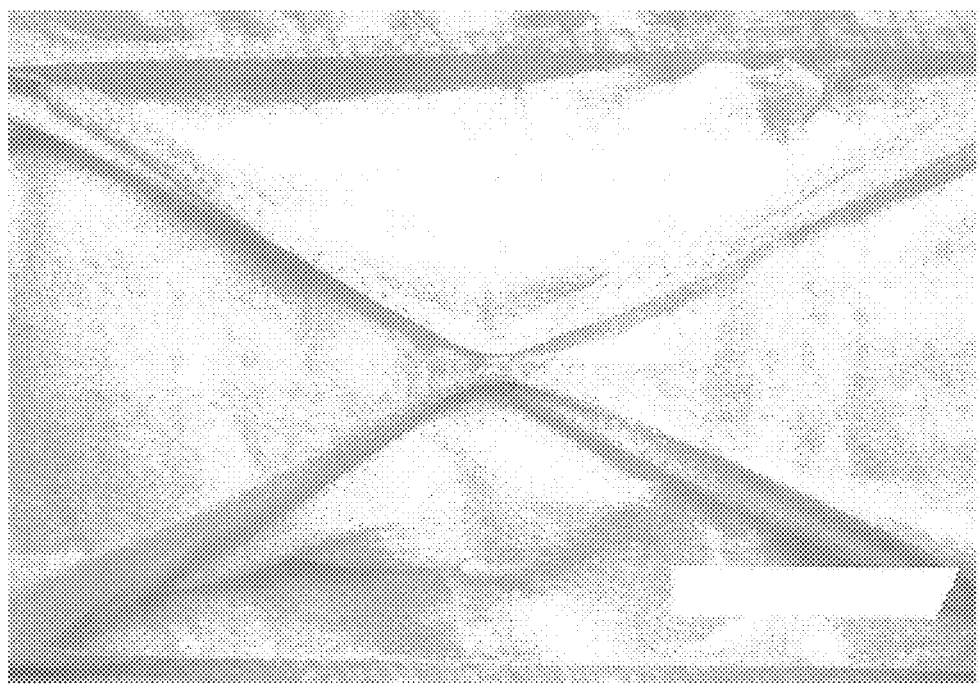
FIG. 51 is an example of a morphological treatment comprising folding in accordance with the present disclosure.

Various morphological treatments may be present in various zones of the topsheet 24, the LMS 50, or other substrate. FIGS. 45-50 illustrate various morphological treatments. FIG. 45 illustrates an embossed pattern. FIG. 46A is a graphical illustration of the pattern of embossments shown in FIG. 46B. FIG. 47 illustrates another embossed pattern. FIG. 48 illustrated another embossed pattern with the substrate being apertured. FIG. 49 illustrates another embossed pattern. FIG. 50 illustrates an example morphological treatment that comprises puckered areas. The puckered areas may be formed in a two layer topsheet. Adhesive, or patterned adhesive, may be present intermediate the first and second layers. The first layer may be embossed to achieve the shape of the puckered areas and then attached to the second layer using the patterned adhesive. FIG. 51 illustrates an example morphological treatment that comprises fold lines. The fold lines may be formed by substrates attached to the topsheet. Other morphological treatments are illustrated in at least some of FIGS. 20-32 in a topsheet. The elements of a morphological treatment may have any suitable sizes, shapes, dimensions, frequencies, configurations, and/or patterns. The morphological treatments may be formed by any processes known to those of skill in the art. The elements of each morphological treatment may be uniformly spaced or non-uniformly spaced relative to each other. Furthermore, the elements of a morphological treatment in each zone may be the same or different. The elements of a morphological treatment in a zone, or in more than one zone, may differ in pattern, depth, width, length, and/or frequency, or may be the same. One zone having a morphological treatment may be symmetrical to, or asymmetrical to, another zone having a morphological treatment with respect to a lateral axis, a longitudinal axis, or a substantially laterally-extending separation element of an absorbent article. Any of the zones having a morphological treatment may overlap or not overlap portions of, or all of, the channels (e.g., 49, 49') in the liquid management system 50 and/or the channels (e.g., 26, 26', 27, 27') in the absorbent core 28, if present.

Figure 52:
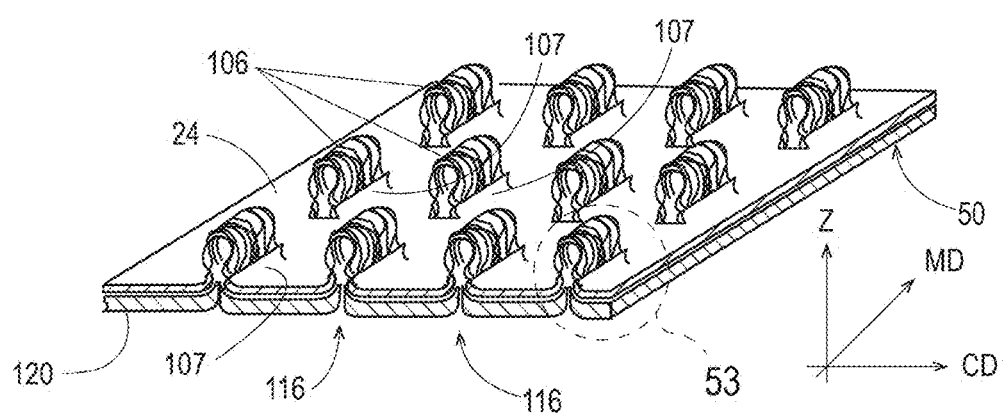
FIG. 52 is a perspective view of an example morphological treatment where portions of a liquid management system extend into or through a liquid permeable topsheet in accordance with the present disclosure.
Figure 53:
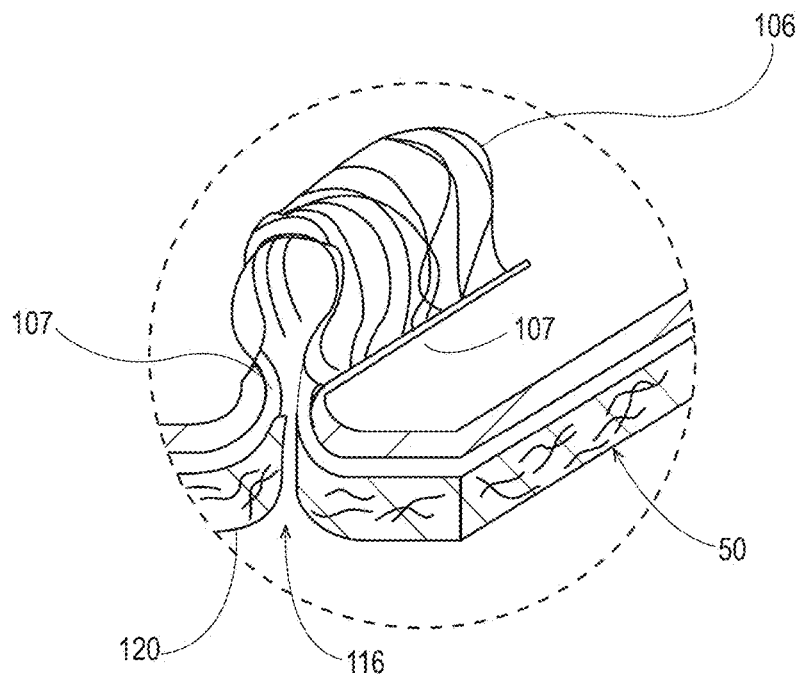
FIG. 53 is an exploded perspective view taken from circle 43 of FIG. 52 in accordance with the present disclosure.

An example morphological treatment is illustrated in FIGS. 52 and 53. FIG. 53 is an exploded view from circle 53 of FIG. 52. In this example morphological treatment, portions 106 of the liquid management system 50 (one or more layers, or all layers, of the LMS 50) extend into or through the liquid permeable topsheet 24. Discontinuities 116 may be formed in a garment-facing surface 120 of the liquid management system 50. Flaps 107 may be formed in the liquid permeable topsheet 24 at locations where the portions 106 extend into and/or through the liquid permeable topsheet 24. Such a structure may aid in liquid absorption in that the liquid management system 50 may quickly wick liquid through the topsheet 24 owing to the projections 106. This structure may also help reduce the amount of time liquid, such as urine, remains on the topsheet 24.

Figure 54:
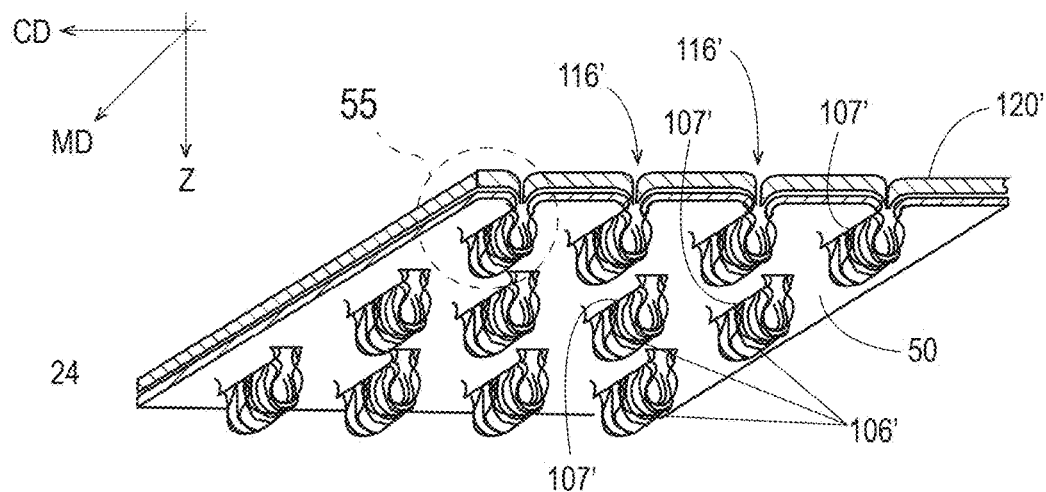
FIG. 54 is a perspective view of an example morphological treatment where portions of a liquid permeable topsheet extend into or through a liquid management system in accordance with the present disclosure.
Figure 55:
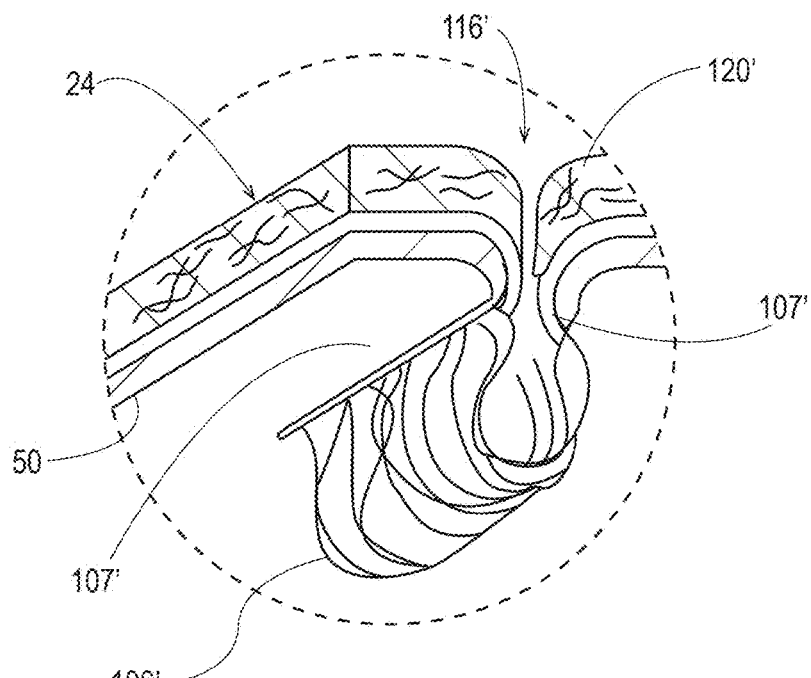
FIG. 55 is an exploded perspective view taken from circle 55 of FIG. 54 in accordance with the present disclosure.

Another example morphological treatment is illustrated in FIGS. 54 and 55. FIG. 55 is an exploded view from circle 55 of FIG. 54. In this example morphological treatment, portions 106' of the liquid permeable topsheet 24 extend into or though one or more layers, or all layers, of the liquid management system 50. Discontinuities 116' may be formed in a wearer-facing surface 120' of the liquid permeable topsheet 24. Flaps 107' may be formed in the liquid management system 50 at locations where the portions 106' extend into and/or through the liquid management system 50. Such a structure may aid in liquid adsorption in that an absorbent core positioned under the LMS 50 may quickly absorb liquid through the topsheet 24 and the LMS 50 owing to the projections 106'. Such a structure may also reduce the amount of time liquid, such as urine, is present on the topsheet 24. This morphological treatment is essentially the reverse of the morphological treatment illustrated in FIGS. 52 and 53.

Figure 56:
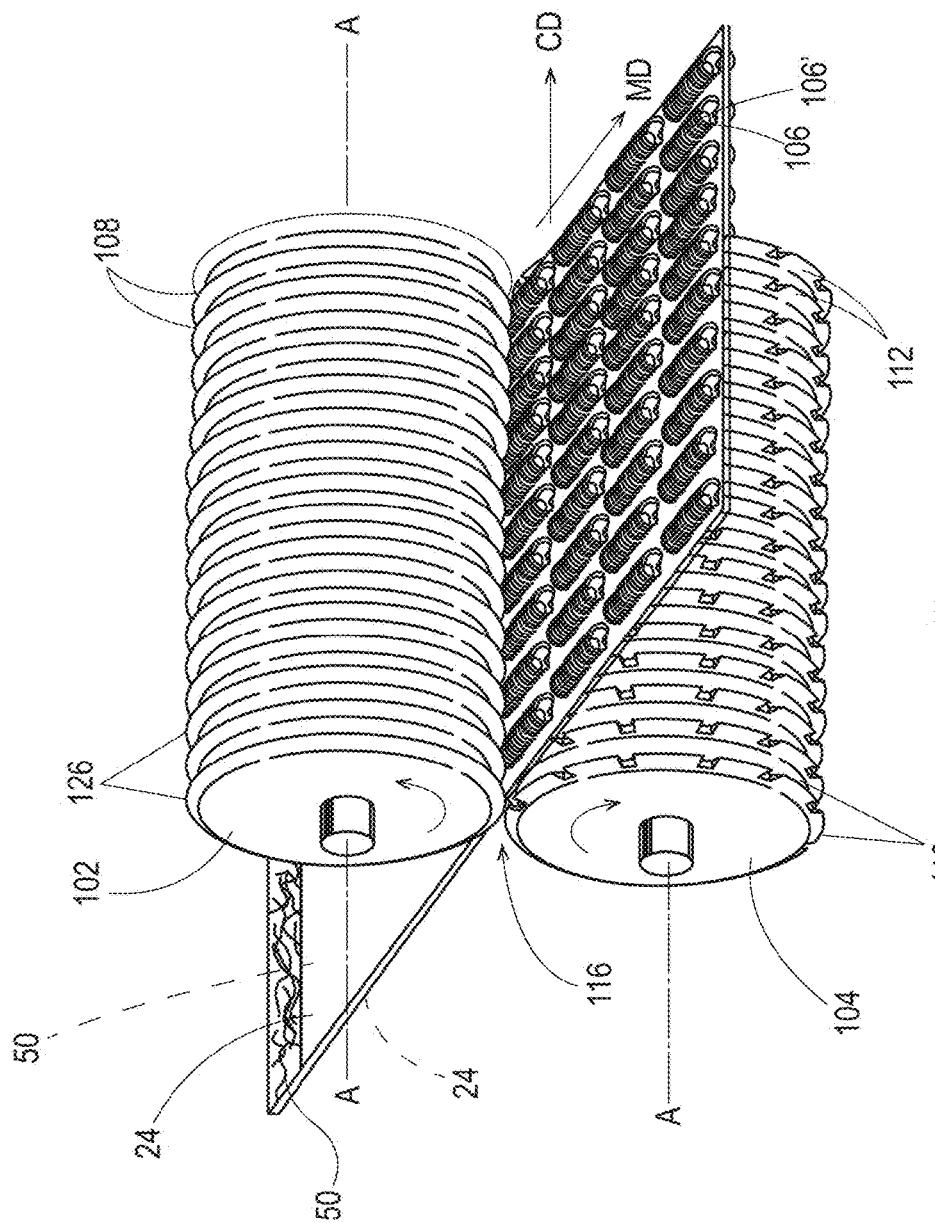
FIG. 56 is a perspective view a process used to make the morphological treatments of FIGS. 52 and 44 in accordance with the present disclosure.
Figure 57:
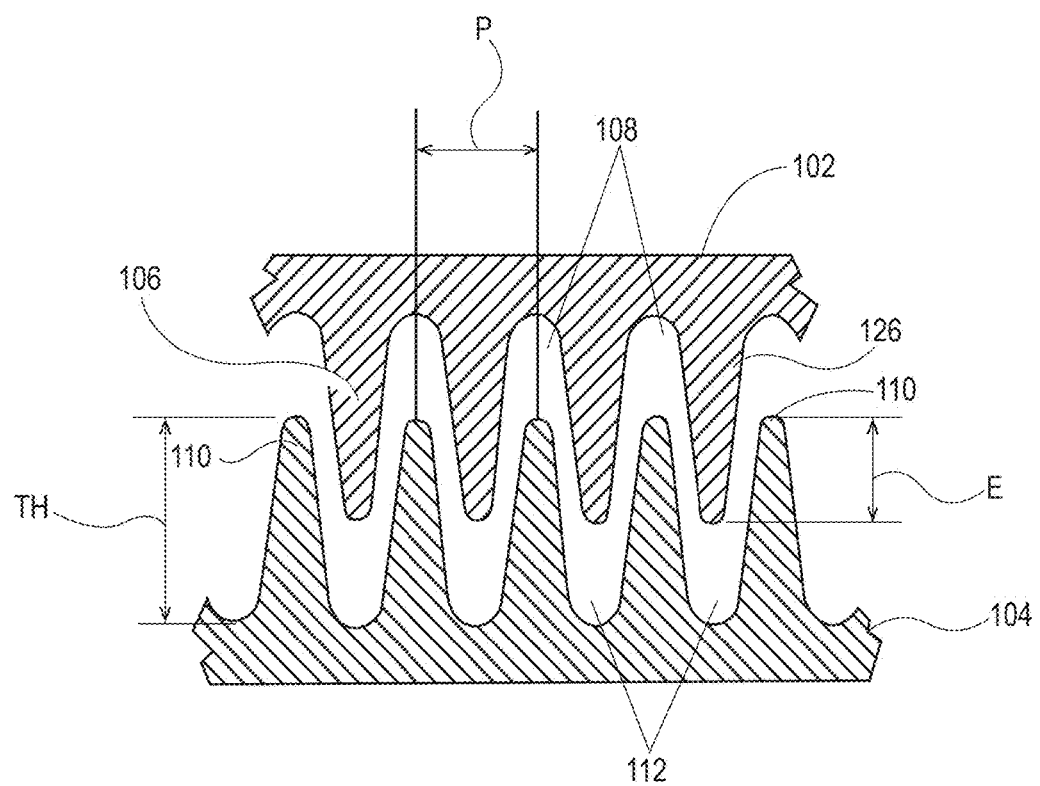
FIG. 57 is a front view of engagement of portions rolls from the process of FIG. 56 in accordance with the present disclosure.

Both of the two above-described morphological treatments may be formed in a similar fashion. The portions 106 or 106' may be formed using the process illustrated in FIG. 56. The process may comprise advancing a web comprising the liquid permeable topsheet 24 superimposed over at least a portion of the liquid management system 50 or advancing a web comprising the liquid management system 50 superimposed over at least a portion of the liquid permeable topsheet 24 (as indicated in dashed reference numbers 24 and 50) through a nip 116 formed by two rolls 102 and 104. The two rolls rotate above their respective longitudinal axes A in the direction shown by the arrows on the rolls. The roll 102 may comprise a groove roll comprising a plurality of outwardly extending ridges 126 forming a plurality of grooves 108 therebetween. The roll 104 may comprise a plurality of radially outwardly extending teeth 110 and a plurality of grooves 112 formed therebetween. The ridges 126 of the roll 102 may be configured to extend into the grooves 112 of the roll 104 and the teeth 110 of the roll 104 may be configured to extend into the grooves 108 of the roll 102 to form the portions 106 or 106'. As can be seen in FIG. 56, this arrangement forces portions of the liquid management system 50 through or into the liquid permeable topsheet 24 to form the portions 106 or forces portions of the liquid permeable topsheet 24 though or into the liquid management system 50 to form the portions 106'. The intermeshing of the rolls 102 and 104 is illustrated in more detail in FIG. 57, without the liquid permeable topsheet 24 and the liquid management system 50 being present. "P" is the pitch between the teeth 110, "E" is the depth of engagement of the ridges 126 into the grooves 112, and "TH" is the tooth height. All of these measurements may be varied to achieve differently shaped and/or sized portions 106 or 106', for example. Further details regarding such a structure, and the method of producing it, is disclosed in U.S. Pat. No. 7,648,752 to Hoying et al.

The teeth 110 on the roll 104 may vary about the circumference of the roll 104, in the direction of rotation of the roll 104, such that the formed projections 106 may differ in pattern, depth, length, width, and/or frequency of the extension of the liquid management system 50 into or through the liquid permeable topsheet 24 or the liquid permeable topsheet 24 into or through the liquid management system 50. The teeth on about 50% of the roll 104, in the direction of rotation of the roll 104, may have a first configuration, size, length, width, pattern, frequency etc. while the teeth on the remainder of the roll may have a second configuration, size, length, width, pattern, frequency etc. In other instances, teeth having certain configurations may be formed in more than two zones on the roll 104. The varying of the teeth may allow the rolls to create zones having different portions 106 or 106' and thereby different morphological treatments, in, for example, a first zone of the topsheet 24 and a second zone of the topsheet 24.

Chemical Treatments

Figure 58:
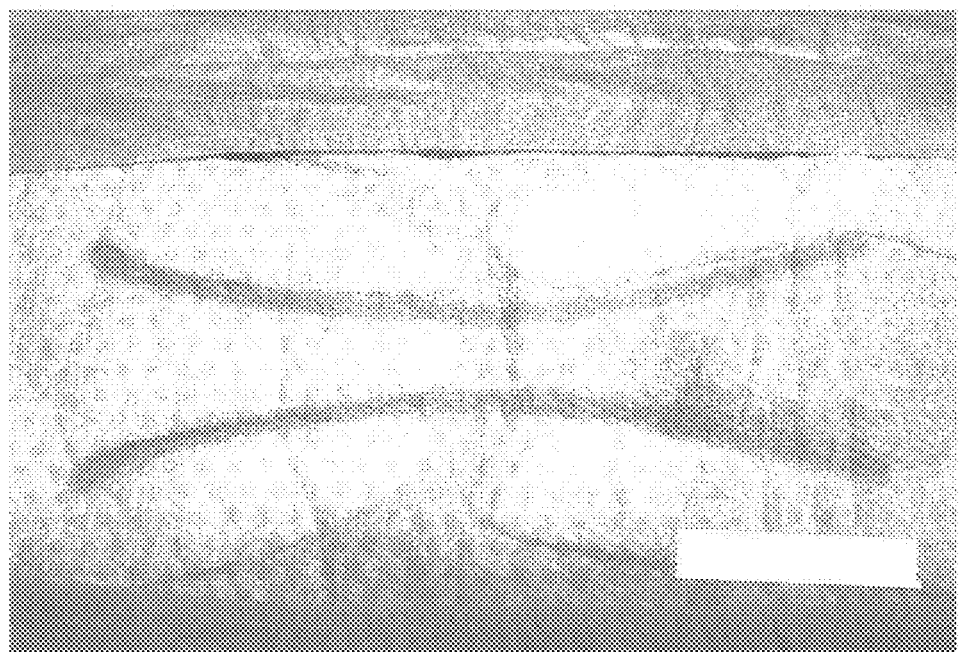
FIG. 58 is a photograph of a morphological or chemical treatment in a topsheet in accordance with the present disclosure.
Figure 59:
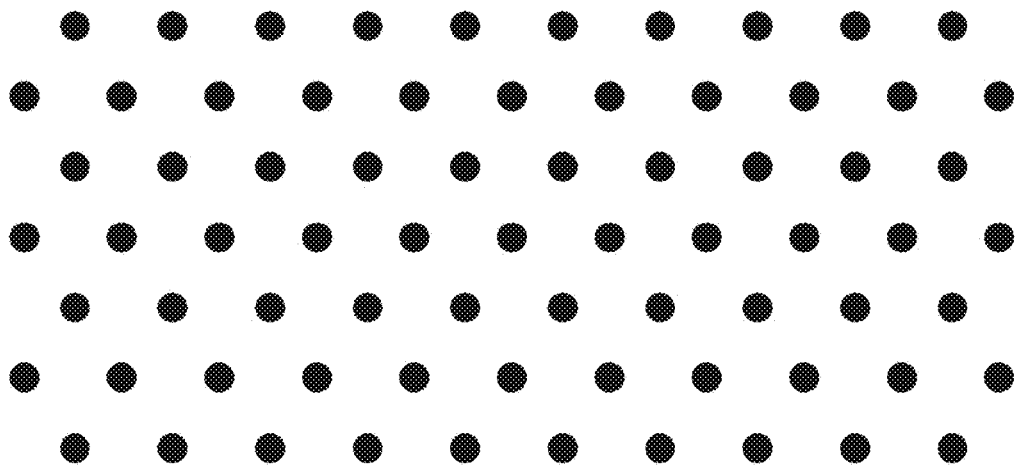
FIG. 59 is an illustration of a chemical treatment pattern in accordance with the present disclosure.
Figure 60:
FIG. 60 is a photograph of the chemical treatment pattern of FIG. 59 on a topsheet in accordance with the present disclosure.
Figure 61:
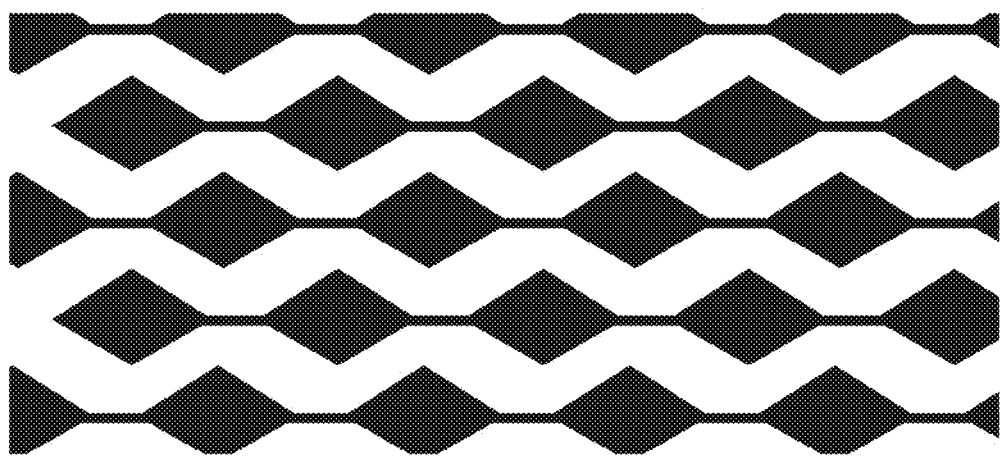
FIG. 61 is an illustration of a chemical treatment pattern in accordance with the present disclosure.
Figure 62:
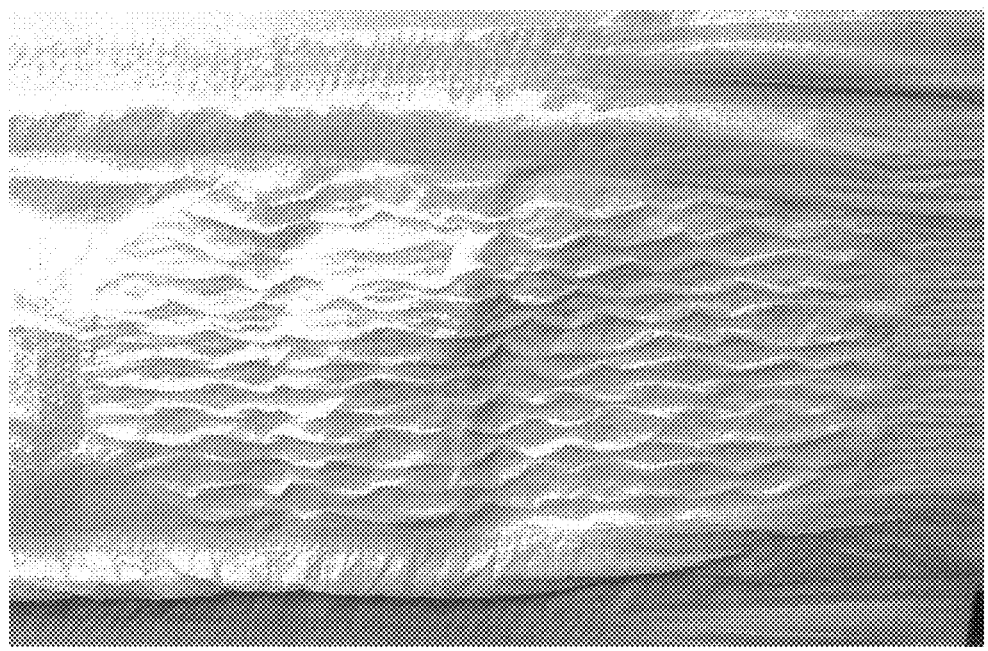
FIG. 62 is a photograph of the chemical treatment pattern of FIG. 61 on a topsheet in accordance with the present disclosure.

One or more of the various zones of the topsheet 24 and/or the liquid management system 50 may comprise one or more chemical treatments. The chemical treatments may have any suitable color, size, shape, thickness, and/or pattern. The various zones may have the same chemical treatments or different chemical treatments. More than one chemical treatment may be provided in a certain zone or in multiple zones. Some chemical treatments may surround, or at least partially surround, other zones of chemical treatments, or may surround, or at least partially surround, other geometric or morphological treatments. In other instances, some chemical treatments may at least partially overlap other chemical treatments and/or be positioned on or overlap geometric and/or morphological treatments. Some example chemical treatments are illustrated in FIGS. 58-65. Various other figures, as described above, also illustrate various chemical treatments. FIG. 58 illustrates an example chemical treatment of a pattern of printed or dyed channels on a topsheet. FIGS. 59 and 60 illustrate an example chemical treatment of a pattern of printed or dyed dots on a topsheet. FIGS. 61 and 62 illustrate a chemical treatment of a pattern of printed or dyed diamonds on a topsheet.

FIG. 63 illustrates an example of an absorbent article having a plurality of zones. One or more of the zones may comprise one or more chemical treatments and/or one or more other treatments. The first zone, Z1, may comprise a chemical treatment comprising a skin care composition, the second zone, Z2, may comprise a chemical treatment comprising an anti-stick lotion or a composition configured to aid in preventing BM from sticking to the skin of the wearer, and the third zone, Z3, may comprise a chemical treatment comprising a composition comprising an ink or a pigment. The various chemical treatments may be in patterns (e.g., stripes, dots) in the various zones. The patterns may be the same or different in various zones and/or within a certain zone. The absorbent article may also comprise deep embossed lines, EL, on either side of the third zone, Z3 and/or surrounding the first zone, Z1. The absorbent article may further comprise fourth and fifth zones, Z4 and Z5, respectively. These fourth and fifth zones, Z4 and Z5, may comprise any number of chemical, geometric, and/or morphological treatments, or may not comprise any treatments. The topsheet may also comprise flow control materials. The flow control materials may form a perimeter of, or be positioned around, the first zone Z1, the second zone Z2, and/or the third zone Z3. The flow control materials may be continuous or discontinuous.

FIG. 64 illustrates an example of an absorbent article having at least two zones, Z1, and Z2. Zone Z1 may exist at opposite ends of zone Z2. Zones Z1 and Z2 may each comprise a geometric treatment and/or a morphological treatment. One or both of the morphological treatments may comprise portions of a liquid management system extending into or at least partially through the topsheet, as explained above in reference to FIGS. 52-57. The morphological treatment in zone Z1 may have a different pattern (e.g., height, width, shape, frequency, length, spacing, color, material etc.) than the morphological treatment in zone Z2. Zones, Z1 and Z2, may also comprise a first chemical treatment, CT1 formed in dots, for example. The first chemical treatment, CT1 may comprise an anti-stick lotion or composition configured to aid in preventing BM from sticking to the skin of a wearer. Zone Z1 may also comprise a second chemical treatment, CT2, comprising an active ingredient, such as zinc oxide, or a vitamin, such as Vitamin E, for example. Zone Z2 may comprise a third chemical treatment, CT3, comprising an enzyme inhibitor, such as hexamidine, for example. The third chemical treatment, CT3, may also be a BM anti-stick lotion.

Figure 64A:
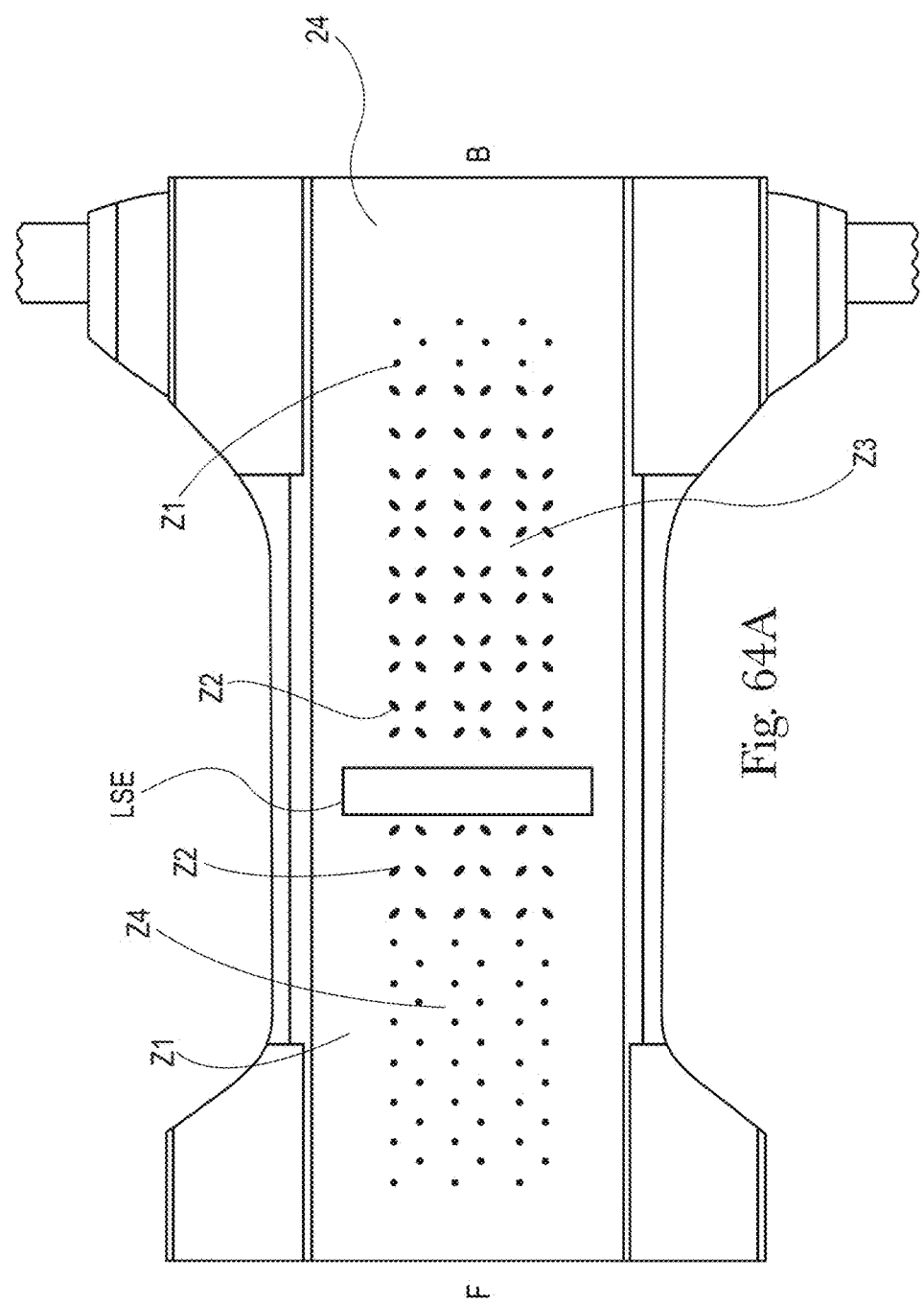

FIG. 64A illustrates an example of an absorbent article having four zones. Zone Z1 may comprise a morphological treatment (see e.g., FIGS. 52 and 54). Zone Z2 may comprise a geometric treatment comprising apertures. Zone Z3 may comprise a chemical treatment comprising a BM anti-stick lotion that may be hydrophobic or hydrophilic. Zone Z4 may comprise a chemical treatment comprising a lotion with active ingredients. The lotion of Zone Z4 may be hydrophobic or hydrophilic. Zone 4 may at least partially overlap zone 1. Zone 3 may at least partially overlap zones 1 and 2. The absorbent article may also comprise a lateral separation element LSE.

FIG. 65 illustrates an example of an absorbent article having a plurality of treatments. The first treatment, T1, may comprise a morphological treatment of deep embossing and a first chemical treatment, CT1, comprising compositions comprising inks or pigments. A second chemical treatment, CT2, may comprise an active ingredient, such as such as zinc oxide, or a vitamin, such as Vitamin E, for example. The active ingredient may be formed by a pattern of dots, for example. A third chemical treatment, CT3, may comprise one or more flow control materials. The flow control material may be formed by a pattern of stripes, for example. Any of the areas where the various treatments are present may also comprise additional treatments.

Figure 66:
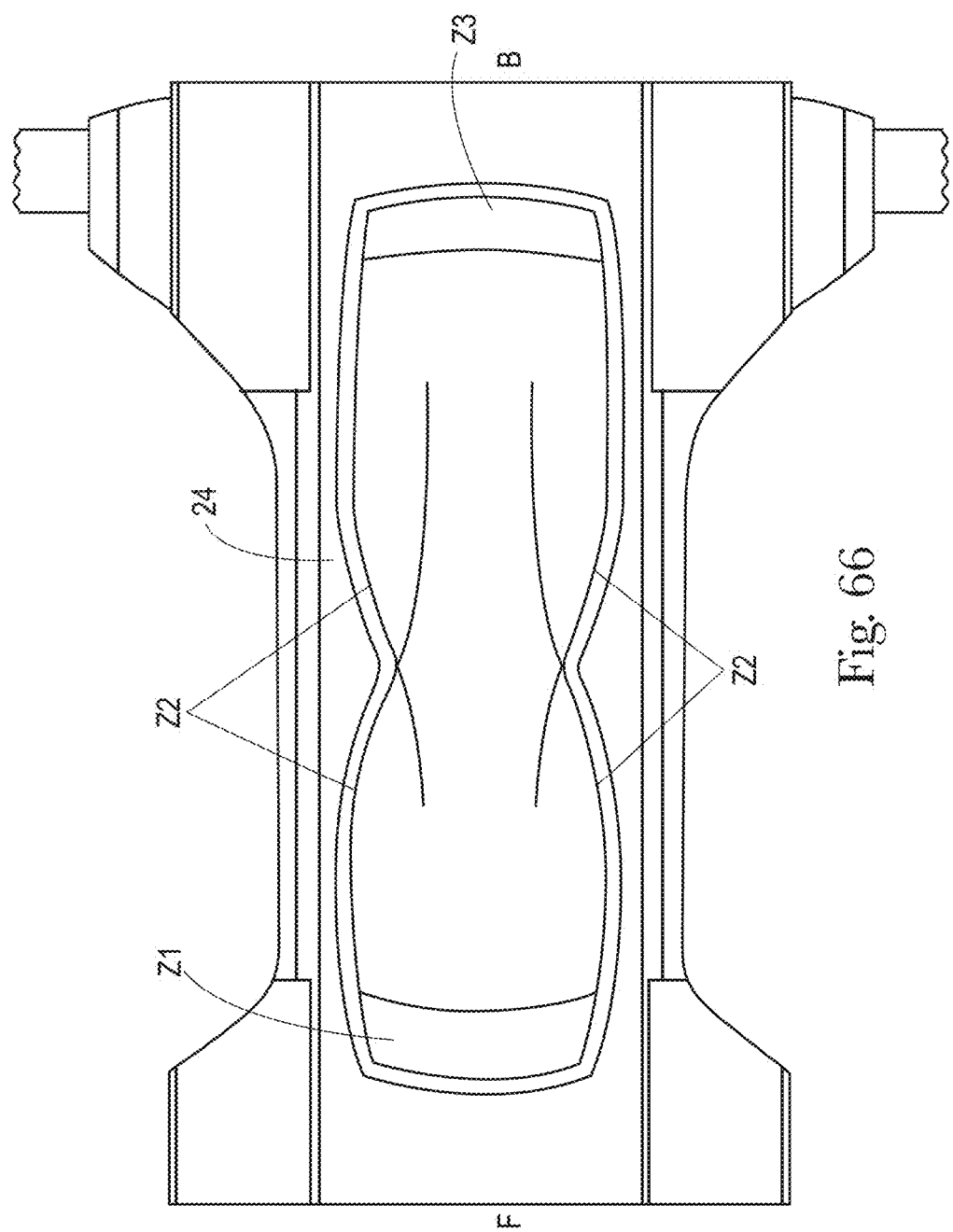

FIG. 66 illustrates an example of an absorbent article having a plurality of flow control materials in various zones. Zone Z1 may comprise a flow control material for urine. Zone Z2 may comprise a flow control material for BM. Zone Z3 may comprise a flow control material for either urine or BM. The absorbent article may also comprise one or more other treatments.

Figure 67:
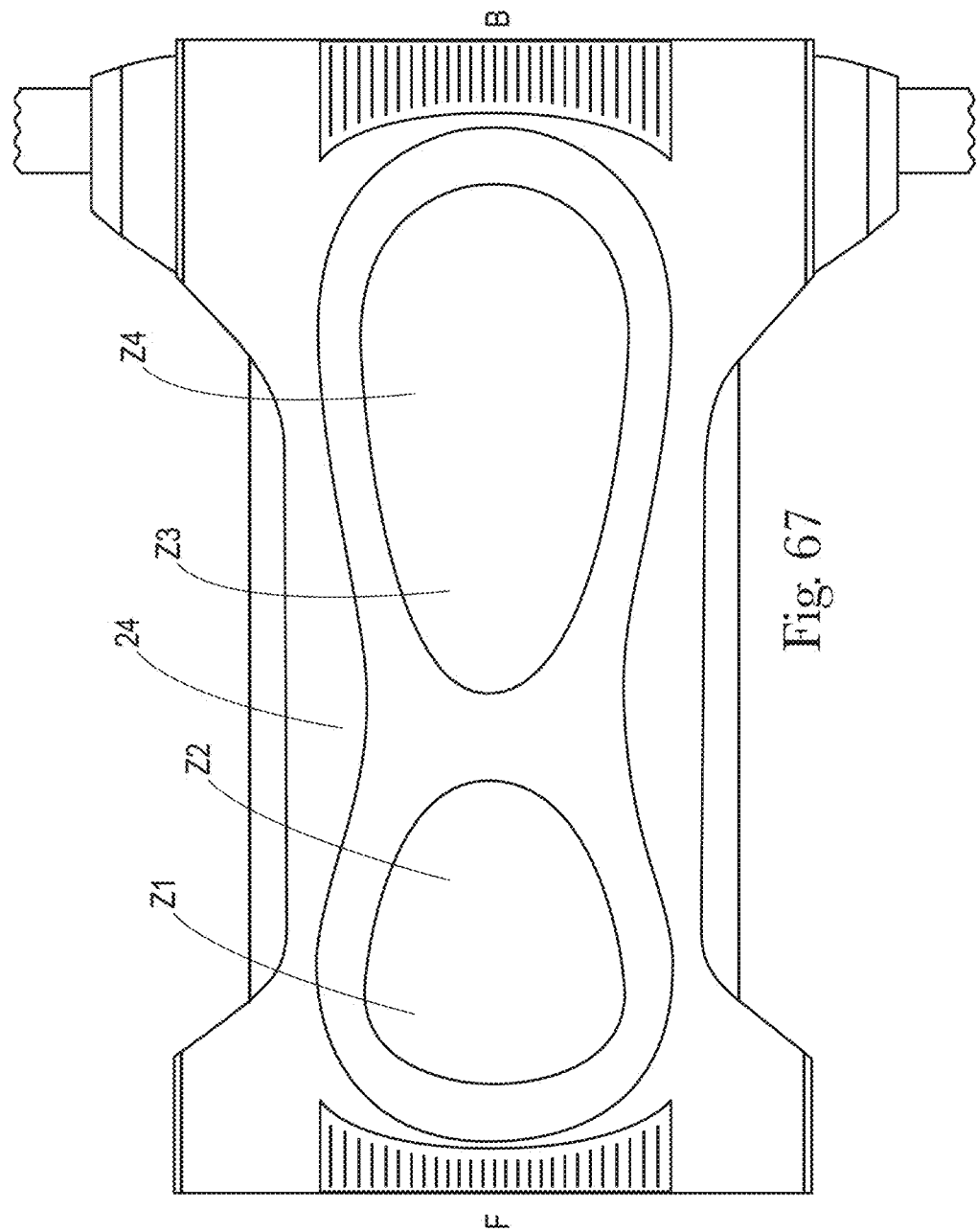

FIG. 67 illustrates an example of an absorbent article having a plurality of zones. Zone Z1 may comprise a morphological treatment (see e.g., FIGS. 52 and 54). Zone Z2 may comprise a chemical treatment. Zone Z2 may at least partially overlap zone Z1. Zone Z3 may comprise a morphological treatment (see e.g., FIGS. 52 and 54). Zone Z4 may comprise a BM anti-stick lotion. Zone Z4 may at least partially overlap Zone Z3. The absorbent article may also comprise one or more other treatments.

FIG. 68 illustrates an example of an absorbent article having a plurality of zones. Zone Z1 may comprise a geometric treatment comprising apertures. Zone Z2 may comprise a geometric treatment comprising apertures. The aperture may create a pattern. Zone Z1 may comprise a skin care composition and Zone Z2 may comprise a BM anti-stick lotion. The absorbent article may also comprise one or more other treatments.

Any of the zones having one or more chemical treatments or other treatments may overlap or not overlap portions of, or all of, the channels (e.g., 49, 49') in the liquid management system 50 and/or the channels (e.g., 26, 26', 27, 27') in the absorbent core 28.

Hydrophobic/Hydrophilic

As discussed above, various zones of the topsheet may comprise chemical treatments that render those zones hydrophobic or hydrophilic or more hydrophobic or hydrophilic. Some additional details on these zones are provided below. A topsheet of an absorbent article may comprise a first chemical treatment comprising a hydrophilic coating and/or a second chemical treatment comprising a hydrophobic coating. In other instances, only one hydrophilic coating or hydrophobic coating may be provided on a topsheet. In still other instances, the first chemical treatment may by hydrophobic and the second chemical treatment may have a different hydrophilicity (i.e., more hydrophobic, less hydrophobic, more hydrophilic, or less hydrophilic). The hydrophilic coating and the hydrophobic coating may be positioned in any suitable areas or zones of the topsheet. The topsheet may comprise a first zone comprising the hydrophilic coating and a second zone comprising the hydrophilic coating. In other instances, one or more zones in the topsheet may comprise chemical treatments comprising either hydrophilic or hydrophobic coatings. The first and second zones of the topsheet may be positioned in the front and/or the back or the front and the back, respectively, of the absorbent article. In other instances, the first and seconds zones of the topsheet may be positioned on opposite sides of a substantially laterally-extending separation element, lateral axis, or longitudinal axis.

Chemical treatments that are hydrophilic may facilitate penetration of the liquid permeable topsheet, the LMS, and/or the absorbent core by urine or runny BM or may promote adherence of the BM to the liquid permeable topsheet vs. the wearer's skin. Hydrophobic treatments may hold a skin care composition in place to facilitate bodily contact, reduce rewet, improve skin dryness, and/or may prevent, or at least inhibit, runny BM from re-soiling the skin after having passed through a portion of the liquid permeable topsheet or the LMS.

Active Ingredients/Enzyme Inhibitors/Vitamins

As mentioned above, any of various zone discussed herein or portions of the topsheets of the present disclosure may also comprise one or more active ingredients, enzyme inhibitors, and/or vitamins. An example of an active ingredient is zinc oxide, which may function as an antimicrobial agent to reduce the pathogen count on skin to help prevent opportunistic infection of the skin or urinary tract. An example of an enzyme inhibitor is hexamidine, which is a protease inhibitor which may help prevent attack by proteolytic fecal enzymes, such as trypsin, on the skin barrier, thereby reducing irritation and dermatitis. An example of a vitamin is Vitamin E, which may help stabilize the skin barrier function.

Durable/Transferrable

As discussed above, some of the zones of the topsheets may comprise a substantially durable chemical treatment and/or a substantially transferrable chemical treatment. Those treatments are discussed further below. A topsheet of an absorbent article may comprise a first chemical treatment that is substantially transferrable or that is substantially durable and/or a second chemical treatment that is substantially durable or that is substantially transferrable. In one instance, only one substantially transferrable or substantially durable chemical treatment may be provided on a topsheet. The substantially transferrable and substantially durable chemical treatments may be positioned in any suitable areas or zones of the topsheet. The topsheet may comprise a first zone comprising the first chemical treatment that is substantially transferrable or substantially durable and a second zone comprising the second chemical treatment that is substantially durable or substantially transferrable. In other instances, one or more zones in the topsheet may comprise chemical treatments that are either substantially transferrable or substantially durable. In some instances, two substantially durable or substantially transferrable chemical treatments may be provided in various zone of a topsheet. In such an instance, one of the treatments may be applied to the topsheet in a different pattern, thickness, basis weight as the other treatment. The first and second zones of the topsheet may be positioned in the front and/or the back or the front and the back, respectively, of the absorbent article. In other instances, the first and second zones of the topsheet may be positioned on opposite sides of a substantially laterally-extending separation element, lateral axis, or longitudinal axis.

Some of the benefits of having a substantially durable chemical treatment are that a chemical treatment, such as a soil capture polymer composition, may remain on the topsheet to hold the BM on the topsheet more tightly than the BM adheres to the skin to facilitate more removal of BM from the skin with the absorbent article. Other examples of substantially durable chemical treatments may include: a) a hydrophilic treatment to help maintain urine penetration with subsequent urine events (i.e., after the first urination event), and/or b) a flow control material to preferentially restrict urine penetration in select regions of the topsheet (as described in greater detail below).

Some of the benefits of having a substantially transferrable chemical treatment are that a chemical treatment, such as a skin care composition, may be at least partially transferred to the skin of the wearer for skin barrier enhancement vs. irritants or other skin health benefits. Another example of substantially transferrable chemical treatments is BM antistick lotion which would prevent, or at least inhibit, BM adhesion to skin.

Flow Control Materials

As discussed above, some of the zones of the topsheets may comprise chemical treatments comprising flow control material. Those flow control material are discussed further below.

The flow control materials may hasten, slow, or restrict the movement and/or penetration of bodily exudates on, into, or through a topsheet of an absorbent article.

A topsheet may comprise a first chemical treatment comprising a first flow control material (see FIG. 21C, Z5) and/or a second chemical treatment comprising a second flow control material (see FIG. 21C, Z5). These flow control materials may be the same or different. In one instance, only one flow control material may be provided on a topsheet. The first and second flow control materials may be positioned in any suitable areas, zones, and/or portions of the topsheet. The topsheet may comprise a first zone (see FIG. 15 Z1) comprising the first flow control material and a second zone (see FIG. 15, Z2) comprising the second flow control material. The first and second zones of the topsheet may be positioned in the front and/or the back or the front and the back, respectively, of the absorbent article. In other instances, the first and second zones of the topsheet may be at last partially positioned on opposite sides of a substantially laterally-extending separation element (see FIG. 15), lateral axis, or longitudinal axis.

The first and second flow control materials may be the same or different. The first flow control material may have a different permeability, basis weight, surface energy, and/or thickness compared to the second flow control material. The first flow control material and/or the second flow control material may comprise a pigment, a colorant, a printed ink, a dye, and/or a skin care composition. The pigments, colorants, printed inks, dyes, and/or skin care compositions of the first and second flow control materials may be the same or different.

The first and second flow control materials may have different patterns in different zones (see e.g. FIG. 21A, Z2 and Z4), for example, a first pattern in a first zone and a second pattern in a second zone, or may have the same patterns in different zones.

Flow control materials may at least partially, or fully, restrict or slow penetration of liquid bodily exudates in certain regions of the absorbent article and direct the exudates to regions where they may be preferentially stored (i.e., to reduce bulkiness, to improve fit, and/or to improve (reduce) rewet to the skin) For example, if the flow control material is located in a region where urine is expected to insult the product from the wearer and is directed in either or both longitudinal directions, this may reduce the wet bulk in the crotch region. Such a feature may also provide appearance and/or comfort/freedom of motion benefits for the absorbent article. Alternatively, the flow control material may prevent, or at least inhibit, rewet of bodily exudates (i.e., that have travelled through the topsheet) back through certain regions of the topsheet to avoid soiling otherwise uncontaminated skin.

In other instances, the flow control materials may hasten the flow of bodily exudates either across a topsheet or into or through a topsheet to allow the absorbent article to more effectively absorb the bodily exudates.

As an example of a flow control material, an absorbent article may comprise a liquid permeable topsheet, a liquid impermeable backsheet, and an absorbent core positioned at least partially intermediate the liquid permeable topsheet and the liquid impermeable backsheet. The liquid permeable topsheet may comprise a flow control material that may form an at least mostly, or fully, enclosed perimeter over at least a portion of the absorbent core (see e.g., FIG. 20, Z2-Z4, FIG. 21A, Z5, FIG. 21B, Z3, FIG. 21C, Z4, FIG. 24, Z1, Z3, and Z4, FIG. 29, Z3, and FIGS. 39-42, for example. The term "at least mostly enclosed perimeter" means a perimeter that is at least 60% enclosed (i.e., 60% of a full enclosed shape is formed). The at least mostly enclosed perimeter, or fully enclosed perimeter, may be continuous (see FIGS. 20, Z3 and Z4, 21A, Z5, 21B, Z3, 21C, Z4) or discontinuous (see FIGS. 39-42). Discontinuous flow control material may be provided in a pattern of elements, such as stripes, dots, dashed lines, etc. The flow control material may extend less than 0.2 mm, or more than 0.2 mm, outwardly from the liquid permeable topsheet (measured according to the Flow Control Material Outward Extension Method herein) and may penetrate into or through a portion of the liquid permeable topsheet. The flow control material may also be applied to the liquid management system.

The topsheet may also comprise one or more geometric treatments, morphological treatments, and/or chemical treatments (chemical treatments other than flow control materials). Referring to FIG. 20, the geometric treatment Z2 may be fully positioned within, or partially positioned within, on, or outside of, or at least partially outside of, the at least mostly enclosed perimeter P1, or the fully enclosed perimeter formed by the first flow control material Z4. The topsheet 24 may also comprise a second flow control 500 material forming a second at least mostly, or fully, enclosed perimeter P2 in the topsheet 24. The second perimeter P2 may be at least partially, or fully, positioned within the at least mostly enclosed perimeter P1. A second geometric treatment, a second morphological treatment, or a second chemical treatment Z1 may be at least partially, or fully, positioned within the at least mostly enclosed second perimeter P2. The topsheet may also comprise one or more additional chemical treatments. The chemical treatments may be positioned on, inside, or outside of the perimeter P1 or the second perimeter P2.

The flow control material may penetrate through at least 5%, at least 10%, at least 15%, at least 20%, at least 25%, at least 50%, or more of a thickness of the liquid permeable topsheet. The flow control material may also penetrate onto and/or at least partially through the liquid management system of the absorbent article. In some instances, the flow control material may only be present on a surface of the topsheet or the liquid management system and/or the absorbent core. In other instances the flow control material may penetrate fully through the topsheet and/or the liquid management system. In still other instances, the flow control material may penetrate the topsheet or the liquid management system in the range of 1% to 75%, 5% to 50%, 5% to 50%, and 5% to 25% specifically reciting all 0.1% increments within the specified ranges and all ranges formed therein or thereby. The flow control materials may be applied to the topsheet or the liquid management system by any suitable methods known to those of skill in the art, such as spraying, melting, and rolling.

The flow control material may penetrate through at a depth of at least about 50 micrometers, at least about 75 micrometers, at least about 100 micrometers, at least about 150 micrometers, at least about 200 micrometers, at least about 250 micrometers, at least about 300 micrometers, or at least about 350 micrometers, below a wearer-facing surface of the topsheet, measured according to the Penetration Depth Test Method herein. The flow control material may also penetrate through at a depth in the range of about 25 micrometers to about 500 micrometers, about 50 micrometers to about 500 micrometers, about 100 micrometers to about 400 micrometers, about 100 micrometers to about 300 micrometers, about 150 micrometers to about 300 micrometers, or about 100 micrometers to about 250 micrometers, specifically reciting all 0.5 micrometer increments within the above-specified ranges and all ranges formed therein or thereby, below a wearer-facing surface of the topsheet, measured according to the Penetration Depth Test Method herein.

As another example, an absorbent article may comprise a liquid permeable topsheet, a liquid impermeable backsheet, a lateral axis defining a front region of the absorbent article on a first side of the lateral axis and a back region of the absorbent article on a second side of the lateral axis, and an absorbent core positioned at least partially intermediate the liquid permeable topsheet and the liquid impermeable backsheet. Referring generally to FIG. 15, the liquid permeable topsheet 24 may comprise a first zone Z1 situated primarily (e.g., at least 60%, or at least 75%) in the front region and comprising a first flow control material and a second zone Z2 situated primarily (e.g., at least 60%, or at least 75%) in the back region and comprising a second flow control material. The first flow control material may be different than, or the same as, the second flow control material. The first and second flow control material may be applied at the same or different basis weights and/or thicknesses. At least a portion of the first and second flow control materials may be deposited on or adjacent to a longitudinal axis 80 of the absorbent article. The first flow control material may comprise a different (or the same) pattern, shape, and/or coverage area than the second flow control material. The first zone Z1 may also comprise a first geometric treatment and the second zone Z2 may also comprise a second geometric treatment. The first flow control material may be associated with (e.g., positioned on, under, within, over, working in combination with) the first geometric treatment and the second flow control material may be associated with the second geometric treatment.

The flow control material(s) may also be positioned at: a) areas of a topsheet or liquid management system of an absorbent article which, in use, will be subjected to "high pressure" from the body (e.g., under the ischia or buttocks cheeks); b) at or proximate to a perimeter of the absorbent core; c) at or proximate to a location where the bodily exudates are expected to insult the absorbent article (i.e., to direct the bodily exudates to either the front or back portions (or other portions) of the absorbent article); d) at or proximate to perimeters of various zones, e) about or proximate to the lateral axis; or f) about a or proximate to, or on, a laterally extending separation element.

The absorbent article may comprise a liquid management system positioned at least partially intermediate the liquid permeable topsheet and the absorbent core. The liquid management system may comprise a third flow control material applied thereto and positioned to form an at least mostly, or fully, enclosed perimeter over a portion of the absorbent core.

As another example, an absorbent article may comprise a liquid permeable topsheet, a liquid impermeable backsheet, a liquid management system, and an absorbent core positioned at least partially intermediate the liquid management system and the liquid impermeable backsheet. The liquid management system may be positioned at least partially intermediate the liquid permeable topsheet and the absorbent core. Referring to FIG. 21, the liquid permeable topsheet 24 or the liquid management system may comprise a flow control material 502 positioned in or surrounding, or at least partially surrounding, a urine insult zone 504 and/or a feces insult zone 506. In other instances, the liquid permeable topsheet or the liquid management system may comprise a first flow control material 502 positioned in or surrounding, or at least partially surrounding a urine insult zone 504 and may comprise a second flow control material 502' positioned in or surrounding, or at least partially surrounding a feces insult zone 506.

Any of the various zones, or one or more portions thereof, either in addition to or in lieu of the various treatments discussed herein, may have one or more colors, shades of the same color, different colors, and/or different delta E values. For example, a first zone, or one or more portions thereof, may have a first color and a second zone (or third or fourth zone etc.), or one or more portions thereof, may have a second color. The first and second colors may be the same or different. In certain instances, all or some of zones, or one or more portions thereof, in a front region of an absorbent article may have the same or different colors as all or some of the zones, or portions thereof, in a rear region of the absorbent article. In some instances, the various treatments may have colors that are the same or different. The color may be provided by or on any of the materials, treatments (e.g., chemical treatments), and/or layers (e.g., acquisition layer) within the various zones.

Test Methods

Condition all samples at about 23° C.±2 C.° and about 50%±2% relative humidity for 2 hours prior to testing.

Aperture Test

Aperture dimensions, effective aperture area, and % effective open area measurements are performed on images generated using a flat bed scanner capable of scanning in reflectance mode at a resolution of 6400 dpi and 8 bit grayscale (a suitable scanner is the Epson Perfection V750 Pro, Epson, USA). Analyses are performed using ImageJ software (v.s 1.46, National Institute of Health, USA) and calibrated against a ruler certified by NIST. A steel frame (100 mm square, 1.5 mm thick with an opening 60 mm square) is used to mount the specimen and a black glass tile (P/N 11-0050-30, available from HunterLab, Reston, Va.) is used as the background for the scanned images. Take the steel frame and place double-sided adhesive tape on the bottom surface surrounding the interior opening. To obtain a specimen, lay the absorbent article flat on a lab bench with the wearer-facing surface directed upward. Remove the release paper of the tape, and adhere the steel frame to the topsheet of the absorbent article. Using a razor blade, excise the top sheet from the underling layers of the absorbent article around the outer perimeter of the frame. Carefully remove the specimen such that its longitudinal and lateral extension is maintained. A cryogenic spray (such as Cyto-Freeze, Control Company, Houston Tex.) can be used to remove the topsheet specimen from the underling layers, if necessary. Five replicates obtained from five substantially similar absorbent articles are prepared for analysis.

Place the ruler on the scanner bed, close the lid and acquire a 50 mm by 50 mm calibration image of the ruler in reflectance mode at a resolution of 6400 dpi and 8 bit grayscale. Save the image as an uncompressed TIFF format file. Lift the lid and remove the ruler. After obtaining the calibration image, all specimens are scanned under the same conditions and measured based on the same calibration file. Next, place the framed specimen onto the center of the scanner bed with the wearer-facing surface of the specimen facing the scanner's glass surface. Place the black glass tile on top of the frame covering the specimen, close the lid and acquire a scanned image. In like fashion scan the remaining four replicates.

Open the calibration file in ImageJ and perform a linear calibration using the imaged ruler, with the scale set to Global so that the calibration will be applied to subsequent specimens. Open a specimen image in ImageJ. View the histogram and identify the gray level value for the minimum population located between the dark pixel peak of the holes and the lighter pixel peak of the nonwoven. Threshold the image at the minimum gray level value to generate a binary image. In the processed image, the apertures appear as black and nonwoven as white.

Select the analyze particles function. Set the minimum aperture area exclusion limit to 0.3 mm$^2$ and for the analysis to exclude the edge apertures. Set the software to calculate: effective aperture area, perimeter, feret (length of the aperture) and minimum feret (width of the aperture). Record the average effective aperture area to the nearest 0.01 mm$^2$, and the average perimeter to the nearest 0.01 mm. Again select the analyze particles function, but this time set the analysis to include the edge holes as it calculates the effective aperture areas. Sum the effective aperture areas (includes whole and partial apertures) and divide by the total area included in the image (2500 mm$^2$). Record as the % effective open area to the nearest 0.01%.

In like fashion analyze the remaining four specimen images. Calculate and report the average effective aperture area to the nearest 0.01 mm$^2$, the average aperture perimeter to the nearest 0.01 mm, feret and minimum feret to the nearest 0.01 mm, and the % effective open area to the nearest 0.01% for the five replicates.

Flow Control Material Outward Extension Method/Flow Control Material Penetration Depth Method
Experimental Settings The values indicated herein are measured according to the methods indicated herein below, unless specified otherwise. All measurements are performed at 21° C.±2° C. and 50%±20% RH, unless specified otherwise. All samples should be kept at least 24 hours in these conditions to equilibrate before conducting the tests, unless indicated otherwise. All measurements should be reproduced on at least 4 samples and the average value obtained indicated, unless otherwise indicated.

Equipment
Razor blade: VWR Single Edge Industrial, 0.009" thick surgical carbon steel or equivalent.
SEM (Hitachi S3500N or equivalent)

Procedure
An area 1.5 cm to 3 cm in length and 1.3 cm in width is cut from an absorbent article in an area where the liquid permeable topsheet comprises a flow control material. This subsample is sectioned along the length, using a new razor blade (VWR Single Edge Industrial, 0.009" thick surgical carbon steel or equivalent.) If the topsheet contains protruded or inverted elements, the cross-sections should be made across the middle of these features. The sectioned subsample is adhered to an SEM mount using double-sided conductive tape, with the topsheet's wearer-facing surface of the section up and sectioned edge at the mount edge, so that the cross-section is revealed when the SEM stage is tilted backward 90°. The mounted sample is sputter Au coated and viewed in an SEM (Hitachi S3500N or equivalent).

The following measurements should be made with the manual line tool in PCI v4.2 image analysis software (or equivalent) from cross-sectional images:

(1) Flow Control Material Outward Extension Method is determined by obtaining the z-directional distance between the point where flow control material is no longer observed in an outward, wearer-facing direction, and the nearest point on the topsheet's wearer-facing surface where there is no flow control material within the image area. Three areas should be measured if the topsheet is planar, and line lengths averaged. If the topsheet contains protrusions and/or inversions, three areas should be measured for the protrusions (if there are any), three for the inversions (if there are any), and three from land area between these features (if there is any). Line lengths measured at protrusions are averaged; line lengths measured at inversions are averaged, and line lengths measured at land area are averaged. The smallest of the three measurements is designated the Flow Control Material Outward Extension and reported in micrometers to the nearest 0.1 micrometer.

(2) Flow Control Material Penetration Depth Method is determined by measuring the z-directional distance between the lowest point the flow control material is observed in a cross-sectional image (in the z-direction away from the wearer) and the nearest point on the topsheet's wearer-facing surface where there is no flow control material on. Three areas should be measured if the topsheet system is planar, and line lengths averaged. If the topsheet contains protrusions and/or inversions, three areas should be measured for the protrusions (if there are any), three for the inversions (if there are any), and three from land area between these features (if there is any). Line lengths measured at protrusions are averaged; line lengths measured at inversions are averaged, and line lengths measured at land area are averaged. Flow Control Material Penetration Depth is designated as the higher of these measurements and reported in micrometers to the nearest 0.1 micrometer.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any embodiment disclosed or claimed herein or that it alone, or in any combination with any other reference or references, teaches, suggests or discloses any such embodiment. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it will be understood by those skilled in the art that various other changes and modifications may be made without departing from the spirit and scope of the present disclosure. It is therefore intended to cover in the appended claims all such changes and modifications that are within the scope of this disclosure.

What is claimed is:

1. An absorbent article comprising:
   a liquid permeable topsheet;
   a liquid impermeable backsheet;
   a central lateral axis defining a front region on a first side of the central lateral axis and a back region on a second side of the central lateral axis;
   a laterally-extending structural separator extending upwardly relative to a portion of the liquid permeable topsheet, wherein the laterally-extending structural separator defines the front region on a first side of the structural separator and the back region on a second side of the structural separator, and wherein the laterally-extending structural separator crosses a central longitudinal axis of the absorbent article;
   an absorbent core positioned at least partially intermediate the liquid permeable topsheet and the liquid impermeable backsheet, wherein the absorbent core comprises an absorbent material, and wherein the absorbent material defines a first channel therethrough; and
   a liquid management system positioned at least partially intermediate the liquid permeable topsheet and the absorbent core, wherein the liquid management system defines a second channel therethrough;
   wherein the liquid permeable topsheet comprises a first zone situated primarily in the front region and having a substantially transferrable chemical treatment and a second zone situated primarily in the back region and having the substantially transferrable chemical treatment, and wherein a basis weight of the substantially transferrable chemical treatment is greater in the second zone than in the first zone.

2. The absorbent article of claim 1, wherein the substantially transferrable chemical treatment comprises a skin care composition.

3. The absorbent article of claim 1, wherein the liquid permeable topsheet comprises a substantially durable chemical treatment.

4. The absorbent article of claim 3, wherein the substantially durable chemical treatment comprises an ink.

5. The absorbent article of claim 1, wherein portions of the liquid management system extend into or through portions of the liquid permeable topsheet.

6. The absorbent article of claim 1, wherein portions of the liquid permeable topsheet extend into or through portions of the liquid management system.

7. The absorbent article of claim 1, comprising a morphological treatment in the first or second zones.

8. The absorbent article of claim 7, wherein the substantially transferrable chemical treatment overlaps a portion of the morphological treatment.

9. The absorbent article of claim 1, comprising a geometric treatment in the first or second zone.

10. The absorbent article of claim 9, wherein the substantially transferrable chemical treatment overlaps a portion of the geometrical treatment.

11. The absorbent article of claim 1, wherein the first zone or the second zone comprises a second chemical treatment.

12. The absorbent article of claim 1, wherein a portion of the substantially transferable chemical treatment overlaps a portion of the second channel.

13. The absorbent article of claim 1, wherein a portion of the substantially transferable chemical treatment does not overlap a portion of the second channel.

14. A diaper or a pant comprising:
   a liquid permeable topsheet;
   a liquid impermeable backsheet;
   a laterally-extending structural separator extending upwardly relative to a portion of the topsheet and defining a front region on a first side of the structural separator and a back region on a second side of the structural separator, wherein the laterally-extending structural separator crosses a central longitudinal axis of the absorbent article;
   an absorbent core positioned at least partially intermediate the liquid permeable topsheet and the liquid impermeable backsheet, wherein the absorbent core comprises an absorbent material, and wherein the absorbent material defines a first channel therethrough; and
   a liquid management system positioned at least partially intermediate the liquid permeable topsheet and the absorbent core, wherein the liquid management system defines a second channel therethrough;
   wherein the liquid permeable topsheet comprises a first zone situated primarily in the front region and having a first substantially transferrable chemical treatment that is hydrophobic and a second zone situated primarily in the back region and having a second substantially transferrable chemical treatment that has a different hydrophilicity as the first chemical treatment.

15. The absorbent article of claim 14, wherein the second chemical treatment is more hydrophilic than the first chemical treatment.

16. The absorbent article of claim 14, wherein the second chemical treatment is hydrophobic.

17. The absorbent article of claim 14, wherein the second chemical treatment is more hydrophobic than the first chemical treatment.

18. The absorbent article of claim 1, wherein the topsheet is a nonwoven material.

19. An absorbent article comprising:
   a liquid permeable topsheet;
   a liquid impermeable backsheet;
   a central lateral axis defining a front region on a first side of the central lateral axis and a back region on a second side of the central lateral axis;
   a laterally-extending structural separator extending upwardly relative to a portion of the topsheet and defining the front region on a first side of the structural separator and the back region on a second side of the structural separator, wherein the laterally-extending structural separator crosses a central longitudinal axis of the absorbent article; and
   an absorbent core positioned at least partially intermediate the liquid permeable topsheet and the liquid impermeable backsheet, wherein the absorbent core comprises an absorbent material, wherein the absorbent material defines a channel therethrough, and wherein the channel crosses the central lateral axis, but is free of intersection with the central longitudinal axis;

a liquid management system positioned at least partially intermediate the liquid permeable topsheet and the absorbent core, wherein the liquid management system defines a second channel therethrough;

wherein the liquid permeable topsheet comprises a first zone situated primarily in the front region and having a first substantially transferrable chemical treatment and a second zone situated primarily in the back region and having a second substantially transferrable chemical treatment, wherein a basis weight of the second substantially transferrable chemical treatment is greater in the second zone than the basis weight of the first substantially transferrable chemical treatment in the first zone, and wherein the first substantially transferrable chemical treatment has a different composition than the second substantially transferrable chemical treatment.

20. The absorbent article of claim 19, wherein portions of the liquid management system extend into or through portions of the liquid permeable topsheet.

\* \* \* \* \*